(12) United States Patent
Straub et al.

(10) Patent No.: US 7,767,702 B2
(45) Date of Patent: *Aug. 3, 2010

(54) SUBSTITUTED OXAZOLIDINONES FOR COMBINATIONAL THERAPY

(75) Inventors: Alexander Straub, Wuppertal (DE); Thomas Lampe, Düsseldorf (DE); Josef Pernerstorfer, Wuppertal (DE); Elisabeth Perzborn, Wuppertal (DE); Jens Pohlmann, Wuppertal (DE); Susanne Röhrig, Essen (DE); Karl-Heinz Schlemmer, Wuppertal (DE)

(73) Assignee: Bayer Schering Pharma Aktiengesellschaft (DE)

( * ) Notice: Subject to any disclaimer, the term of this patent is extended or adjusted under 35 U.S.C. 154(b) by 1466 days.

This patent is subject to a terminal disclaimer.

(21) Appl. No.: 10/481,297

(22) PCT Filed: Jun. 7, 2002

(86) PCT No.: PCT/EP02/06237

§ 371 (c)(1), (2), (4) Date: Jun. 28, 2004

(87) PCT Pub. No.: WO03/000256

PCT Pub. Date: Jan. 3, 2003

(65) Prior Publication Data

US 2004/0242660 A1 Dec. 2, 2004

(30) Foreign Application Priority Data

Jun. 20, 2001 (DE) ................. 101 29 725

(51) Int. Cl.
*A61K 31/421* (2006.01)
(52) U.S. Cl. .................................... 514/376
(58) Field of Classification Search ........... None
See application file for complete search history.

(56) References Cited

U.S. PATENT DOCUMENTS

| | | | |
|---|---|---|---|
| 2,811,555 A | 10/1957 | Larive et al. | |
| 3,279,880 A | 10/1966 | Straley et al. | |
| 4,128,654 A | 12/1978 | Fugitt et al. | |
| 4,250,318 A | 2/1981 | Dostert et al. | |
| 4,327,725 A | 5/1982 | Cortese et al. | |
| 4,500,519 A | 2/1985 | Lormeau et al. | |
| 4,705,779 A | 11/1987 | Madi-Szabo et al. | |
| 4,765,989 A | 8/1988 | Wong et al. | |
| 5,002,937 A | 3/1991 | Bosies et al. | |
| 5,254,577 A | 10/1993 | Carlson et al. | |
| 5,349,045 A | 9/1994 | Jiang | |
| 5,532,255 A | 7/1996 | Raddatz et al. | 514/326 |
| 5,561,148 A | 10/1996 | Gante et al. | |
| 5,565,571 A | 10/1996 | Barbachyn et al. | |
| 5,654,285 A * | 8/1997 | Ingall et al. | 514/47 |
| 5,654,428 A | 8/1997 | Barbachyn et al. | |
| 5,654,435 A | 8/1997 | Barbachyn et al. | |
| 5,688,792 A | 11/1997 | Barbachyn et al. | |
| 5,756,732 A | 5/1998 | Barbachyn et al. | |
| 5,792,765 A | 8/1998 | Riedl et al. | |
| 5,801,246 A | 9/1998 | Barbachyn et al. | |
| 5,827,857 A | 10/1998 | Riedl et al. | |
| 5,910,504 A | 6/1999 | Hutchinson | |
| 5,922,708 A | 7/1999 | Riedl et al. | |
| 5,929,248 A | 7/1999 | Barbachyn et al. | |
| 5,972,947 A | 10/1999 | Tsaklakidis et al. | |
| 6,069,160 A | 5/2000 | Stolle et al. | |
| 6,159,997 A | 12/2000 | Tsujita et al. | 514/369 |
| 6,251,869 B1 | 6/2001 | Bohanon | |
| 6,294,201 B1 | 9/2001 | Kettelhoit et al. | |
| 6,805,881 B1 | 10/2004 | Kanikanti et al. | |
| 6,818,243 B2 | 11/2004 | Nagashima et al. | |
| 7,034,017 B2 | 4/2006 | Straub et al. | |
| 7,078,417 B2 | 7/2006 | Rosentreter et al. | |
| 7,109,218 B2 | 9/2006 | Rosentreter et al. | |
| 7,129,255 B2 | 10/2006 | Rosentreter et al. | |
| 7,157,456 B2 * | 1/2007 | Straub et al. | 514/236.8 |
| 7,351,823 B2 | 4/2008 | Berwe et al. | |

(Continued)

FOREIGN PATENT DOCUMENTS

AU 744002 B2 7/1999

(Continued)

OTHER PUBLICATIONS

Bono, F., et al, "Human Umbilical Vein Endothelial Cells Express High Affinity Receptors for Factor Xa", Journal of Cellular Physiology, 1997, vol. 172, pp. 36-43.

(Continued)

*Primary Examiner*—Brian-Yong S Kwon
(74) *Attorney, Agent, or Firm*—Connolly Bove Lodge & Hutz, LLP

(57) ABSTRACT

The invention relates to combinations of A) oxazolidinones of formula (I) and B) other active ingredients, to a method for producing said combinations and to the use thereof as medicaments, in particular for the treatment and/or prophylaxis of thrombo-embolic diseases.

(I)

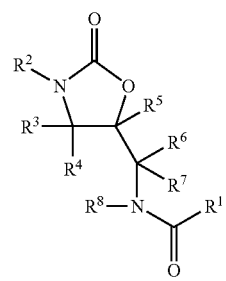

4 Claims, No Drawings

U.S. PATENT DOCUMENTS

| | | |
|---|---|---|
| 2001/0029351 A1 | 10/2001 | Falotico et al. |
| 2003/0153610 A1 | 8/2003 | Straub et al. |
| 2003/0161882 A1 | 8/2003 | Waterman |
| 2004/0162427 A1 | 8/2004 | Rosentreter et al. |
| 2004/0242660 A1 | 12/2004 | Straub et al. |
| 2005/0064006 A1 | 3/2005 | Perzborn et al. |
| 2005/0182055 A1 | 8/2005 | Berwe et al. |
| 2005/0261502 A1 | 11/2005 | Rosentreter et al. |
| 2006/0154969 A1 | 7/2006 | Rosentreter et al. |
| 2006/0258724 A1 | 11/2006 | Straub et al. |
| 2007/0026065 A1 | 2/2007 | Benke et al. |
| 2007/0149522 A1 | 6/2007 | Thomas |
| 2008/0026057 A1 | 1/2008 | Benke |
| 2008/0090815 A1 | 4/2008 | Straub et al. |
| 2008/0200674 A1 | 8/2008 | Straub et al. |

FOREIGN PATENT DOCUMENTS

| | | |
|---|---|---|
| CA | 2 437 587 A1 | 8/2002 |
| CA | 2 451 258 A1 | 1/2003 |
| CA | 2 464 290 A1 | 5/2003 |
| DE | 2836305 A1 | 3/1979 |
| DE | 196 04 223 A1 | 8/1997 |
| DE | 19962924 * | 7/2001 |
| DE | 10129725 A1 | 1/2003 |
| DE | 10355461 A1 | 6/2005 |
| EP | 0 127 902 A2 | 12/1984 |
| EP | 0 316 594 A1 | 5/1989 |
| EP | 0 352 781 A2 | 1/1990 |
| EP | 0350002 A1 | 1/1990 |
| EP | 0 623 615 A1 | 11/1994 |
| EP | 0645376 A1 | 3/1995 |
| EP | 0 738 726 A1 | 10/1996 |
| EP | 0 785 200 A2 | 7/1997 |
| EP | 0930076 | 7/1999 |
| EP | 0950386 A2 | 10/1999 |
| EP | 10105989 | 2/2001 |
| GB | 2140687 | 12/1984 |
| WO | WO-93/09103 A1 | 5/1993 |
| WO | WO-93/23384 A1 | 11/1993 |
| WO | WO-97/03072 A1 | 1/1997 |
| WO | WO-97/09328 A1 | 3/1997 |
| WO | WO-97/10223 A1 | 3/1997 |
| WO | WO-9723212 A1 | 7/1997 |
| WO | WO-98/01446 A1 | 1/1998 |
| WO | WO-9811896 A1 | 3/1998 |
| WO | WO-98/54161 A1 | 12/1998 |
| WO | WO-99/02525 A1 | 1/1999 |
| WO | WO-99/03846 A1 | 1/1999 |
| WO | WO-99/06371 A1 | 2/1999 |
| WO | WO-99/21535 A1 | 5/1999 |
| WO | WO-99/24428 A1 | 5/1999 |
| WO | 9931092 | 6/1999 |
| WO | WO-99/29688 A1 | 6/1999 |
| WO | WO-99/31092 A1 | 6/1999 |
| WO | WO-99/37304 A1 | 7/1999 |
| WO | WO-99/37630 A1 | 7/1999 |
| WO | WO-99/37641 A1 | 7/1999 |
| WO | WO-99/40094 A1 | 8/1999 |
| WO | WO-99/59616 A1 | 11/1999 |
| WO | WO-00/16748 A1 | 3/2000 |
| WO | WO- 01/42242 | 6/2001 |
| WO | WO-01/44212 A1 | 6/2001 |
| WO | WO-01/46185 A1 | 6/2001 |
| WO | 0147919 | 7/2001 |
| WO | WO-01/47949 A1 | 7/2001 |
| WO | WO-02/064575 A1 | 8/2002 |
| WO | WO-03/000256 A1 | 1/2003 |
| WO | WO-03/035133 A1 | 5/2003 |
| WO | WO-03/035133 A1 | 5/2003 |
| WO | WO-2004/060887 A1 | 7/2004 |
| WO | WO-2005/060940 A1 | 5/2005 |
| WO | WO-2005/068456 A1 | 7/2005 |
| WO | WO-2006/072367 A1 | 7/2006 |
| WO | WO-2006/079474 A1 | 8/2006 |
| WO | WO-2007/036306 A1 | 4/2007 |
| WO | WO-2007/039122 A2 | 4/2007 |
| WO | WO-2007/039132 A1 | 4/2007 |
| WO | WO-2007/042146 A1 | 4/2007 |
| WO | WO-2008/012002 A1 | 1/2008 |
| WO | WO-2008/052671 A1 | 2/2008 |

OTHER PUBLICATIONS

Cocks, T. M., et al., "Protease-Activated Receptors: Sentries for Inflammation", Tips, 2000, vol. 21, pp. 103-108.

Ross, R., "Atherosclerosis- An Inflammatory Disease", New England J. of Medicine, 1999, vol. 340, No. 2, pp. 115-126.

Nakata, M., et al., "DX9065a an Xa Inhibitor, Inhibits Prothrombin-Induced A549 Lung Adenocarcinoma Cell Proliferation", Cancer Letters, 1998, vol. 122, pp. 127-133.

Kaiser, B., et al., "A Synthetic Inhibitor of Factor Xa, DX-9065a, Reduces Proliferation of Vascular Smooth Muscle Cells in Vivo in Rats", Thrombosis Research, 2000, vol. 98, pp. 175-185.

Altieri, D. C., et al., "Identification of Effector Cell Protease Receptor-1", The Journal of Immunology, 1990, vol. 145, No. 1, pp. 246-253.

Coughlin, S. R., "Thrombin Signalling and Protease-Activated Receptors", Nature, 2000, vol. 407, pp. 258-264.

Ornstein, D. L., et al., "Cancer, Thrombosis, and Anticoagulants", Current Opinion in Pulmonary Medicine, 2000, vol. 6, pp. 301-308.

Dabbagh, K., et al., "Thrombin Stimulates Smooth Muscle Cell Procollagen Synthesis and mRNA Levels via a PAR-1 Mediated Mechanism", Thrombasis and Haemostasis, vol. 79, No. 2 1997, pp. 405-409.

Herault, J-P., et al., "Activation of Human Vascular Endothelial Cells by Factor Xa: Effect of Specific Inhibitors", Biochemical Pharmacology, 1999, vol. 57, pp. 603-610.

Leveugle, B., et al., "Heparin Oligosaccharides that Pass the Blood-Brain Barrier Inhibit β-Amyloid Precursor Protein Secretion and Heparin Binding to β-Amyloid Peptide", Journal of Neurochemistry, 1998, vol. 70, No. 2, pp. 736-744.

Molino, M., et al., "Differential Expression of Functional Protease-Activated Receptor-2 (PAR-2) in Human Vascular Smooth Muscle Cells", Arteriosclerosis, Thrombasis, and Vascular Biology, vol. 18, No. 5, 1998, pp. 825-832.

Plescia, J., et al., "Activation of MAC-1 (CD11b/CD18)-Bound Factor X by Release Cathepsin G Defines an Alternative Pathway of Leucocyte Initiation of Coagulation", Biochem. J., 1996, vol. 319, pp. 873-879.

Howells, G. L., et al., "Proteinase-Activated Receptor-2: Expression by Human Neutrophils", Journal of Cell Science, 1997, vol. 110, pp. 881-887.

Herbert, J.-M., et al., "Effector Protease Receptor 1 Mediates the Mitogenic Activity of Factor Xa for Vascular Smooth Muscle Cells in Vitro and In Vivo", J. Clin. Invest., 1998, vol. 101, No. 5, pp. 993-1000.

Donnelly, K. M., et al., "*Ancylostoma caninum* Anticoagulant Peptide Blocks Metastasis In Vivo and Inhibits Factor Xa Binding to Melanoma Cells In Vitro", Thromb Haemost, 1998, vol. 79, pp. 1041-1047.

Ragosta, M., et al., "Specific Factor Xa Inhibition Reduces Restenosis After Balloon Angioplasty of Atherosclerotic Femoral Arteries in Rabbits", Circulation, 1994, vol. 89, No. 3, pp. 1262-1271.

Zhang, Y., et al., "Tissue Factor Controls the Balance of Angiogenic and Antiangiogenic Properties of Tumor Cells in Mice", J. Clin. Invest., 1994, vol. 94, pp. 1320-1327.

Green, D., et al., "Lower Mortality in Cancer Patients Treated with Low-Molecular-Weight Versus Standard Heparin", The Lancet, 1992, vol. 339, p. 1476.

Ko, F. N., et al., "Coagulation Factor Xa Stimulates Platelet-Derived Growth Factor Release and Mitogenesis in Cultured Vascular Smooth Muscle Cells of Rat", J. Clin. Invest., 1996, vol. 98, No. 6, pp. 1493-1501.

Kakkar, A. K., et al., "Antithrombotic Therapy in Cancer", BMJ, 1999, vol. 3318, pp. 1571-1572.

Gasic, G. P., et al., "Coagulation Factors X, Xa, and Protein S as Potent Mitogens of Cultured Aortic Smooth Muscle Cells", Proc. Natl. Acad. Sci. USA, 1992, vol. 89, pp. 2317-2320.

Cirino, G., et al., "Factor Xa as an Interface Between Coagulation and Inflammation: Molecular Mimicry of Factor Xa Association with Effector Cell Protease Receptor-1 Induces Acute Inflammation In Vivo", J. Clin. Invest., 1997, vol. 99, No. 10, pp. 2446-2451.

Senden, N. H. M., et al., "Factor Xa Induces Cytokine Production and Expression of Adhesion Molecules by Human Umbilical Vein Endothelial Cells", The Journal of Immunology, 1998, vol. 161, pp. 4318-4324.

Papapetropoulos, A., et al., "Hypotension and Inflammatory Cytokine Gene Expression Triggered by Factor Xa-Nitric Oxide Signaling", Proc. Natl. Acad. Sci, USA, 1998, vol. 95, pp. 4738-4742.

Camerer, E., et al., "Tissue Factor- and Factor X-dependent Activation of Protease-Activated Receptor 2 by Factor VIIa", PNAS, 2000, vol. 97, No. 10, pp. 5255-5260.

Donovan, F. M., et al., "Thrombin Induces Apoptosis in Cultured Neurons and Astrocytes via a Pathway Requiring Tyrosine Kinase and RhaA Activities", The Journal of Neuroscience, 1997, vol. 17, No. 14, pp. 5316-5326.

Lindner, J. R., et al., "Delayed Onset of Inflammation in Protease-Activated Receptor-2-Deficient Mice", The Journal of Immunology, 2000, pp. 6504-6510.

Bouchard, B. A., et al., "Effector Cell Protease Receptor-1, a Platelet Activation-dependent Membrane Protein, Regulates Prothrombinase-catalyzed Thrombin Generation", The Journal of Biological Chemistry, 1997, vol. 272, No. 14, pp. 9244-9251.

Molino, M., et al., "Endothelial Cell Thrombin Receptors and PAR-2", The Journal of Biological Chemistry, 1997, vol. 272, No. 17, pp. 11133-11141.

Nicholson, A. C., et al., "Effector Cell Protease Receptor-1 Is a Vascular Receptor for Coagulation Factor Xa", The Journal of Biological Chemistry, 1996, vol. 271, No. 45, pp. 28407-28413.

Watson, D. J., et al., "Heparin-Binding Properties of the Amyloidogenic Peptides Aβ and Amylin", The Journal of Biological Chemistry, 1997, vol. 272, No. 50, pp. 31617-31624.

Tuszynski, G. P., et al., "Isolation and Characterization of Antistasin", The Journal of Biological Chemistry, 1987, vol. 262, No. 20, pp. 9718-9723.

Kranzhöfer, R., et al., "Thrombin Potently Stimulates Cytokine Production in Human Vascular Smooth Muscle Cells but Not in Mononuclear Phagocytes", Circulation Research, 1996, vol. 79, No. 2, pp. 286-294.

Schwartz, R. S., et al., "Neointimal Thickening After Severe Coronary Artery Injury is Limited by Short-term Adminstration of a Factor Xa Inhibitor", Circulation, 1996, vol. 93, No. 8, pp. 1542-1548.

Abendschein, D. R., et al., "Inhibition of Thrombin Attenuates Stenosis After Arterial Injury in Minipigs", JACC, 1996, vol. 28, No. 7, pp. 1849-1855.

Carmeliet, P., et al., "Gene Manipulation and Transfer of the Plasinogen and Coagulation System in Mice", Seminars in Thrombosis and Hemostasis, 1996, vol. 22, No. 6, pp. 525-542.

Stouffer, G. A., et al., "The Role of Secondary Growth Factor Production in Thrombin-Induced Proliferation of Vascular Smooth Muscle Cells", Seminars in Thrombosis and Hemostasis, 1998, vol. 24, No. 2, pp. 145-150.

Bevilacqua, M. P., et al., "Inducible Endothelial Functions in Inflammation and Coagulation", Seminars in Thrombosis and Hemostasis, 1987, vol. 13, No. 4, pp. 425-433.

Riedl, B., et al., "Recent Developments with Oxazolidinone Antibiotics", Exp. Opin. Ther. Patents, 1999, vol. 9, No. 5, pp. 625-633.

Barbachyn, M.R., et al., "Identification of Novel Oxazolidinone (U-100480) with Potent Antimycobacterial Activity", J. Med. Chem., 1996, vol. 39, pp. 680-685.

Tucker, J. A., et al, "Piperazinyl Oxazolidinone Antibacterial Agents Containing a Pyridine, Diazene, or Triazene Heteroaromatic Ring", J. Med. Chem. 1998, vol. 41, pp. 3727-3735.

Brickner, S.J., et al., "Synthesis and Antibacterial Activity of U-100592 and U-100766, Two Oxazolidinone Antibacterial Agents for the Potenial treatment of Multidrug-Resistant Gram-Positive Bacterial Infections" J. Med. Chem., 1996, vol. 39, pp. 673-679.

Gregory, W.A., et al., "Antibacterials. Synthesis and Structure-Activity Studies of 3-Aryl-2-oxooxazolidines. 1. The "B" Group", J. Med. Chem., 1989, vol. 32, No. 8, pp. 1673-1681.

Berry, C. N., et al., "Antithrombotic Actions of Argatroban in Rat Models of Venous, 'Mixed' and Arterial Thrombosis, and its Effects on the Tail Transection Bleeding Time", Br. J. Pharmacol., 1994 vol. 113, pp. 1209-1214.

Meng, K., et al., "Effect of Acetylsalicyclic Acid of Experimentally Induced Arterial Thrombosis in Rats", Naunyn-Schmiedeberg's Arch. Pharmacol.,1977, vol. 301, pp. 115-119.

Chern, J.W., et al., "Studies on Quinazolines IX:[1] Fluorination Versus 1,2-Migration on the Reaction of 1,3-Bifunctionalized Amino-2-Propanol with DAST", Tetrahedron Lett., 1998, vol. 39, pp. 8483-8486.

Shakespeare, W. C., et al., "Palladium-Catalyzed Coupling of Lactams with Bromobenzenes", Tetrahedron Lett., 1999, vol. 40, pp. 2035*2038.

Renger, B., et al., "Direkte N-Arylierung von Amiden: Eine Verbesserung der Goldberg-Reaktion", Synthesis, 1985, pp. 856-860.

Aebischer, E., et al., "Synthesis of N-Arylrolipram Derivatives—Potent and Selective Phosphodiesterase-IV Inhibitors—by Copper Catalyzed Lactam-Aryl Halide Coupling", Hetercycles, 1998, vol. 48, No. 11, pp. 2225-2229.

Pfeil, E., et al., "β-Aminoäthylierung von Indol und 2-methylindol", Angew Chem., 1967, vol. 79, No. 4, pp. 188-189.

Ziegler C. B., at al., "Synthesis of Some Novel 7-Substituted Quinolonecarboxylic Acids via Nitroso and Nitrone Cycloadditions", J. Hetercycl. Chem., 1988, vol. 25, No. 2, pp. 719-723.

Bartoli, G., et al, "Electronic and Steric Effects in Nucleophilic Aromatic Substitution. Reaction by Phenoxides as Nucleophiles in Dimethyl Sulfoxide", J. Org. Chem., 1975, vol. 40, No. 7, pp. 872-874.

Reppe, et al., "N-p-Merthoxyphenyl-pyrrolidon", Justus Liebigs Ann. Chem., 1955 vol. 596, p. 208.

Luvalle, J.E., et al., "Oxidation Processes. XXI.[1] The Autoxidation of the p-Phenylenediamines", J. Am. Chem. Soc., 1948, vol. 70, pp. 2223-2233.

Snyder, H.R., et al., "Imidazo[4,5f]quinolines III: Antibacterial 7-Methyl-9-(substituted Arylamino)imidazo[4,5-f]quinolines", J. Pharm. Sci., 1977, vol. 66, pp. 1204-1406.

Adams, R., et al., "Sulfanilamide Derivatives. I", J. Am. Chem. Soc. 1939, vol. 61, pp. 2342-2349.

Khanna, I.K. , et al., "1,2-Diarylpyrroles as Potent and Selective Inhibitors of Cyclooxygenase-2", J. Med. Chem., 1997, vol. 40, pp. 1619-1633.

Gutcait, A., et al., "Studies on Quinazolines. 6.[1] Asymmetric Synthesis of (S)-(+)- and (R)-(−)-3-[[4-(2-Methoxyphenyl)piperazin-1-yl]methylthio-2,3,-dihydromidazo[1,2-c]quinazolines", Tetrahedron Asym., 1996, vol. 7, No. 6, pp. 1641-1648.

Grell, W., et al., "Repaglinide and Related Hypoglycemic Benzoic Acid Derivatives", J. Med. Chem., 1998, vol. 41, pp. 5219-5246.

Artico, M. et al., "Rsearch on Compounds with Antiblastic Activity", Farmaco Ed. Sci. 1969, vol. 24, pp. 179-190.

Dankwardt, S. M., at al, "Nonpeptide Bradykinin Antagonist Analogs based on a Model of a Sterling-Winthrop Nonpeptide Bradykinin Antagonist Overlapped with Cyclic Hexapeptide Bradykinin Antagonist Peptides", Bioorg. Med. Chem. Lett., 1997, vol. 7, No. 14, pp. 1921-1926.

Reppe, et al., "N-6-Aminohexyl-pyrrolidon", Justus Liebigs Ann. Chem. 1955, vol. 596, pp. 204.

Bouchet, P., et al., "σ Values of N-Substitutes Azoles", J. Chem. Soc. Perkin Trans., 1974, vol. 2, pp. 449-451.

Surrey, A. R., et al., "The Preparation of N-Benzyl-3-Morpholones and N-Benzyl-3-Homomorpholones from N-(Hydroxyalkyl)-chloroacetamides" J. Amer. Chem. Soc., 1955, vol. 77, pp. 633-636.

Tong, L.K.J., et al., "The Mechanism of Dye Formation in Color Photography. VII. Intermediate Bases in the Deamination of Quinonediimines" J. Amer. Chem. Soc. 1960, vol. 82, 1988-2001.

Delande, S.A., "Heterocycles", Chemical. Abstracts, American Chemical Society, 1979, vol. 90, pp. 663.

Bots, M., et al., Coagulation and Fibrinolysis Markers and Risk of Dementia, Haemostasis, vol. 28 (1998); pp. 216-222.

Benzakour, O., et al., "Cellular and molecular events in atherogenesis; basis for pharmocological and gene therapy approaches to stenosis," Cellular Pharmacology, 1996, vol. 3, pp. 7-22.

Kanthou, C., et al., "Cellular effects of thrombin and their signalling pathways," Cellular Pharmacology, vol. 2 (1995); pp. 293-302.

Kaiser, B., et al., "Antiproliferation Action of Factor Xa Inhibitors in a Rat Model of Chronic Restenosis," Abstracts of the XVIIth Congress of the International Society on Thrombosis and Haemostasis, Aug. 1999, p. 144.

Tyrrell, D., et al., "Heparin in Inflammation: Potential Therapeutic Applications Beyond Anticoagulation," Advances in Pharmacology, vol. 46 (1999); pp. 151-208.

Smirova, I., et al., "Thrombin Is an Extracellular Signal that Activates Intracellular Death Protease Pathways Inducing Apoptosis in Model Motor Neurons," J. Neurobiology, vol. 36 (1998); pp. 64-80.

Bono, F., et al., "Factor Xa Activates Endothelial Cells by a Receptor Cascade Between EPR-1 and PAR-2," Arterioscler Thromb Vasc Biol., Nov. 2000; pp. 1-6.

Lala, P. et al, "Role of Nitric Oxide in tumor progression: Lessons Learned from Experimental Tumors, " Cancer and Metastasis Review, vol. 17, pp. 91-106 (1998).

Golub, T., et al., *Molecular Classification of Cancer Science* (1999), vol. 286, 531-537.

FDA mulls drug to slow late-stage Alzheimer's [online], [retrieved on Sep. 23, 2003]. Retrieved from the internet, URL:http://www.cnn.com/2003/HEALTH/conditions/09/24/alzheimers.drug.ap/index.html>.

Ulllman's Encyclopedia of Industrial Chemistry, Fifth Revised Ed., Editors: Elvers, B., Hawkins, S., VCH Verlagsgesellschaft mbH, Weinheim, 19985-1996, Ch. 5, 488-506.

Zhu, B., Scarborough , R., "Recent Advances in Inhibitors of Factor Xa in the Prothrombinase Complex," *Curr. Opinions Card. Pul. Ren. Inv. Drugs*, 1:63-87 (1999).

Uzan, A., "Antithrombotic Agents," *Emerging Drugs: The Prospect for Improved Medicines*, 3: 189-208 1998.

Kaiser, B., "Thrombin and Factor Xa Inhibitors," *Drugs of the Future*, 23: 423-426 (1998).

Al-Obeidi, F., Ostrem, J., "Factor Xa Inhibitors," *Expert Opin. Therapeutic Patents*, 9: 931-953 (1999).

Al-Obeidi, F., Ostrem, J., "Factor Xa Inhibitors by Classical and Combinatorial Chemistry," *DDT*, 3: 223-231 (May 1998).

Hauptmann, J.,et al., "Synthetic Inhibitors of Thrombin and Factor Xa: From Bench to Bedside," *Thrombosis Research*, 93: 203-241 (1999).

Pschyrembel, Klinisches Worterbuch, 257. Auflage, 1994, Walter de Gruyter Verlag, p. 199-200, Stichwort "Biutgerinnung."

Rompp Lexikon Chemie, Ver. 1.5, 1998, Georg Thieme Verlag Stuttgart, Stichwort "Blutgerrinung" Lubert Stryer, Biochemie, Spektrum der Wissenschaft Verlagsgesellschaft mbH Heidelberg, 1990, p. 259.

Pschyrembel, Klinisches Worterbuch, 257. Auflage, 1994, Walter de Gruyter Verlag, p. 610, Stichwort "Heparin."

Rompp Lexikon Chemie, Ver. 1.5, 1998, Georg Thieme Verlag Stuttgart, Stichwort "Heparin."

Pschyrembei, Klinisches Worterbuch, 257. Auflage, 1994, Walter de Gruyter Verlag, p. 292, Stichwort "Cumarinderivate."

Becker, M.R., et al., "Synthesis, Sar and in Vivo Activity of Novel Thienopyridine Sulfonamide Pyrrolidininones as Factor Xa Inhibitors," *Bioorganic and Medicinal Chemistry Letters*, 9: 2753-2758 (1999).

Linder, J., et al., "Delayed Onset of Inflammation in Protease-Activated Receptor-2-Deficient Mice," J. Immunology, 2000, pp. 6504-6510.

Cirino, G. et al. Inflammation-Coagulation Network: Are Serine Protease receptors the knot?; Tips; vol. 21, pp. 170-172, (2000) .

Dostert et al., "5 Hydroxymethyk—2—Ox Azolidihones," *Chem. Abstr*, 1979, vol. 90, pp. 186926.

Perzborn, E. et al. In vitro and in vivo studies of the novel antithrombotic agent BAY 59-7939-an oral, direct Factor Xa inhibitor. Journal of Thrombosis and Haemostasis 3, 3, Mar. 2005, pp. 514-521.

Espinosa, G. et al. Thrombotic microangiopathic haemolytic anaemia and antiphospholipid antibodies. Annals of the Rheumatic Diseases, 63, 6, Jun. 2004, pp. 730-736.

Bonomini, V. et al. A New Antithrombotic Agent in the Treatment of Acute Renal Failure Due to Hemolytic-Uremic Syndrome and Thrombotic Thrombocytopenic Purpura. Nephron 37, 1984, 2, 144.

Sinha, U. et al. Antithrombotic and hemostatic capacity of factor Xa versus thrombin inhibitors in models of venous and arteriovenous thrombosis. European Journal of Pharmacology 2000, 395, 51-59.

Betz, A. Recent advances in Factor Xa inhibitors. Expert Opinion Ther. Patents 2001, 11, 1007-1017.

Tan, K.T. et al. Factor X inhibitors. Expert Opinion Investig. Drugs 2003, 12, 799-804.

Ruef, J. et al. New antithrombotic drugs on the horizon. Expert Opinion Investig. Drugs 2003, 12, 781-797.

Samama, M.L. Synthetic direct and indirect factor Xa inhibitors. Thromobis Research 2002, 106, V267-V273.

Quan, M.L. The race to an orally active Factor Xa inhibitor: Recent advances. Current Opinion in Drug Discovery & Development 2004, 7, 460-469.

The Ephesus Study, Blood 2000, 96, 490a.

The Penthifra Study, Blood 2000, 96, 490a.

The Pentamaks Study, Blood 2000, 96, 490a-491a.

The Pentathlon 2000 Study, Blood 2000, 96, 491a.

Leadley, R.J. Coagulation Factor Xa Inhibition: Biological Background and Rationale. Current Topics in Medical Chemistry 2001, 1, 151-159.

Roehrig, S. et al. Discovery of the Novel Antithrombotic Agent 5-Chloro-N-({(5S)-2-oxo-3-[4-(3-oxomorpholin-4-yl)phenyl]-1,3-oxazolidin-5-yl}methyl)thiophene-2-carboxamide (BAY 59-7939): An Oral, Direct Factor Xa Inhibitor. J. Med. Chem. 48, 22. Sep. 2005, pp. 5900-5908.

Caira, M. Crystalline Polymorphism Of Organic Compounds. Springer Verlag Berlin Heidelberg 198, 1998, pp. 163-208.

Hancock, B. et al. Characteristics and Significance of the Amorphous State in Pharmaceutical Systems. Journal of Pharmaceutical Science. 86, 1 (Jan. 1997), pp. 1-12.

Chiou, W.L. et al. Pharmaceutical Applications of Solid Dispersion Systems. Journal of Pharmaceutical Sciences 60, (1971). 128-1302.

Ford, J.L. The Current Status of Solid Dispersions. Pharm Acta Helv. 61, (1986)69-88.

Rasenack, N. et al. Poorly Water-soluble Drugs for Oral Delivery—A Challenge for Pharmaceutical Development. Pharmazeutische Industrie 67, Nr. 5 (2005), 583-591.

Breitenbach, J. Melt extrusion: from process to drug delivery technology. European Journal of Pharmaceutics and Biopharmaceutics 54 (2002) 107-117.

Breitenbach, J. Feste Loesungen durch Schmelzextrusion—ein integriertes Herstellkonzept. Pharmazie in unserer Zeit 29 (2000), 46-49.

Gilligan, D.M. et al. The Management of Atrial Fibrillation. The American Journal of Medicine, vol. 101, (4) 1996, 413-421.

Kubitza, D. et al. Novel factor Xa inhibitors for prevention and treatment of thromboembolic diseases. Expert Opinion on Investig. Drugs, vol. 15, (8) 2006, pp. 843-855.

Williams, E.M. Vaughan. Classificating anti-arrhythimic drugs. In: Cardiac Arrythias—Proceedings of a symposium, sandoe E., soedertaeje: Astra (1970), pp. 449-469.

http://familydoctor.org/online/famdocen/home/common/heartdisease/basics/290.html, (2008).

Kubitza, et al., Multiple dose escalation study Investigating the pharmacodyanamics, safety, and pharmacokinetics of BAY 59/7939 an oral, direct Factor Xa inhibitor in healthy male subjects, Blood, vol. 102:11:Nov. 16, 2003, p. 811a.

Kubitza, et al., Abstract 3010, Single dose escalation study investigating the pharmacodyanamlcs, safety, and pharmacokinetics of BAY 59/7939 an oral, direct Factor Xa inhibitor in healthy male subjects, Blood, vol. 102:11. Nov. 16, 2003, p. 813a.

Lerk et al. Effect of Hydrophilization Drugs on Release Rat from Capsules, J. of Pharma. Sciences, 67(7), pp. 935-939 (1978).

Lerk, et al., In Vitro and In Vivo Availability of Hydrophilized Phenytoin from Capsules, J. of Pharma. Sciences, 68(5), pp. 634-638 (1979).

Greaves, et al., Novel Approaches to the Preparation of Low-Dose Solid Dosage Forms, Pharmaceutical Technology. January, pp. 60-64, (1995).

Reppe, et al., Justus Liebigs Ann. Chem. 596, 1955, p. 209.

[Database Bielstein] Bielstein Institute for Organic Chemistry, Frankfurt-Main, DE. Database Accession No. 8822985, (2005).

"Enzilkopedia Lekarstv", Registr lekarstvennych sredstv Rossii, pod. red. Krylova, J.F., Moskau, 2000, p. 442.

M.D. Maschkovski, "Lekarstvennye sredstva", 1993, Moscow, Verl. Medizina, Part 1, p. 6.

V.G. Belikov, "Farmazevti'cheskaya chimia", Moskau, Verl. Vysschaya schkola, 1993, p. 43-47.

* cited by examiner

SUBSTITUTED OXAZOLIDINONES FOR COMBINATIONAL THERAPY

The present invention relates to combinations of A) oxazolidinones of the formula (I) with B) other active ingredients, to a process for producing these combinations and to the use thereof as medicaments, in particular for the prophylaxis and/or treatment of thromboembolic disorders.

Oxazolidinones of the formula (I) act in particular as selective inhibitors of coagulation factor Xa and as anticoagulants.

It has been possible to demonstrate an antithrombotic effect of factor Xa inhibitors in numerous animal models (cf. WO 99/37304; WO 99/06371; J. Hauptmann, J. Stürzebecher, Thrombosis Research 1999, 93, 203; F. Al-Obeidi, J. A. Ostrem, Factor Xa inhibitors, Exp. Opin. Ther. Patents 1999, 9, 931; B.-Y. Zhu, R. M. Scarborough, Curr. Opin. Card. Pulm. Ren. Inv. Drugs 1999, 1 (1), 63, M. Samama, J. M. Walenga, B. Kaiser, J. Fareed, Specific Factor Xa Inhibitors, Cardiovascular Thrombosis: Thrombocardiology and Thromboneurology, Second Edition, edited by M. Verstraete, V. Fuster, E. J. Topol, Lippincott-Raven Publishers, Philadelphia 1998) and clinical studies on patients (The Ephesus Study, blood, Vol 96, 490a, 2000; The Penthifra Study, blood, Vol 96, 490a, 2000; The Pentamaks Study, blood, Vol 96, 490a-491a, 2000; The Pentathlon 2000 Study, blood, Vol 96, 491a, 2000). Factor Xa inhibitors can therefore be employed preferably in medicaments for the prophylaxis and/or treatment of thromboembolic disorders.

Thromboembolic vascular disorders are the commonest cause of morbidity and mortality in industrialized countries (Thiemes Innere Medizin, Georg Thieme Verlag Stuttgart, New York; American Heart Association, 2000 heart and stroke statistical update, Dallas, Tex.: American Heart Association, 2000). Anticoagulant therapy has proved effective in the treatment of vascular disorders in order to prevent thrombotic vascular occlusions and to reopen thrombotically occluded vessels, and has great importance in the prophylaxis and treatment of coronary, peripheral and cerebral vascular disorders, and in the prophylaxis and/or treatment of venous thromboses and pulmonary embolisms.

Thromboembolic complications may be caused by atherosclerotic lesions of the vessel wall, especially disturbance of endothelial function, which may lead to acute thrombotic occlusions. Atherosclerosis is a multifactorial disorder which depends on a large number of cardiovascular risk factors. Clinical studies have shown that prophylaxis with anticoagulants does not definitively influence the course of the arterial vascular disorder. Targeted treatment of the risk factors in conjunction with an antithrombotic therapy is therefore advantageous.

Risk factors for coronary, peripheral and cerebral vascular disorders are, for example: elevated serum cholesterol levels, arterial hypertension, cigarette smoking, diabetes mellitus (Allgemeine und spetargetle Pharmacologie und Toxikologie, W. Forth, D. Henschler, W. Rummel, K. Starke; Spektrum Akademischer Verlag Heidelberg Berlin Oxford; Thiemes Innere Medizin, Georg Thieme Verlag Stuttgart, New York). The principles of preventive medicine are based on elimination of these risk factors. Besides a change in lifestyle, also included are pharmacological measures such as, for example, antihypertensive therapy, lipid-lowering medicaments or thrombosis prophylaxis. In addition, combination with coronary therapeutic agents is suitable for the treatment where there is pre-existent coronary heart disease.

It has now been found, surprisingly, that combinations of oxazolidinones of the formula (I) with certain other active ingredients have interesting properties and are more suitable for the prophylaxis and/or treatment of various diseases than the individual active ingredients alone.

The invention therefore relates to combinations of
A) oxazolidinones of the formula (I) with
B) other active ingredients, in particular with platelet aggregation inhibitors, anticoagulants, fibrinolytics, lipid-lowering agents, coronary therapeutic agents and/or vasodilatators.

"Combinations" mean for the purposes of the invention not only dosage forms which comprise all the components (so-called fixed combinations), and combination packs which comprise the components separate from one another, but also components administered simultaneously or sequentially as long as they are employed for the prophylaxis and/or treatment of the same disease. It is likewise possible to combine two or more active ingredients together, and thus the combinations in this connection are in each case double or multiple.

Suitable oxazolidinones of the combination of the invention include, for example, compounds of the formula (I)

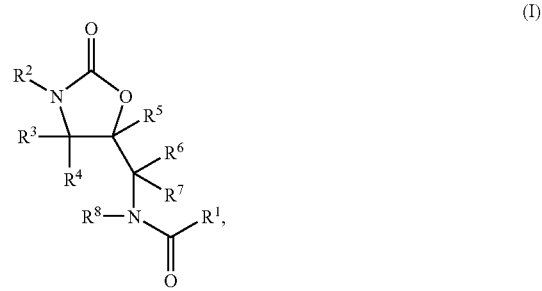

(I)

in which:
$R^1$ is optionally benzo-fused thiophene (thienyl) which may optionally be substituted one or more times;
$R^2$ is any organic radical;
$R^3$, $R^4$, $R^5$, $R^6$, $R^7$ and $R^8$ are identical or different and are hydrogen or $(C_1-C_6)$-alkyl, and the pharmaceutically acceptable salts, hydrates and prodrugs thereof.

Preference is given in this connection to compounds of the formula (I) in which
$R^1$ is optionally benzo-fused thiophene (thienyl) which may optionally be substituted one or more times by a radical from the group of halogen; cyano; nitro; amino; aminomethyl; $(C_1-C_8)$-alkyl which may in turn be optionally substituted one or more times by halogen; $(C_3-C_7)$-cycloalkyl; $(C_1-C_8)$-alkoxy; imidazolinyl; —C(=NH)NH$_2$; carbamoyl; and mono- and di-$(C_1-C_4)$-alkylaminocarbonyl,
$R^2$ is one of the following groups:
A-,
A-M-,
D-M-A-,
B-M-A-,
B-,
B-M-,
B-M-B-,
D-M-B-,
where:
the radical "A" is $(C_6-C_{14})$-aryl, preferably $(C_6-C_{10})$-aryl, in particular phenyl or naphthyl, very particularly preferably phenyl;
the radical "B" is a 5- or 6-membered aromatic heterocycle which comprises up to 3 heteroatoms and/or hetero chain members, in particular up to 2 heteroatoms and/or hetero chain members, from the series S, N, NO (N-oxide) and O;

the radical "D" is a saturated or partially unsaturated, mono- or bicyclic, optionally benzo-fused 4- to 9-membered heterocycle which comprises up to three heteroatoms and/or hetero chain members from the series S, SO, $SO_2$, N, NO (N-oxide) and O;

the radical "M" is —NH—, —$CH_2$—, —$CH_2CH_2$—, —O—, —NH—$CH_2$—, —$CH_2$—NH—, —$OCH_2$—, —$CH_2O$—, —CONH—, —NHCO—, —COO—, —OOC—, —S—, —$SO_2$— or a covalent bond;

where the groups "A", "B" and "D" defined above may in each case optionally be substituted one or more times by a radical from the group of halogen; trifluoromethyl; oxo; cyano; nitro; carbamoyl; pyridyl; ($C_1$-$C_6$)alkanoyl; ($C_3$-$C_7$)-cycloalkanoyl; ($C_6$-$C_{14}$)-arylcarbonyl; ($C_5$-$C_{10}$)-heteroarylcarbonyl; ($C_1$-$C_6$)-alkanoyloxymethyloxy; ($C_1$-$C_4$)-hydroxyalkylcarbonyl; —$COOR^{27}$; —$SO_2R^{27}$; —$C(NR^{27}R^{28})$=$NR^{29}$; —$CONR^{28}R^{29}$; —$SO_2NR^{28}R^{29}$; —$OR^{30}$; —$NR^{30}R^{31}$, ($C_1$-$C_6$)-alkyl and ($C_3$-$C_7$)-cycloalkyl, where ($C_1$-$C_6$)-alkyl and ($C_3$-$C_7$)-cycloalkyl in turn may optionally be substituted by a radical from the group of cyano; —$OR^{27}$; —$NR^{28}R^{29}$; —$CO(NH)_v(NR^{27}R^{28})$ and —$C(NR^{27}R^{28})$=$NR^{29}$, where:

v is either 0 or 1 and $R^{27}$, $R^{28}$ and $R^{29}$ are identical or different and are, independently of one another, hydrogen, ($C_1$-$C_4$)-alkyl, ($C_3$-$C_7$)-cycloalkyl, ($C_1$-$C_4$)-alkanoyl, carbamoyl, trifluoromethyl, phenyl or pyridyl, and/or $R^{27}$ and $R^{28}$, or $R^{27}$ and $R^{29}$, form together with a nitrogen atom to which they are bonded a saturated or partially unsaturated 5- to 7-membered heterocycle having up to three, preferably up to two, identical or different heteroatom's from the group of N, O and S, and $R^{30}$ and $R^{31}$ are identical or different and are, independently of one another, hydrogen, ($C_1$-$C_4$)-alkyl, ($C_3$-$C_7$)-cycloalkyl, ($C_1$-$C_4$)-alkylsulfonyl, ($C_1$-$C_4$)-hydroxyalkyl, ($C_1$-$C_4$)-aminoalkyl, di-($C_1$-$C_4$)-alkylamino-($C_1$-$C_4$)-alkyl, —$CH_2C(NR^{27}R^{28})$=$NR^{29}$ or —$COR^{33}$, where $R^{33}$ is ($C_1$-$C_6$)-alkoxy, ($C_1$-$C_4$)-alkoxy-($C_1$-$C_4$)-alkyl, ($C_1$-$C_4$)-alkoxycarbonyl-($C_1$-$C_4$)-alkyl, ($C_1$-$C_4$)-aminoalkyl, ($C_1$-$C_4$)-alkoxycarbonyl, ($C_1$-$C_4$)-alkanoyl-($C_1$-$C_4$)-alkyl, ($C_3$-$C_7$)-cycloalkyl, ($C_2$-$C_6$)-alkenyl, ($C_1$-$C_8$)-alkyl which may optionally be substituted by phenyl or acetyl, or is ($C_6$-$C_{14}$)-aryl, ($C_5$-$C_{10}$)-heteroaryl, trifluoromethyl, tetrahydrofuranyl or butyrolactone, $R^3$, $R^4$, $R^5$, $R^6$, $R^7$ and $R^8$ are identical or different and are hydrogen or ($C_1$-$C_6$)-alkyl, and the pharmaceutically acceptable salts, hydrates and prodrugs thereof.

Preference is likewise given in this connection to compounds of the general formula (I)

in which $R^1$ is thiophene (thienyl), in particular 2-thiophene, which may optionally be substituted one or more times by halogen, preferably chlorine or bromine, amino, aminomethyl or ($C_1$-$C_8$)-alkyl, preferably methyl, where the ($C_1$-$C_8$)-alkyl radical may optionally in turn be substituted one or more times by halogen, preferably fluorine, $R^2$ is one of the following groups:

A-,
A-M-,
D-M-A-,
B-M-A-,
B-,
B-M-,
B-M-B-,
D-M-B-, where:

the radical "A" is ($C_6$-$C_{14}$)-aryl, preferably ($C_6$-$C_{10}$)-aryl, in particular phenyl or naphthyl, very particularly preferably phenyl;

the radical "B" is a 5- or 6-membered aromatic heterocycle which comprises up to 3 heteroatoms and/or hetero chain members, in particular up to 2 heteroatoms and/or hetero chain members, from the series S, N, NO (N-oxide) and O;

the radical "D" is a saturated or partially unsaturated 4- to 7-membered heterocycle which comprises up to three heteroatoms and/or hetero chain members from the series S, SO, $SO_2$, N, NO (N-oxide) and O;

the radical "M" is —NH—, —$CH_2$—, —$CH_2CH_2$—, —O—, —NH—$CH_2$—, —$CH_2$—NH—, —$OCH_2$—, —$CH_2O$—, —CONH—, —NHCO—, —COO—, —OOC—, —S— or a covalent bond;

where the groups "A", "B" and "D" defined above may in each case optionally be substituted one or more times by a radical from the group of halogen; trifluoromethyl; oxo; cyano; nitro; carbamoyl; pyridyl; ($C_1$-$C_6$)-alkanoyl; ($C_3$-$C_7$)-cycloalkanoyl; ($C_6$-$C_{14}$)-arylcarbonyl; ($C_5$-$C_{10}$)-heteroarylcarbonyl; ($C_1$-$C_6$)-alkanoyloxymethyloxy; —$COOR^{27}$; —$SO_2R^{27}$; —$C(NR^{27}R^{28})$=$NR^{29}$; —$CONR^{28}R^{29}$; —$SO_2NR^{28}R^{29}$; —$OR^{30}$; —$NR^{30}R^{31}$, ($C_1$-$C_6$)-alkyl and ($C_3$-$C_7$)-cycloalkyl, where ($C_1$-$C_6$)-alkyl and ($C_3$-$C_7$)-cycloalkyl may in turn optionally be substituted by a radical from the group of cyano; —$OR^{27}$; —$NR^{28}R^{29}$; —$CO(NH)_v(N^{27}R^{28})$ and —$C(NR^{27}R^{28})$=$NR^{29}$, where:

v is either 0 or 1, and $R^{27}$, $R^{28}$ and $R^{29}$ are identical or different and are, independently of one another, hydrogen, ($C_1$-$C_4$)-alkyl or ($C_3$-$C_7$)-cycloalkyl, and/or $R^{27}$ and $R^{28}$, or $R^{27}$ and $R^{29}$, form together with the nitrogen atom to which they are bonded a saturated or partially unsaturated 5- to 7-membered heterocycle having up, to three, preferably up to two, identical or different heteroatoms from the group of N, O and S, and $R^{30}$ and $R^{31}$ are identical or different and are, independently of one another, hydrogen, ($C_1$-$C_4$)-alkyl, ($C_3$-$C_7$)-cycloalkyl, ($C_1$-$C_4$)-alkylsulfonyl, ($C_1$-$C_4$)-hydroxyalkyl, ($C_1$-$C_4$)-aminoalkyl, di-($C_1$-$C_4$)-alkylamino-($C_1$-$C_4$)-alkyl, ($C_1$-$C_4$)-alkanoyl, ($C_6$-$C_{14}$)-arylcarbonyl, ($C_5$-$C_{10}$)-heteroarylcarbonyl, ($C_1$-$C_4$)-alkylaminocarbonyl or —$CH_2C(NR^{27}R^{28})$=$NR^{29}$, $R^3$, $R^4$, $R^5$, $R^6$, $R^7$ and $R^8$ are identical or different and are hydrogen or ($C_1$-$C_6$)-alkyl, and the pharmaceutically acceptable salts, hydrates and prodrugs thereof.

Particular preference is given in this connection to compounds of the general formula (I)

in which $R^1$ is thiophene (thienyl), in particular 2-thiophene, which may optionally be substituted one or more times by halogen, preferably chlorine or bromine, or $(C_1-C_8)$-alkyl, preferably methyl, where the $(C_1-C_8)$-alkyl radical may in turn optionally be substituted one or more times by halogen, preferably fluorine, $R^2$ is one of the following groups:
  A-,
  A-M-,
  D-M-A-,
  B-M-A-,
  B-,
  B-M-,
  B-M-B-,
  D-M-B-,
  where:
  the radical "A" is phenyl or naphthyl, in particular phenyl;
  the radical "B" is a 5- or 6-membered aromatic heterocycle which comprises up to 2 heteroatoms from the series S, N, NO (N-oxide) and O;
  the radical "D" is a saturated or partially unsaturated 5- or 6-membered heterocycle which comprises up to two heteroatoms and/or hetero chain members from the series S, SO, $SO_2$, N, NO (N-oxide) and O;
  the radical "M" is —NH—, —O—, —NH—$CH_2$—, —$CH_2$—NH—, —$OCH_2$—, —$CH_2O$—, —CONH—, —NHCO— or a covalent bond;
  where
  the groups "A", "B" and "D" defined above may in each case optionally be substituted one or more times by a radical from the group of halogen; trifluoromethyl; oxo; cyano; pyridyl; $(C_1-C_3)$-alkanoyl; $(C_6-C_{10})$-arylcarbonyl; $(C_5-C_6)$-heteroarylcarbonyl; $(C_1-C_3)$-alkanoyloxymethyloxy; —$C(NR^{27}R^{28})$=$NR^{29}$; —$CONR^{28}R^{29}$; —$SO_2NR^{28}R^{29}$; —OH; —$NR^{30}R^{31}$; $(C_1-C_4)$-alkyl; and cyclopropyl, cyclopentyl or cyclohexyl,
  where $(C_1-C_4)$-alkyl and cyclopropyl, cyclopentyl or cyclohexyl may in turn optionally be substituted by a radical from the group of cyano; —OH; —$OCH_3$; —$NR^{28}R^{29}$; —$CO(NH)_v(NR^{27}R^{28})$ and —$C(NR^{27}R^{28})$=$NR^{29}$,
  where:
  v is either 0 or 1, preferably 0, and
  $R^{27}$, $R^{28}$ and $R^{29}$ are identical or different and are, independently of one another, hydrogen, $(C_1-C_4)$-alkyl or else cyclopropyl, cyclopentyl or cyclohexyl, and/or
  $R^{27}$ and $R^{28}$, or $R^{27}$ and $R^{29}$, may form together with the nitrogen atom to which they are bonded a saturated or partially unsaturated 5- to 7-membered heterocycle having up to two identical or different heteroatoms from the group of N, O and S, and
  $R^{30}$ and $R^{31}$ are identical or different and are, independently of one another, hydrogen, $(C_1-C_4)$-alkyl, cyclopropyl, cyclopentyl, cyclohexyl, $(C_1-C_4)$-alkylsulfonyl, $(C_1-C_4)$-hydroxyalkyl, $(C_1-C_4)$-aminoalkyl, di-$(C_1-C_4)$-alkylamino-$(C_1-C_4)$-alkyl, $(C_1-C_3)$-alkanoyl or phenylcarbonyl,
$R^3$, $R^4$, $R^5$, $R^6$, $R^7$ and $R^8$ are identical or different and are hydrogen or $(C_1-C_6)$-alkyl, and the pharmaceutically acceptable salts, hydrates and prodrugs thereof.

Especial preference is given in this connection to compounds of the general formula (I)

in which $R^1$ is 2-thiophene which may optionally be substituted in position 5 by a radical from the group chlorine, bromine, methyl or trifluoromethyl, $R^2$ is one of the following groups:
  A-,
  A-M-,
  D-M-A-,
  B-M-A-,
  B-,
  B-M-,
  B-M-B-,
  D-M-B-,
  where:
  the radical "A" is phenyl or naphthyl, in particular phenyl;
  the radical "B" is a 5- or 6-membered aromatic heterocycle which comprises up to 2 heteroatoms from the series S, N, NO (N-oxide) and O;
  the radical "D" is a saturated or partially unsaturated 5- or 6-membered heterocycle which comprises a nitrogen atom and optionally a further heteroatom and/or hetero chain member from the series S, SO, $SO_2$ and O, or up to two heteroatoms and/or hetero chain members from the series S, SO, $SO_2$ and O;
  the radical "M" is —NH—, —O—, —NH—$CH_2$—, —$CH_2$—NH—, —$OCH_2$—, —$CH_2O$—, —CONH—, —NHCO— or a covalent bond;
  where
  the groups "A", "B" and "D" defined above may in each case optionally be substituted one or more times by a radical from the group of halogen; trifluoromethyl; oxo; cyano; pyridyl; $(C_1-C_3)$-alkanoyl; $(C_6-C_{10})$-arylcarbonyl; $(C_5-C_6)$-heteroarylcarbonyl; $(C_1-C_3)$-alkanoyloxymethyloxy; —$CONR^{28}R^{29}$; —$SO_2NR^{28}R^{29}$; —OH; —$NR^{30}R^{31}$; $(C_1-C_4)$-alkyl; and cyclopropyl, cyclopentyl or cyclohexyl,
  where $(C_1-C_4)$-alkyl and cyclopropyl, cyclopentyl or cyclohexyl may in turn optionally be substituted by a radical from the group of cyano; —OH; —$OCH_3$; —$NR^{28}R^{29}$; —$CO(NH)_v(NR^{27}R^{28})$ and —$C(NR^{27}R^{28})$=$NR^{29}$,
  where:
  v is either 0 or 1, preferably 0, and
  $R^{27}$, $R^{28}$ and $R^{29}$ are identical or different and are, independently of one another, hydrogen, $(C_1-C_4)$-alkyl or else cyclopropyl, cyclopentyl or cyclohexyl, and/or
  $R^{27}$ and $R^{28}$, or $R^{27}$ and $R^{29}$, may form together with the nitrogen atom to which they are bonded a saturated or partially unsaturated 5- to 7-membered heterocycle having up to two identical or different heteroatoms from the group of N, O and S, and
  $R^{30}$ and $R^{31}$ are identical or different and are, independently of one another, hydrogen, $(C_1-C_4)$-alkyl, cyclopropyl, cyclopentyl, cyclohexyl, $(C_1-C_4)$-alkylsulfonyl, $(C_1-C_4)$-hydroxyalkyl, $(C_1-C_4)$-aminoalkyl, di-$(C_1-C_4)$-alkylamino-$(C_1-C_4)$-alkyl, $(C_1-C_3)$-alkanoyl or phenylcarbonyl,
$R^3$, $R^4$, $R^5$, $R^6$, $R^7$ and $R^8$ are identical or different and are hydrogen or $(C_1-C_4)$-alkyl, and the pharmaceutically acceptable salts, hydrates and prodrugs thereof.

Very particular preference is given in this connection to compounds of the general formula (I)

in which
$R^1$ is 2-thiophene which is substituted in position 5 by a radical from the group of chlorine, bromine, methyl or trifluoromethyl,
$R^2$ is D-A-:
  where:
    the radical "A" is phenylene;
    the radical "D" is a saturated 5- or 6-membered heterocycle which is linked via a nitrogen atom to "A",
    which has a carbonyl group in direct vicinity to the linking nitrogen atom, and in which a ring carbon member may be replaced by a heteroatom from the series S, N and O;
  where
    the group "A" defined above may optionally be substituted once or twice in the meta position relative to the linkage to the oxazolidinone by a radical from the group of fluorine, chlorine, nitro, amino, trifluoromethyl, methyl or cyano,
$R^3$, $R^4$, $R^5$, $R^6$, $R^7$ and $R^8$ are hydrogen, and the pharmaceutically acceptable salts, hydrates and prodrugs thereof.

Very particular preference is likewise given in this connection to the compound having the following formula

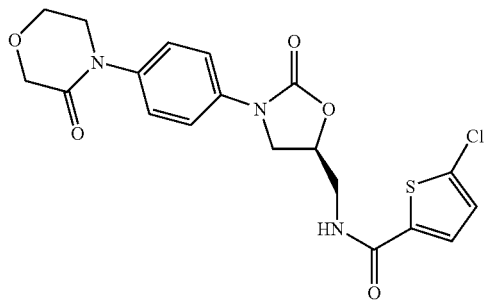

and the pharmaceutically acceptable salts, hydrates and prodrugs thereof.

To date, oxazolidinones have been described essentially only as antibiotics, and in a few cases also as MAO inhibitors and fibrinogen antagonists (Review: Riedl, B., Endermann, R., Exp. Opin. Ther. Patents 1999, 9 (5), 625), and a small 5-[acylaminomethyl] group (preferably 5-[acetylaminomethyl]) appears to be essential for the antibacterial effect.

Substituted aryl- and heteroarylphenyloxazolidinones in which a monosubstituted or polysubstituted phenyl radical may be bonded to the N atom of the oxazolidinone ring and which may have in position 5 of the oxazolidinone ring an unsubstituted N-methyl-2-thiophenecarboxamide residue, and their use as substances with antibacterial activity are disclosed in the U.S. Pat. No. 5,929,248, U.S. Pat. No. 5,801,246, U.S. Pat. No. 5,756,732, U.S. Pat. No. 5,654,435, U.S. Pat. No. 5,654,428 and U.S. Pat. No. 5,565,571.

In addition, benzamidine-containing oxazolidinones are known as synthetic intermediates in the synthesis of factor Xa inhibitors or fibrinogen antagonists (WO-A-99/31092, EP-A-623615).

The compounds of the formula (I) may, depending on the substitution pattern, exist in stereoisomeric forms which either are related as image and mirror image (enantiomers) or are not related as image and mirror image (diastereomers).

Both the enantiomers or diastereomers and respective mixtures thereof are included. The racemic forms can, just like the diastereomers, be separated in a known manner into the stereoisomerically pure constituents.

Certain compounds of the formula (I) may also exist in tautomeric forms. This is known to the skilled worker, and such compounds are likewise included.

Physiologically acceptable, i.e. pharmaceutically acceptable, salts may be salts of the compounds of the invention with inorganic or organic acids. Preferred salts are those with inorganic acids such as, for example, hydrochloric acid, hydrobromic acid, phosphoric acid or sulfuric acid, or salts with organic carboxylic or sulfonic acids such as, for example, acetic acid, trifluoroacetic acid, propionic acid, maleic acid, fumaric acid, malic acid, citric acid, tartaric acid, lactic acid, benzoic acid, or methanesulfonic acid, ethanesulfonic acid, benzenesulfonic acid, toluenesulfonic acid or naphthalnedisulfonic acid.

Pharmaceutically acceptable salts which may also be mentioned are salts with conventional bases, such as, for example, alkali metal salts (e.g. sodium or potassium salts), alkaline earth metal salts (e.g. calcium or magnesium salts) or ammonium salts derived from ammonia or organic amines such as, for example, diethylamine, triethylamine, ethyldiisopropylamine, procaine, dibenzylamine, N-methylmorpholine, dihydroabietylamine or methylpiperidine.

"Hydrates" refers to those forms of the compounds of the above formula (I) which form a molecular compound (solvate) in the solid or liquid state through hydration with water. In the hydrates, the water molecules are attached through secondary valencies by intermolecular forces, in particular hydrogen bonds. Solid hydrates contain water as so-called water of crystallization in stoichiometric ratios, and the water molecules do not have to be equivalent in terms of their binding state. Examples of hydrates are sesquihydrates, monohydrates, dihydrates or trihydrates. Equally suitable are also the hydrates of salts of the compounds of the invention.

"Prodrugs" refers to those forms of the compounds of the above formula (I) which may themselves be biologically active or inactive but can, be converted into the corresponding biologically active form (for example metabolically, solvolytically or in another way).

Halogen is fluorine, chlorine, bromine and iodine. Chlorine or fluorine are preferred.

($C_1$-$C_8$)-Alkyl is a straight-chain or branched alkyl radical having 1 to 8 carbon atoms. Examples which may be mentioned are: methyl, ethyl, n-propyl, isopropyl, n-butyl, isobutyl, tert-butyl, n-pentyl and n-hexyl. The corresponding alkyl groups with fewer carbon atoms are derived analogously from this definition, such as, for example, ($C_1$-$C_6$)-alkyl and ($C_1$-$C_4$)-alkyl. It is generally true that ($C_1$-$C_4$)-alkyl is preferred.

The meaning of the corresponding constituent of other more complex substituents is also derived from this definition, such as, for example, in the case of alkylsulfonyl, hydroxyalkyl, hydroxyalkylcarbonyl, alkoxy-alkyl, alkoxycarbonyl-alkyl, alkanoylalkyl, aminoalkyl or alkylaminoalkyl.

($C_3$-$C_7$)-Cycloalkyl is a cyclic alkyl radical having 3 to 7 carbon atoms. Examples which may be mentioned are: cyclopropyl, cyclobutyl, cyclopentyl, cyclohexyl or cycloheptyl. The corresponding cycloalkyl groups with fewer carbon atoms are derived analogously from this definition, such as, for example, ($C_3$-$C_5$)-cycloalkyl. Cyclopropyl, cyclopentyl and cyclohexyl are preferred.

The meaning of the corresponding constituent of other more complex substituents such as, for example, cycloalkanoyl is also derived from this definition.

$(C_2-C_6)$-Alkenyl is a straight-chain or branched alkenyl radical having 2 to 6 carbon atoms. A straight-chain or branched alkenyl radical having 2 to 4 carbon atoms is preferred. Examples which may be mentioned are: vinyl, allyl, isopropenyl and n-but-2-en-1-yl.

$(C_1-C_8)$-Alkoxy is a straight-chain or branched alkoxy radical having 1 to 8 carbon atoms. Examples which may be mentioned are: methoxy, ethoxy, n-propoxy, isopropoxy, n-butoxy, isobutoxy, tert-butoxy, n-pentoxy, n-hexoxy, n-heptoxy and n-octoxy. The corresponding alkoxy groups with fewer carbon atoms are derived analogously from this definition, such as, for example, $(C_1-C_6)$-alkoxy and $(C_1-C_4)$-alkoxy. It is generally true that $(C_1-C_4)$-alkoxy is preferred.

The meaning of the corresponding constituent of other more complex constituents such as, for example, alkoxyalkyl, alkoxycarbonyl-alkyl and alkoxycarbonyl is also derived from this definition.

Mono- or di-$(C_1-C_4)$-alkylaminocarbonyl is an amino group which is linked via a carbonyl group and which has a straight-chain or branched or two identical or different straight-chain or branched alkyl substituents each having 1 to 4 carbon atoms.

Examples which may be mentioned are: methylamino, ethylamino, n-propylamino, isopropylamino, t-butylamino, N,N-dimethylamino, N,N-diethylamino, N-ethyl-N-methylamino, N-methyl-N-n-propylamino, N-isopropyl-N-n-propylamino and N-t-butyl-N-methylamino.

$(C_1-C_6)$-Alkanoyl is a straight-chain or branched alkyl radical having 1 to 6 carbon atoms which has a double bonded oxygen atom in position 1 and is linked via position 1. Examples which may be mentioned are: formyl, acetyl, propionyl, n-butyryl, i-butyryl, pivaloyl, n-hexanoyl. The corresponding alkanoyl groups with fewer carbon atoms are derived analogously from this definition, such as, for example, $(C_1-C_5)$-alkanoyl, $(C_1-C_4)$-alkanoyl and $(C_1-C_3)$-alkanoyl. It is generally true that $(C_1-C_3)$-alkanoyl is preferred.

The meaning of the corresponding constituent of other more complex constituents such as, for example, cycloalkanoyl and alkanoylalkyl is also derived from this definition.

$(C_3-C_7)$-Cycloalkanoyl is a cycloalkyl radical as defined above which has 3 to 7 carbon atoms and which is linked via a carbonyl group.

$(C_1-C_6)$-Alkanoyloxymethyloxy is a straight-chain or branched alkanoyloxymethyloxy radical having 1 to 6 carbon atoms. Examples which may be mentioned are: acetoxymethyloxy, propionoxymethyloxy, n-butyroxymethyloxy, i-butyroxymethyloxy, pivaloyloxymethyloxy, n-hexanoyloxymethyloxy. The corresponding alkanoyloxymethyloxy groups with fewer carbon atoms, such as, for example, $(C_1-C_3)$-alkanoyloxymethyloxy, are derived analogously from this definition. It is generally true that $(C_1-C_3)$-alkanoyloxymethyloxy is preferred.

$(C_6-C_{14})$-Aryl is an aromatic radical having 6 to 14 carbon atoms. Examples which may be mentioned are: phenyl, naphthyl, phenanthrenyl and anthracenyl. The corresponding aryl groups with fewer carbon atoms, such as, for example, $(C_6-C_{10})$-aryl, are derived analogously from this definition. It is generally true that $(C_6-C_{10})$-aryl is preferred.

The meaning of the corresponding constituent of other more complex constituents such as, for example, arylcarbonyl is also derived from this definition.

$(C_5-C_{10})$-Heteroaryl or a 5- to 10-membered aromatic heterocycle having up to 3 heteroatoms and/or hetero chain members from the series S, O, N and/or NO (N-oxide) is a mono- or bicyclic heteroaromatic system which is linked via a ring carbon atom of the heteroaromatic system, optionally also via a ring nitrogen atom of the heteroaromatic system. Examples which may be mentioned are: pyridyl, pyridyl N-oxide, pyrimidyl, pyridazinyl, pyrazinyl, thienyl, furyl, pyrrolyl, pyrazolyl, imidazolyl, thiazolyl, oxazolyl or isoxazolyl, indolizinyl, indolyl, benzo[b]thienyl, benzo[b]furyl, indazolyl, quinolyl, isoquinolyl, naphthyridinyl, quinazolinyl. The corresponding heterocycles with a smaller ring size such as, for example, 5- or 6-membered aromatic heterocycles are derived analogously from this definition. It is generally true that 5- or 6-membered aromatic heterocycles such as, for example, pyridyl, pyridyl N-oxide, pyrimidyl, pyridazinyl, furyl and thienyl are preferred.

The meaning of the corresponding constituent of other more complex constituents such as, for example, $(C_5-C_{10})$-heteroarylcarbonyl is also derived from this definition.

A 3- to 9-membered saturated or partially unsaturated, mono- or bicyclic, optionally benzo-fused heterocycle having up to 3 heteroatoms and/or hetero chain members from the series S, SO, $SO_2$, N, NO (N-oxide) and/or O is a heterocycle which may comprise one or more double bonds, which may be mono- or bicyclic, in which a benzene ring may be fused to two adjacent ring carbon atoms, and which is linked via a ring carbon atom or a ring nitrogen atom. Examples which may be mentioned are: tetrahydrofuryl, pyrrolidinyl, pyrrolinyl, piperidinyl, 1,2-dihydropyridinyl, 1,4-dihydropyridinyl, piperazinyl, morpholinyl, morpholinyl N-oxide, thiomorpholinyl, azepinyl, 1,4-diazepinyl and cyclohexyl. Piperidinyl, morpholinyl and pyrrolidinyl are preferred.

The corresponding cyclic systems with a small ring size, such as, for example, 5- to 7-membered cyclic systems are derived analogously from this definition.

The compounds of the formula (I) can be prepared by either, in a process alternative,

[A] reacting compounds of the general formula (II)

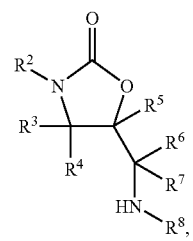

(II)

in which the radicals $R^2$, $R^3$, $R^4$, $R^5$, $R^6$, $R^7$ and $R^8$ have the meanings indicated above, with carboxylic acids of the general formula (III)

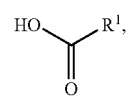

(III)

in which the radical $R^1$ has the meaning indicated above, or else with the corresponding carbonyl halides, preferably carbonyl chlorides, or else with the corresponding symmetrical or mixed carboxylic anhydrides of the carboxylic acids of the general formula (III) defined above in inert solvents, where appropriate in the presence of an activating or coupling reagent and/or of a base, to give compounds of the general formula (I)

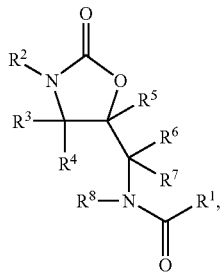
(I)

in which
the radicals $R^1$, $R^2$, $R^3$, $R^4$, $R^5$, $R^6$, $R^7$ and $R^8$ have the meanings indicated above,
or else in a process alternative
[B] converting compounds of the general formula (IV)

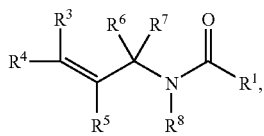
(IV)

in which
the radicals $R^1$, $R^3$, $R^4$, $R^5$, $R^6$, $R^7$ and $R^8$ have the meanings indicated above,
with a suitable selective oxidizing agent in an inert solvent into the corresponding epoxide of the general formula (V)

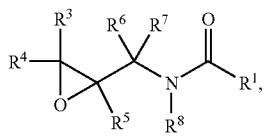
(V)

in which
the radicals $R^1$, $R^3$, $R^4$, $R^5$, $R^6$, $R^7$ and $R^8$ have the meanings indicated above,
and are reacted in an inert solvent, where appropriate in the presence of a catalyst, with an amine of the general formula (VI)

$R^2$—$NH_2$ (VI), in which
the radical $R^2$ has the meaning indicated above,
initially preparing the compounds of the general formula (VII)

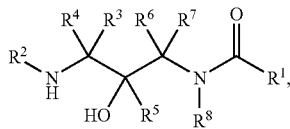
(VII)

in which
the radicals $R^1$, $R^2$, $R^3$, $R^4$, $R^5$, $R^6$, $R^7$ and $R^8$ have the meanings indicated above,
and
subsequently cyclizing in an inert solvent in the presence of phosgene or phosgene equivalents such as, for example, carbonyldiimidazole (CDI) to the compounds of the general formula (I)

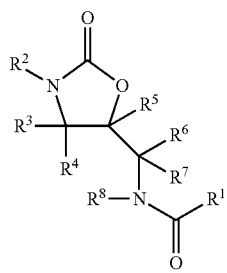
(I)

in which
the radicals $R^1$, $R^2$, $R^3$, $R^4$, $R^5$, $R^6$, $R^7$ and $R^8$ have the meanings indicated above,
where, both for process alternative [A] and for process alternative [B] in the case where $R^2$ is a 3- to 7-membered saturated or partially unsaturated cyclic hydrocarbon radical having one or more identical or different heteroatoms from the group of N and S, it is possible for an oxidation with a selective oxidizing agent, to the corresponding sulfone, sulfoxide or N-oxide to follow,
and/or
where, both for process alternative [A] and for process alternative [B] in the case where the compound prepared in this way has a cyano group in the molecule, it is possible for an amidination of this cyano group by conventional methods to follow,
and/or
where, both for process alternative [A] and for process alternative [B] in the case where the compound prepared in this way has a BOC amino protective group in the molecule, it is possible for an elimination of this BOC amino protective group by conventional methods to follow,
and/or
where, both for process alternative [A] and for process alternative [B] in the case where the compound prepared in this way has an aniline or benzylamine residue in the molecule, it is possible for a reaction of this amino group with various reagents such as carboxylic acids, carboxylic anhydrides, carbonyl chlorides, isocyanates, sulfonyl chlorides or alkyl halides to give the corresponding derivatives to follow,
and/or
where, both for process alternative [A] and for process alternative [B] in the case where the compound prepared in this way has a phenyl ring in the molecule, it is possible for a reaction with chlorosulfonic acid and subsequent reaction with amines to give the, corresponding sulfonamides to follow.

The processes can be illustrated by way of example by the following formula diagrams:
[A]
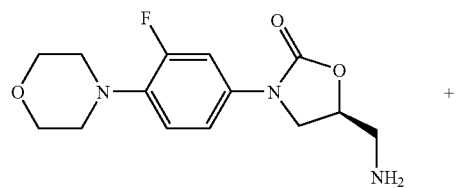
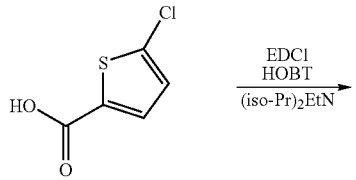
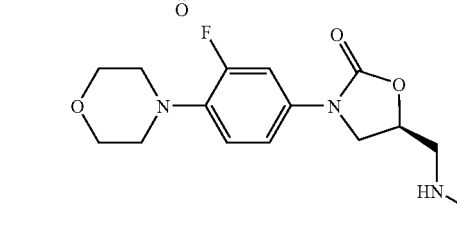
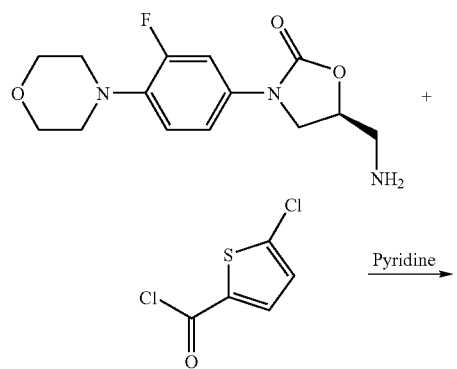
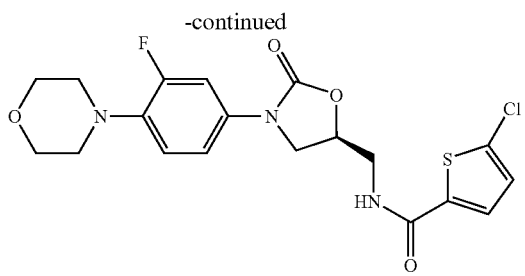
[B]
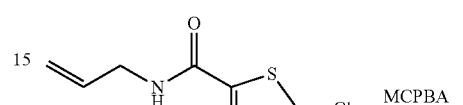
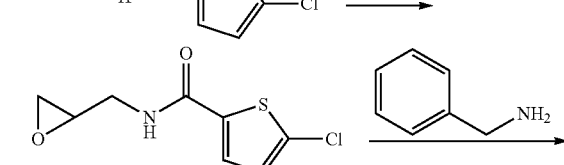
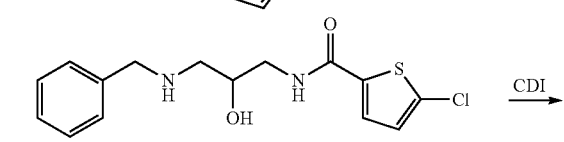
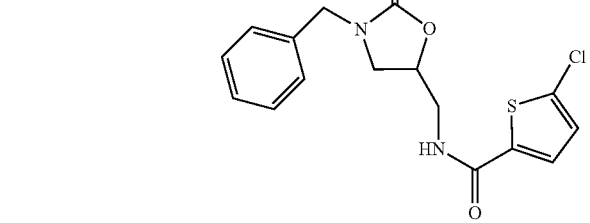
The oxidation step described above, which takes place where appropriate, can be illustrated by way of example by the following formula diagrams:
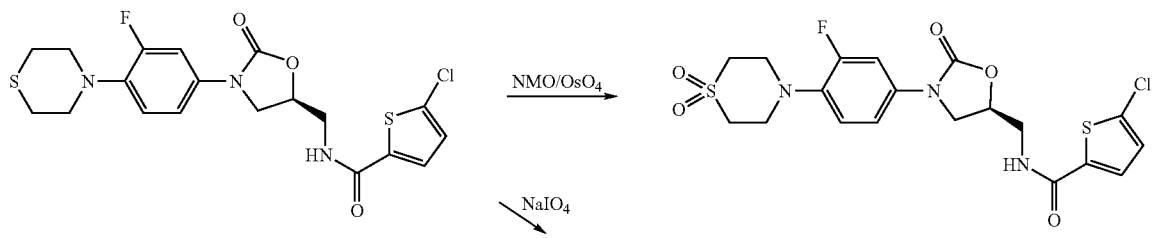
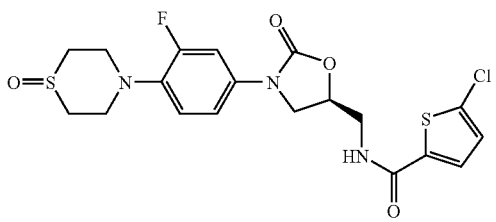

Solvents suitable for the processes described above are in these cases organic solvents which are inert under the reaction conditions. These include halohydrocarbons such as dichloromethane, trichloromethane, tetrachloromethane, 1,2-dichloroethane, trichloroethane, tetrachloroethane, 1,2-dichloroethylene or trichloroethylene, ethers such as diethyl ether, dioxane, tetrahydrofuran, glycol dimethyl ether or diethylene glycol dimethyl ether, alcohols such as methanol, ethanol, n-propanol, isopropanol, n-butanol or tert-butanol, hydrocarbons such as benzene, xylene, toluene, hexane or cyclohexane, dimethylformamide, dimethyl sulfoxide, acetonitrile, pyridine, hexamethylphosphoric triamide or water.

It is likewise possible to employ solvent mixtures composed of the aforementioned solvents.

Activating or coupling reagents suitable for the processes described above are in these cases the reagents normally used for these purposes, for example N'-(3-dimethylaminopropyl)-N-ethylcarbodiimide.HCl, N,N'-dicyclohexylcarbodiimide, 1-hydroxy-1H-benzotriazole.$H_2O$ and the like.

Suitable bases are the usual inorganic or organic bases. These preferably include alkali metal hydroxides such as, for example, sodium or potassium hydroxide or alkali metal carbonates such as sodium or potassium carbonate or sodium or potassium methanolate or sodium or potassium ethanolate or potassium tert-butoxide or amides such as sodamide, lithium bis-(trimethylsilyl)amide or lithium diisopropylamide or amines such as triethylamine, diisopropylethylamine, diisopropylamine, 4-N,N-dimethylaminopyridine or pyridine.

The base can be employed in these cases in an amount of from 1 to 5 mol, preferably from 1 to 2 mol, based on 1 mol of the compounds of the general formula (II).

The reactions generally take place in a temperature range from −78° C. to the reflux temperature, preferably in the range from 0° C. to the reflux temperature.

The reactions can be carried out under atmospheric, elevated or reduced pressure (e.g. in the range from 0.5 to 5 bar), generally under atmospheric pressure.

Suitable selective oxidizing agents both the preparing epoxides and for the oxidation which is optionally carried out to the sulfone, sulfoxide or N-oxide are, for example, m-chloroperbenzoic acid (MCPBA), sodium metaperiodate, N-methylmorpholine N-oxide (NMO), monoperoxyphthalic acid or osmium tetroxide.

The conditions used for preparing the epoxides are those customary for these preparations.

For detailed conditions for the process of oxidation, which is carried out where appropriate, to the sulfone, sulfoxide or N-oxide, reference may be made to the following literature: M. R. Barbachyn et al., J. Med. Chem. 1996, 39, 680 and WO-A-97/10223.

Reference is further made to Examples 14 to 16 detailed in the experimental part.

The amidination which is carried out where appropriate takes place under the usual conditions. For further details, reference may be made to Examples 31 to 35 and 140 to 147.

The compounds of the formulae (II), (III), (IV) and (VI) are known per se to the skilled worker or can be prepared by conventional methods. For oxazolidinones, in particular the 5-(aminomethyl)-2-oxooxazolidines required, cf. WO-A-98/01446; WO-A-93/23384; WO-A-97/03072; J. A. Tucker et al., J. Med. Chem. 1998, 41, 3727; S. J. Brickner et al., J. Med. Chem. 1996, 39, 673; W. A. Gregory et al., J. Med. Chem. 1989, 32, 1673.

A preferred compound A) of the formula (I) for use in combinations is 5-chloro-N-({(5S)-2-oxo-3-[4-(3-oxo-4-morpholinyl)phenyl]-1,3-oxazolidin-5-yl}methyl)-2-thiophenecarboxamide, the compound of Example 44.

The combinations of the invention are suitable in particular for the prophylaxis and/or treatment of arterial thromboses and embolisms associated with coronary heart disease, impairments of cerebrovascular blood flow and impairments of peripheral arterial blood flow. Combinations of oxazolidinones of the formula (I) with platelet aggregation inhibitors, anticoagulants and/or fibrinolytics are additionally suitable in particular for the prophylaxis and/or treatment of venous thromboses and pulmonary embolisms.

The individual active ingredients of the combinations are known from the literature and for the most part commercially available. They may, where appropriate, just like the oxazolidinones of the formula (I), be employed in subtherapeutically effective doses.

Suitable for the prophylaxis and/or treatment of arterial vascular disorders is a combination therapy of oxazolidinones of the formula (I) with lipid-lowering agents, in particular with HMG-CoA (3-hydroxy-3-methylglutaryl-coenzyme A) reductase inhibitors such as, for example, cerivastatin (Rivastatin, Baycol; U.S. Pat. No. 5,177,080), lovastatin (Mevacor; U.S. Pat. No. 4,231,938), simvastatin (Zocor; U.S. Pat. No. 4,444,784), pravastatin (Pravachol; U.S. Pat. No. 4,346,227), fluvastatin (Lescol; U.S. Pat. No. 5,354,772), atorvastatin (Lipitor; U.S. Pat. No. 5,273,995), or with coronary therapeutic agents/vasodilators, in particular ACE (angiotensin converting enzyme) inhibitors, such as, for example, captopril, lisinopril, enalapril, ramipril, cilazapril, benazepril, fosinopril, quinapril, perindopril; AII (angiotensin II) receptor antagonists such as, for example, embusartan (U.S. Pat. No. 5,863,930), losartan, valsartan, irbesartan, candesartan, eprosartan, temisartan; β-adrenoceptor antagonists such as, for example, carvedilol, alprenolol, bisoprolol, acebutolol, atenolol, betaxolol, carteolol, metoprolol, nadolol, penbutolol, pindolol, propanolol, timolol; alpha-1-adrenoceptor antagonists such as, for example, prazosin, bunazosin, doxazosin, terazosin; diuretics such as, for example, hydrochlorothiazide, furosemide, bumetanide, piretanide, torasemide, amiloride; dihydralazine; calcium channel blockers such as, for example, verapamil, diltiazem or dihydropyridine derivatives such as, for example, nifedipine (Adalat) or nitrendipine (Bayotensin); substances which bring about an increase in cyclic guanosine monophosphate (cGMP), such as, for example, stimulators of soluble guanylate cyclase (WO 98/16223, WO 98/16507, WO 98/23619, WO 00/06567, WO 00/06568, WO 00/06569, WO 00/21954, WO 00/66582, WO 01/17998, WO 01/19776, WO 01/19355, WO 01/19780, WO 01/19778).

The pharmacotherapeutic aim of treatment of a pre-existing coronary heart disease is to eliminate the inbalance between oxygen supply and oxygen demand in the areas of myocardium affected by the ischemia. Suitable for the treatment of a pre-existing coronary heart disease is therefore in particular combination therapy of an oxazolidinone of the formula (I) with coronary therapeutic agents, in particular with β-adrenoceptor antagonists; ACE (angiotensin converting enzyme) inhibitors; A-II (angiotensin II) receptor antagonists; nitrates such as, for example, isosorbide 5-mononitrate, isosorbide dinitrate, glycerol trinitrate; substances which bring about an increase in cyclic guanosine monophosphate (cGMP); calcium channel blockers. Most of these compounds are also employed for therapy of hypertension.

Thrombolytic therapy with plasminogen acktivators (thrombolytic/fibrinolytic agents) such as, for example, tissue plasminogen activator (t-PA), streptokinase, reteplase or urokinase has proved effective for reopening thrombotically occluded vessels. However, administration of plasminogen activators on their own does not prevent further growth of the thrombus. High doses of plasminogen activators may additionally mean an increased risk of bleeding. Combined administration of a thrombolytic agent with an oxazolidinone of the formula (I) for opening thrombotically occluded vessels associated with coronary heart disease, transient ischemic attacks, stroke, peripheral arterial occlusive diseases and pulmonary embolisms prevents further growth of the thrombus through inhibition of thrombin formation and thus reduces the risk of reocclusion. In addition, on combination therapy with a thrombolytic agent and an oxazolidinone of the formula (I) it is possible to reduce the dose of thrombolytic agent necessary for therapy, which leads to a reduction in the bleeding complications and thus represents a considerable advantage over monotherapy.

Oxazolidinones of the formula (I) can also be given in combination with other substances with anticoagulant activity (anticoagulants) for the prophylaxis and/or treatment of arterial, intracardiac and venous thromboembolic disorders. Combination therapy of oxazolidinones of the formula (I) in particular with heparin (UFH), lower molecular weight heparins (LMWH) such as, for example, tinzaparin, certoparin, parnaparin, nadroparin, ardeparin, enoxaparin, reviparin, dalteparin or direct thrombin inhibitors such as, for example, hirudin leads to an enhanced antithrombotic effect.

Oxazolidinones of the formula (I) can additionally also be given in combination with platelet aggregation-inhibiting substances (platelet aggregation inhibitors) for the prophylaxis and/or treatment of arterial, intracardiac and venous thromboembolic disorders. An endothelial lesion is associated with adhesion to the wall and activation of blood platelets and simultaneous stimulation of coagulation. This leads to the formation of platelet- and fibrin-containing thrombi, and the platelets contribute to stabilizing the fibrin matrix (J. Hirsh, E. W. Salzman, V. J. Marder, R. W. Colman, Overview of the Thrombotic Process and its Therapy, pages 1151-1163 in Hemostasis and Thrombosis: Basic Principles and Clinical Practice, Third Edition, edited by R. W. Colman, J. Hirsh, V. J. Marder, E. W. Salzman. J. B. Lippincott Company, Philadelphia, 1994). Simultaneous inhibition of coagulation and of platelet aggregation therefore leads to an enhanced antithrombotic effect. Particularly suitable for combination therapy are combinations of an oxazolidinone of the formula (I) with platelet aggregation inhibitors such as, for example, aspirin, ticlopidin (Ticlid), clopidogrel (Plavix); fibrinogen receptor antagonists; (glycoprotein IIb/IIIa antagonists) such as, for example, abciximab, eptifibatide, tirofiban, lamifiban, lefradafiban.

All usual administration forms are suitable for administering the combinations of the invention. Administration preferably takes place orally, lingually, sublingually, buccally, rectally, topically or parenterally (i.e. avoiding the intestinal tract, i.e. intravenous, intraarterial, intracardiac, intracutaneous, subcutaneous, transdermal, intraperitoneal or intramuscular).

The present invention includes pharmaceutical preparations which, besides non-toxic, inert pharmaceutically suitable excipients and/or carriers, comprise one or more combinations of the invention or which consist of a combination of the invention, and processes for producing these preparations.

The combinations of the invention are intended to be present in the abovementioned pharmaceutical preparations in a concentration of about 0.1 to 99.5, preferably about 0.5 to 95, % by weight of the complete mixture.

The abovementioned pharmaceutical preparations may, besides the combinations of the invention, also comprise further active pharmaceutical ingredients.

The abovementioned pharmaceutical preparations can be produced in a conventional way by known methods, e.g. by mixing the active ingredient or active ingredients with the carrier(s).

It has generally proved advantageous to administer the combinations of the invention in total amounts of about 0.001 to 100 mg/kg, preferably about 0.01 to 100 mg/kg, in particular about 0.1 to 10 mg/kg, of body weight every 24 hours, where appropriate in the form of a plurality of single doses, to achieve the desired results.

It may nevertheless be necessary where appropriate to depart from the aforementioned amounts, in particular depending on the body weight, on the nature of the administration route, the type and severity of the disorder, on the individual behavior toward the medicament, on the nature of the formulation and on the time or interval over which administration takes place. Thus, it may be sufficient in some cases to make do with less than the aforementioned minimum amount, whereas in other cases the upper limit mentioned must be exceeded. It may be advisable, for example when relatively large amounts are administered, to distribute these over the day, in particular either in a plurality of single doses or as continuous infusion.

The invention therefore further relates to the combinations defined above for the prophylaxis and/or treatment of disorders.

The invention further relates to medicaments comprising at least one of the combinations defined above and, where appropriate, further active pharmaceutical ingredients.

The invention further relates to the use of the combinations defined above for producing medicaments for the prophylaxis and/or treatment of the disorders described above, preferably thromboembolic disorders, in particular myocardial infarction, angina pectoris (including unstable angina), sudden heart death, reocclusions and restenoses after an angioplasty or aortocoronary bypass, stroke, transient ischemic attacks, peripheral arterial occlusive diseases, pulmonary embolisms or deep venous thromboses.

The percentage data in the following examples are based in each case on weight; parts are parts by weight.

EXAMPLES

A Assessment of the Physiological Activity

1. Physiological Activity of Compounds of the Formula (I)

The compounds of the formula (I) act in particular as selective inhibitors of coagulation factor Xa and do not inhibit, or also inhibit only at distinctly higher concentrations, other serine proteases such as thrombin, plasmin or trypsin.

Inhibitors of coagulation factor Xa are referred to as "selective" when their $IC_{50}$ values for factor Xa inhibition are 100-fold, preferably 500-fold, in particular 1000-fold, smaller than the $IC_{50}$ values for the inhibition of other serine proteases, in particular thrombin, plasmin and trypsin, reference being made concerning the test methods for the selectivity to the test methods of Examples A-1) a.1) and a.2) described below.

The particularly advantageous biological properties of the compounds of the formula (I) can be ascertained by the following methods.

a) Test Description (in vitro)

a.1) Measurement of Factor Xa Inhibition

The enzymatic activity of human factor Xa (FXa) was measured via the conversion of an FXa-specific chromogenic substrate. In this case, factor Xa eliminates p-nitroaniline from the chromogenic substrate. The determinations were carried out in microtiter plates as follows.

The test substances were dissolved in various concentrations in DMSO and incubated with human FXa (0.5 nmol/l dissolved in 50 mmol/l tris buffer [C,C,C-tris(hydroxymethyl)-aminomethane], 150 mmol/l NaCl, 0.1% BSA (bovine serum albumine), pH=8.3) at 25° C. for 10 minutes. Pure DMSO serves as control. The chromogenic substrate (150 µmol/l Pefachrome® FXa from Pentapharm) was then added. After incubation at 25° C. for 20 minutes, the extinction at 405 nm was determined. The extinctions of the test mixtures with test substance were compared with the control mixtures without test substance, and the $IC_{50}$ values were calculated therefrom.

a.2) Selectivity Determination

Selective FXa inhibition was demonstrated by investigating the inhibition by the test substances of other human serine proteases such as thrombin, trypsin, plasmin. The enzymatic activity of thrombin (75 mU/ml), trypsin (500 mU/ml) and plasmin (3.2 nmol/l) was determined by dissolving these enzymes in tris buffer (100 mmol/l, 20 mmol/l $CaCl_2$, pH=8.0) and incubating with test substance or solvent for 10 minutes. The enzymatic reaction was then started by adding the appropriate specific chromogenic substrates (Chromozym Thrombin® from Boehringer Mannheim, Chromozym Trypsin® from Boehringer Mannheim, Chromozym Plasmin® from Boehringer Mannheim), and the extinction was determined at 405 nm after 20 minutes. All determinations were carried out at 37° C. The extinctions of the test mixtures with test substance were compared with the control samples without test substance, and the $IC_{50}$ values were calculated therefrom.

a.3) Determination of the Anticoagulant Effect

The anticoagulant effect of the test substances was determined in vitro in human plasma. For this purpose, human blood was collected in a 0.11 molar sodium citrate solution in the sodium citrate/blood mixing ratio of 1/9. The blood was thoroughly mixed after collection and centrifuged at about 2000 g for 10 minutes. The supernatant was removed by pipette. The prothrombin time (PT, synonym: Quick's test) was determined in the presence of varying concentrations of test substance or the appropriate solvent using a commercially available test kit (Neoplastin® from Boehringer Mannheim). The test compounds were incubated with the plasma at 37° C. for 10 minutes. Coagulation was then induced by adding thromboplastin, and the time of onset of coagulation was determined. The concentration of test substance which brings about a doubling of the prothrombin time was found.

b) Determination of the Antithrombotic Effect (in vivo)

b.1) Arteriovenous Shunt Model (Rat)

Fasting male rats (strain: HSD CPB:WU) weighing 200-250 g were anesthetized with a Rompun/Ketavet solution (12 mg/kg/50 mg/kg). Thrombus formation was induced in an arteriovenous shunt by a method based on that described by Christopher N. Berry et al., Br. J. Pharmacol. (1994), 113, 1209-1214. For this purpose, the left jugular vein and the right carotid artery were exposed. An extracorporeal shunt was formed between the two vessels using a 10 cm-long polyethylene tube (PE 60). This polyethylene tube was secured in the middle by tying in a further 3 cm-long polyethylene tube (PE 160) which contained a roughened nylon thread forming a loop to produce a thrombogenic surface. The extracorporeal circulation was maintained for 15 minutes. The shunt was then removed and the nylon thread with the thrombus was immediately weighed. The blank weight of the nylon thread had been found before the start of the experiment. The test substances were administered either intravenously through the tail vein or orally by gavage to conscious animals before setting up the extracorporeal circulation. The results are shown in Table 1:

TABLE 1

Antithrombotic effect in the arteriovenous shunt model (rat) after oral or intravenous administration

| Example | $ED_{50}$ [mg/kg] p.o. | $ED_{50}$ [mg/kg] i.v. |
|---------|------------------------|------------------------|
| 1       |                        | 10                     |
| 17      |                        | 6                      |
| 44      | 3                      |                        |
| 95      |                        | 3                      |
| 114     |                        | 3                      |
| 115     |                        | 3                      |
| 123     | 3                      |                        |
| 162     |                        | 3                      | b.2) Arterial Thrombosis Model (Rat)

Fasting male rats (strain: HSD CPB: WU) were anesthetized as described above. The rats had an average weight of about 200 g. The left carotid artery was exposed (about 2 cm). Formation of an arterial thrombus was induced by mechanical injury to the vessel by a method based on that described by K. Meng et al., Naunyn-Schmiedeberg's Arch. Pharmacol. (1977), 301, 115-119. For this purpose, the exposed carotid artery was clamped off from the blood flow, cooled to −12° C. in a metal channel for 2 minutes and, to standardize the thrombus size, simultaneously compressed with a weight of 200 g. The blood flow was then additionally reduced by a clip placed around the carotid artery distal from the injured section of vessel. The proximal clamp was removed, and the wound was closed and reopened after 4 hours in order to remove the injured section of vessel. The section of vessel was opened longitudinally and the thrombus was removed from the injured section of vessel. The wet weight of the thrombi was measured immediately. The test substances were administered either intravenously via the tail vein or orally by gavage to conscious animals at the start of the experiment.

b.3) Venous Thrombosis Model (Rat)

Fasting male rats (strain: HSD CPB: WU) were anesthetized as described above. The rats had an average weight of about 200 g. The left jugular vein was exposed (about 2 cm). Formation of a venous thrombus was induced by mechanical injury to the vessel by a method based on that described by K. Meng et al., Naunyn-Schmiedeberg's Arch. Pharmacol. (1977), 301, 115-119. For this purpose, the exposed jugular vein was clamped off from the blood flow, cooled to −12° C. in a metal channel for 2 minutes and, to standardize the thrombus size, simultaneously compressed with a weight of 200 g. The blood flow was reopened and the wound was closed. After 4 hours, the wound was reopened in order to remove the thrombi from the injured sections of vessels. The wet weight of the thrombi was measured immediately. The test substances were administered either intravenously via the tail vein or orally by gavage to conscious animals at the start of the experiment.

2. Physiological Activity of the Combinations of Compounds of the Formula (I)

a) In vivo Investigations in a Rat Thrombosis Model

The carotid artery of rats (HSD CPB:WU, Harlan Winkelmann) was exposed under anesthesia. A piece of filter paper impregnated with an aqueous 10% strength FeCl₃ solution (dissolved in 1N aqueous hydrochloric acid) was cautiously pushed underneath the exposed vessel in accordance with the method described by Kurz et al. (Rat Model of Arterial Thrombosis Induced by Ferric Chloride, Thrombosis Research 60, 269-280, 1990). After 3 minutes, the piece of filter paper was removed. The carotid artery was removed after 15 minutes, and the thrombus was detached and immediately weighed. The animals (10 rats per group) had been pretreated with 1 mg/kg of each of the individual active ingredients (oxazolidinone of the formula (I) and combination active ingredient) or with the combination of 1 mg/kg oxazolidinone of the formula (I) and 1 mg/kg combination active ingredient. The animals in the control group had been treated with the corresponding solvent. The statistical significance was calculated using Student's t-test. Values with p<0.05 are regarded as a statistically significant effect (Medical Statistics, M J Campbell, D. Machin, Second Edition, John Wiley & Sons). The results are shown in Table 2:

TABLE 2

Synergistic antithrombotic effect of the combination of an oxazolidinone of the formula (I) with a platelet aggregation inhibitor
Reduction in thrombus weight after oral treatment with

| Compound of Example 44 [1 mg/kg] | Clopidogrel [1 mg/kg] | Combination of the compound of Example 44 [1 mg/kg] with clopidogrel [1 mg/kg] |
|---|---|---|
| 22% no effect (p > 0.05) | 28% no effect (p > 0.05) | 39% effect (p < 0.05) |

As shown in Table 2, a synergistic effect is achieved with the combination of an oxazolidinone of the formula (I) such as the compound of Example 44 with a platelet aggregation inhibitor such as clopidogrel, i.e. the two components mutually enhance their effect. In single dosage, both compounds were inactive at the dose investigated. Combination of the two compounds by contrast led to a significant reduction in the thrombus weight. Combination of oxazolidinones of the formula (I) with a platelet aggregation-inhibiting substance is therefore able to improve antithrombotic therapy considerably.

B Preparation Examples

Starting Compounds

The preparation of 3-morpholinone is described in U.S. Pat. No. 5,349,045.

The preparation of N-(2,3-epoxypropyl)phthalimide is described in J.-W. Chern et al. Tetrahedron Lett. 1998,39, 8483.

The substituted anilines can be obtained by reacting, for example, 4-fluoronitrobenzene, 2,4-difluoronitrobenzene or 4-chloronitrobenzene with the appropriate amines or amides in the presence of a base. This can also take place with use of Pd catalysts such as Pd(OAc)₂/DPPF/NaOt-Bu (Tetrahedron Lett. 1999,40,2035) or copper (Renger, Synthesis 1985,856; Aebischer et al., Heterocycles 1998,48,2225). Haloaromatic compounds without a nitro group can initially be converted into the corresponding amides in exactly the same way in order to be subsequently nitrated in position 4 (U.S. Pat. No. 3,279,880).

I. 4-(4-Morpholin-3-onyl)nitrobenzene

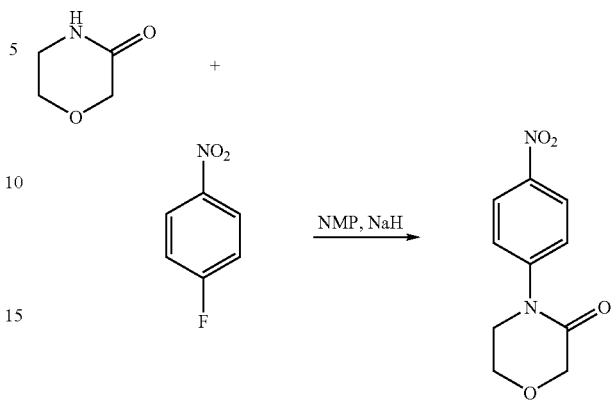

2 mol (202 g) of morpholin-3-one (E. Pfeil, U. Harder, Angew. Chem. 79, 1967, 188) are dissolved in 2 l of N-methylpyrrolidone (NMP). 88 g (2.2 mol) of sodium hydride (60% in paraffin) are then added in portions over a period of 2 h. After hydrogen evolution ceases, 282 g (2 mol) of 4-fluoronitrobenzene are added dropwise while cooling at room temperature over the course of 1 h, and the reaction mixture is then stirred overnight. Subsequently, 1.7 l of the liquid volume are distilled out at 12 mbar and 76° C., the residue is poured into 2 l of water, and this mixture is extracted twice with 1 l of ethyl acetate each time. The combined organic phases are washed with water and then dried over sodium sulfate, and the solvent is distilled off in vacuo. Purification takes place by chromatography on silica gel with hexane/ethyl acetate (1:1) and subsequent crystallization from ethyl acetate. The product is obtained as 78 g of a colorless to brownish solid in 17.6% of theory.

$^1$H-NMR (300 MHz, CDCl₃): 3.86 (m, 2H, CH₂CH₂), 4.08 (m, 2H, CH₂CH₂), 4.49 (s, 2H, CH₂CO), 7.61 (d, 2H, $^3$J=8.95 Hz, CHCH), 8.28 (d, 2H, $^3$J=8.95 Hz, CHCH). MS (r.I. %)=222 (74, M⁺), 193 (100), 164 (28), 150 (21), 136 (61), 117 (22), 106 (24), 90 (37), 76 (38), 63 (32), 50 (25).

The following compounds were synthesized analogously:
3-fluoro-4-(4-morpholin-3-onyl)nitrobenzene
4-(N-piperidonyl)nitrobenzene
3-fluoro-4-(N-piperidonyl)nitrobenzene
4-(N-pyrrolidonyl)nitrobenzene
3-fluoro-4-(N-pyrrolidonyl)nitrobenzene II. 4-(4-Morpholin-3-onyl)aniline

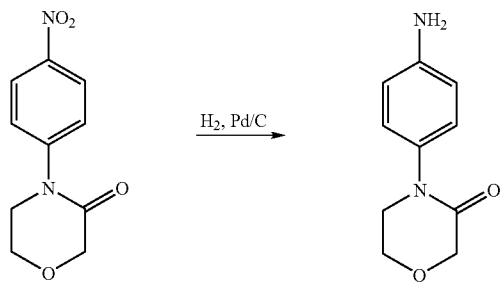

63 g (0.275 mol) of 4-(4-morpholin-3-onyl)nitrobenzene are dissolved in 200 ml of tetrahydrofuran in an autoclave, 3.1 g of Pd/C (5%) are added, and the mixture is hydrogenated under a hydrogen pressure of 50 bar at 70° C. for 8 h. After filtration of the catalyst, the solvent is distilled out in vacuo and the product is purified by crystallization from ethyl acetate. The product is obtained as 20 g of a colorless to blueish solid in 37.6% of theory.

Purification can also take place by chromatography on silica gel with hexane/ethyl acetate.

$^1$H-NMR (300 MHz, CDCl$_3$): 3.67 (m, 2H, CH$_2$CH$_2$), 3.99 (m, 2H, CH$_2$CH$_2$), 4.27 (s, 2H, CH$_2$CO), 6.68 (d, 2H, $^3$J=8.71 Hz, CHCH), 7.03 (d, 2H, $^3$J=8.71 Hz, CHCH). MS (r.I. %)=192 (100, M$^+$), 163 (48), 133 (26), 119 (76), 106 (49), 92 (38), 67 (27), 65 (45), 52(22), 28 (22).

The following compounds were synthesized analogously:
3-fluoro-4-(4-morpholin-3-onyl)aniline
4-(N-piperidonyl)aniline
3-fluoro-4-(N-piperidonyl)aniline
4-(N-pyrrolidonyl)aniline
3-fluoro-4-(N-pyrrolidonyl)aniline General method for preparing 4-substituted anilines by reacting 1-fluoro-4-nitrobenzenes and 1-chloro-4-nitrobenzenes with primary or secondary amines and subsequent reduction

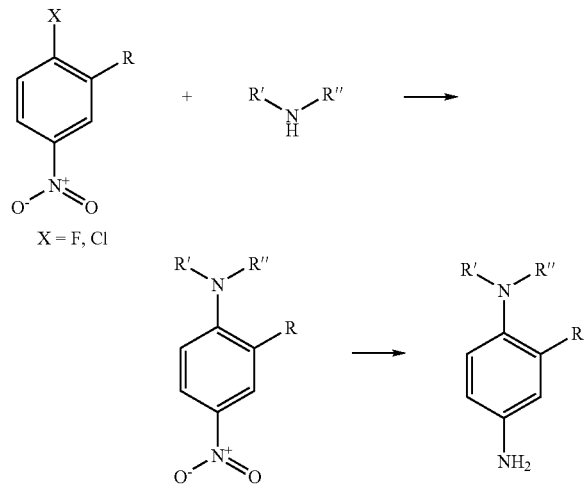

Equimolar amounts of the fluoronitrobenzene or chloronitrobenzene and of the amine are dissolved in dimethyl sulfoxide or acetonitrile (0.1 M to 1 M solution) and stirred at 100° C. overnight. After cooling to RT, the reaction mixture is diluted with ether and washed with water. The organic phase is dried over MgSO$_4$, filtered and concentrated. If a precipitate is obtained in the reaction mixture, it is filtered off and washed with ether or acetonitrile. If product is also to be found in the mother liquor, this is worked up with ether and water as described. The crude products can be purified by chromatography on silica gel (dichloromethane/cyclohexane and dichloromethane/ethanol mixtures).

For the subsequent reduction, the nitro compound is dissolved in methanol, ethanol or ethanol/dichloromethane mixtures (0.01 M to 0.5 M solution), mixed with palladium on carbon (10%) and stirred under hydrogen of atmospheric pressure overnight. This is followed by filtration and concentration. The crude product can be purified by chromatography on silica gel (dichloromethane/ethanol mixtures) or preparative reversed phase HPLC (acetonitrile/water mixtures).

Alternatively, iron powder can also be used as reducing agent. For this purpose, the nitro compound is dissolved in acetic acid (0.1 M to 0.5 M solution) and, at 90° C., six equivalents of iron powder and water (0.3 to 0.5 times the volume of acetic acid) are added in portions over the course of 10-15 min. After a further 30 min at 90° C., the mixture is filtered and the filtrate is concentrated. The residue is worked up by extraction with ethyl acetate and 2N sodium hydroxide solution. The organic phase is dried over magnesium sulfate, filtered and concentrated. The crude product can be purified by chromatography on silica gel (dichloromethane/ethanol mixtures) or preparative reversed phase HPLC (acetonitrile/water mixtures).

The following starting compounds were prepared in an analogous manner:

III-1. Tert-butyl 1-(4-aminophenyl)-L-prolinate
MS (ESI): m/z (%)=304 (M+H+MeCN, 100), 263 (M+H, 20); HPLC (method 4): rt=2.79 min.

III-2. 1-(4-Aminophenyl)-3-piperidinecarboxamide
MS (ESI): m/z (%)=220 (M+H, 100); HPLC (method 4): rt=0.59 min.

III-3. 1-(4-Aminophenyl)-4-piperidinecarboxamide
MS (ESI): m/z (%)=220 (M+H, 100); HPLC (method 4): rt=0.57 min.

III-4. 1-(4-Aminophenyl)-4-piperidinone
MS (ESI): m/z (%)=191 (M+H, 100); HPLC (method 4): rt=0.64 min.

III-5. 1-(4-Aminophenyl)-L-prolinamide
MS (ESI): m/z (%)=206 (M+H, 100); HPLC (method 4): rt=0.72 min.

III-6. [1-(4-Aminophenyl)-3-piperidinyl]methanol
MS (ESI): m/z (%)=207 (M+H, 100); HPLC (method 4): rt=0.60 min.

III-7. [1-(4-Aminophenyl)-2-piperidinyl]methanol
MS (ESI): m/z (%)=207 (M+H, 100); HPLC (method 4): rt=0.59 min.

III-8. Ethyl 1-(4-aminophenyl)-2-piperidinecarboxylate
MS (ESI): m/z (%)=249 (M+H, 35), 175 (100); HPLC (method 4): rt=2.43 min.

III-9. [1-(4-Aminophenyl)-2-pyrrolidinyl]methanol
MS (ESI): m/z (%)=193 (M+H, 45); HPLC (method 4): rt=0.79 min.

III-10. 4-(2-Methylhexahydro-5H-pyrrolo[3,4-d]isoxazol-5-yl)phenylamine
starting from 2-methylhexahydro-2H-pyrrolo[3,4-d]isoxazole (Ziegler, Carl B., et al.; J. Heterocycl. Chem.; 25; 2; 1988; 719-723)
MS (ESI): m/z (%)=220 (M+H, 50), 171 (100); HPLC (method 4): rt=0.54 min.

III-11. 4-(1-Pyrrolidinyl)-3-(trifluoromethyl)aniline
MS (ESI): m/z (%)=231 (M+H, 100); HPLC (method 7): rt=3.40 min.

III-12. 3-Chloro-4-(1-pyrrolidinyl)aniline
MS (ESI): m/z (%)=197 (M+H, 100); HPLC (method 4): rt=0.78 min.

III-13. 5-Amino-2-(4-morpholinyl)benzamide
MS (ESI): m/z (%)=222 (M+H, 100); HPLC (method 4): rt=0.77 min.

III-14. 3-Methoxy-4-(4-morpholinyl)aniline
MS (ESI): m/z (%)=209 (M+H, 100); HPLC (method 4): rt=0.67 min.

III-15. 1-[5-Amino-2-(4-morpholinyl)phenyl]ethanone
MS (ESI): m/z (%)=221 (M+H, 100); HPLC (method 4): rt=0.77 min.

General method for preparing 4-substituted anilines by reacting 1-fluoro-4-nitrobenzenes with amides and subsequent reduction

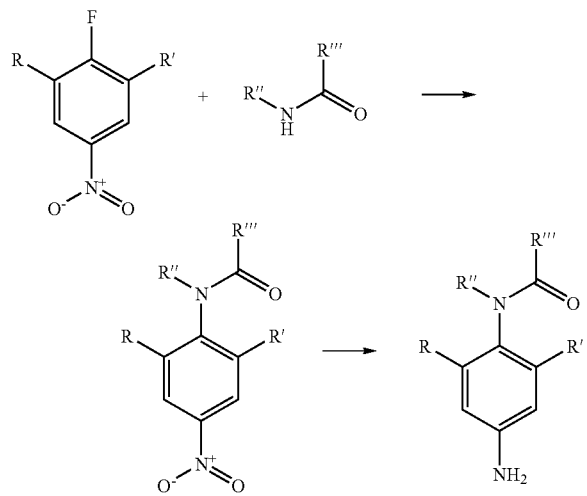

The amide is dissolved in DMF, and 1.5 equivalents of potassium tert-butoxide are added. The mixture is stirred at RT for 1 h, and then 1.2 equivalents of the 1-fluoro-4-nitrobenzene are added in portions. The reaction mixture is stirred at RT overnight, diluted with ether or ethyl acetate and washed with saturated aqueous sodium bicarbonate solution. The organic phase is dried over magnesium sulfate, filtered and concentrated. The crude product can be purified by chromatography on silica gel (dichloromethane/ethanol mixtures).

For the subsequent reduction, the nitro compound is dissolved in ethanol (0.01 M to 0.5 M solution), mixed with palladium on carbon (10%) and stirred under hydrogen of atmospheric pressure overnight. This is followed by filtration and concentration. The crude product can be purified by chromatography on silica gel (dichloromethane/ethanol mixtures) or preparative reversed phase HPLC (acetonitrile/water mixtures).

Alternatively, iron powder can also be used as reducing agent. For this purpose, the nitro compound is dissolved in acetic acid (0.1 M to 0.5 M solution) and, at 90° C., six equivalents of iron powder and water (0.3 to 0.5 times the volume of acetic acid) are added in portions over the course of 10-15 min. After a further 30 min at 90° C., the mixture is filtered and the filtrate is concentrated. The residue is worked up by extraction with ethyl acetate and 2N sodium hydroxide solution. The organic phase is dried over magnesium sulfate, filtered and concentrated. The crude product can be purified by chromatography on silica gel (dichloromethane/ethanol mixtures) or preparative reversed phase HPLC (acetonitrile/water mixtures).

The following starting compounds were prepared in an analogous manner:

IV-1. 1-[4-Amino-2-(trifluoromethyl)phenyl]-2-pyrrolidinone
MS (ESI): m/z (%)=245 (M+H, 100); HPLC (method 4): rt=2.98 min.

IV-2. 4-[4-Amino-2-(trifluoromethyl)phenyl]-3-morpholinone
MS (ESI): m/z (%)=261 (M+H, 100); HPLC (method 4): rt=2.54 min.

IV-3. 4-(4-Amino-2-chlorophenyl)-3-morpholinone
MS (ESI): m/z (%)=227 (M+H, 100); HPLC (method 4): rt=1.96 min.

IV-4. 4-(4-Amino-2-methylphenyl)-3-morpholinone
MS (ESI): m/z (%)=207 (M+H, 100); HPLC (method 4): rt=0.71 min.

IV-5. 5-Amino-2-(3-oxo-4-morpholinyl)benzonitrile
MS (ESI): m/z (%)=218 (M+H, 100); HPLC (method 4): rt=1.85 min.

IV-6. 1-(4-Amino-2-chlorophenyl)-2-pyrrolidinone
MS (ESI): m/z (%)=211 (M+H, 100); HPLC (method 4): rt=2.27 min.

IV-7. 4-(4-Amino-2,6-dimethylphenyl)-3-morpholinone
starting from 2-fluoro-1,3-dimethyl-5-nitrobenzene (Bartoli et al., J. Org. Chem. 1975, 40, 872):
MS (ESI): m/z (%)=221 (M+H, 100); HPLC (method 4): rt=0.77 min.

IV-8. 4-(2,4-Diaminophenyl)-3-morpholinone
starting from 1-fluoro-2,4-dinitrobenzene:
MS (ESI): m/z (%)=208 (M+H, 100); HPLC (method 4): rt=0.60 min.

IV-9. 4-(4-Amino-2-chlorophenyl)-2-methyl-3-morpholinone
starting from 2-methyl-3-morpholinone (Pfeil, E.; Harder, U.; Angew. Chem. 1967, 79, 188):
MS (ESI): m/z (%)=241 (M+H, 100); HPLC (method 4): rt=2.27 min.

IV-10. 4-(4-Amino-2-chlorophenyl)-6-methyl-3-morpholinone
starting from 6-methyl-3-morpholinone (EP 350 002):
MS (ESI): m/z (%)=241 (M+H, 100); HPLC (method 4): rt=2.43 min.

Synthesis Examples

The following Examples 1 to 13, 17 to 19 and 36 to 57 relate to process variant [A].

Example 1

Preparation of 5-chloro-N-{[(5S)-3-(3-fluoro-4-morpholinophenyl)-2-oxo-1,3-oxazolidin-5-yl]methyl}-2-thiophenecarboxamide

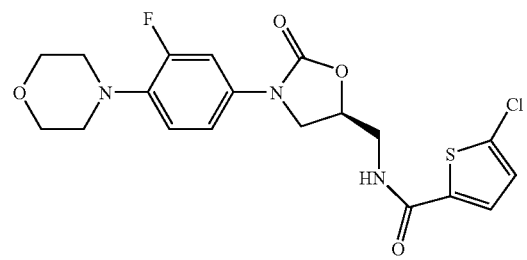

(5S)-5-(Aminomethyl)-3-(3-fluoro-4-morpholinophenyl)-1,3-oxazolidin-2-one (for preparation, see S. J. Brickner et al., J. Med. Chem. 1996, 39, 673) (0.45 g, 1.52 mmol), 5-chlorothiophene-2-carboxylic acid (0.25 g, 1.52 mmol) and 1-hydroxy-1H-benzotriazole hydrate (HOBT) (0.3 g, 1.3 equivalents) are dissolved in 9.9 ml of DMF. 0.31 g (1.98 mmol, 1.3 equivalents) of N'-(3-dimethylaminopropyl)-N-ethylcarbodiimide (EDCI) is added and, at room temperature, 0.39 g (0.53 ml, 3.05 mmol, 2 equivalents) of diisopropylethylamine (DIEA) is added dropwise. The mixture is stirred at room temperature overnight. 2 g of silica gel are added and the mixture is evaporated to dryness in vacuo. The residue is chromatographed on silica gel with a toluene/ethyl acetate gradient. 0.412 g (61.5% of theory) of the target compound is obtained with a melting point (m.p.) of 197° C.

$R_f$(SiO$_2$, toluene/ethyl acetate 1:1)=0.29 (precursor=0.0); MS (DCI) 440.2 (M+H), Cl pattern; $^1$H-NMR (d$_6$-DMSO; 300 MHz) 2.95 (m, 4H), 3.6 (t, 2H), 3.72 (m, 4H), 3.8 (dd, 1H), 4.12 (t, 1H), 4.75-4.85 (m, 1H), 7.05 (t, 1H), 7.15-7.2 (m, 3H), 7.45 (dd, 1H), 7.68 (d, 1H), 8.95 (t, 1H).

Example 2

5-Chloro-N-{[(5S)-3-(4-morpholinophenyl)-2-oxo-1,3-oxazolidin-5-yl]methyl}-2-thiophenecarboxamide

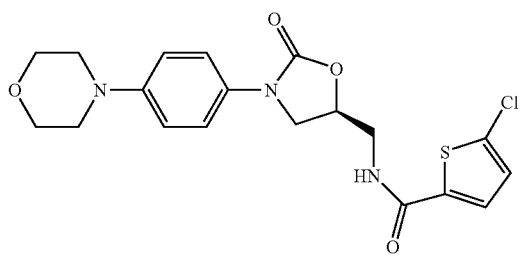

is obtained analogously from benzyl 4-morpholinophenyl-carbamate via the stage of (5S)-5-(aminomethyl)-3-(3-fluoro-4-morpholinophenyl)-1,3-oxazolidin-2-one (see Example 1).

M.p.: 198° C.; IC$_{50}$=43 nM; $R_f$(SiO$_2$, toluene/ethyl acetate 1:1)=0.24.

Example 3

5-Chloro-N-({(5S)-3-[3-fluoro-4-(1,4-thiazinan-4-yl)phenyl]-2-oxo-1,3-oxazolidin-5-yl}methyl)-2-thiophenecarboxamide

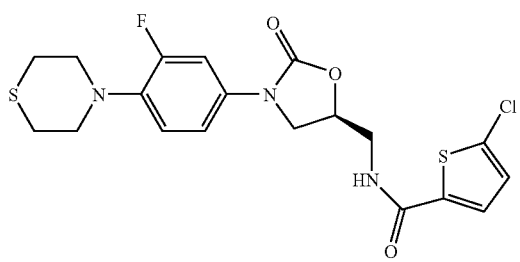

is obtained analogously from (5S)-5-(aminomethyl)-3-[3-fluoro-4-(1,4-thiazinan-4-yl)phenyl]-1,3-oxazolidin-2-one (for preparation, see M. R. Barbachyn et al., J. Med. Chem. 1996, 39, 680).

M.p.: 193° C.; Yield: 82%; $R_f$(SiO$_2$, toluene/ethyl acetate 1:1)=0.47 (precursor=0.0).

Example 4

5-Bromo-N-({(5S)-3-[3-fluoro-4-(1,4-thiazinan-4-yl)phenyl]-2-oxo-1,3-oxazolidin-5-yl}methyl)-2-thiophenecarboxamide

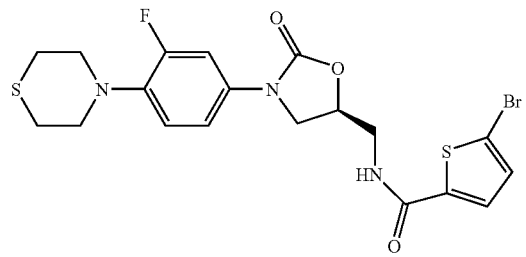

is obtained analogously from 5-bromothiophene-2-carboxylic acid.

M.p.: 200° C.

Example 5

N-({(5S)-3-[3-Fluoro-4-(1,4-thiazinan-4-yl)phenyl]-2-oxo-1,3-oxazolidin-5-yl}methyl)-5-methyl-2-thiophenecarboxamide

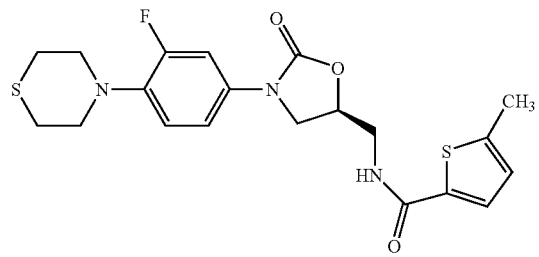

is obtained analogously from 5-methylthiophene-2-carboxylic acid.

M.p.: 167° C.

Example 6

5-Chloro-N-{[(5S)-3-(6-methylthieno[2,3-b]pyridin-2-yl)-2-oxo-1,3-oxazolidin-5-yl]methyl}-2-thiophenecarboxamide

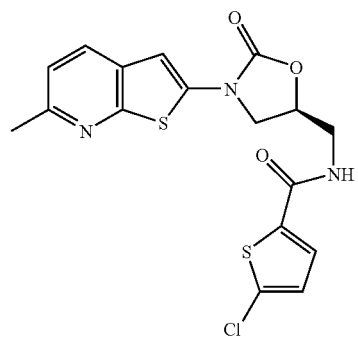

is obtained analogously from (5S)-5-(aminomethyl)-3-(6-methylthieno[2,3-b]pyridin-2-yl)-1,3-oxazolidin-2-one (for preparation, see EP-A-785 200).

M.p.: 247° C.

Example 7

5-Chloro-N-{[(5S)-3-(3-methyl-2-oxo-2,3-dihydro-1,3-benzothiazol-6-yl)-2-oxo-1,3-oxazolidin-5-yl]methyl}-2-thiophenecarboxamide

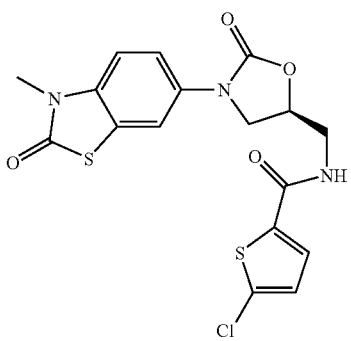

is obtained analogously from 6-[(5S)-5-(aminomethyl)-2-oxo-1,3-oxazolidin-3-yl]-3-methyl-1,3-benzothiazol-2(3H)-one (for preparation, see EP-A-738 726).

M.p.: 217° C.

Example 8

5-Chloro-N-[((5S)-3-{3-fluoro-4-[4-(4-pyridinyl)piperazino]phenyl}-2-oxo-1,3-oxazolidin-5-yl)methyl]-2-thiophenecarboxamide

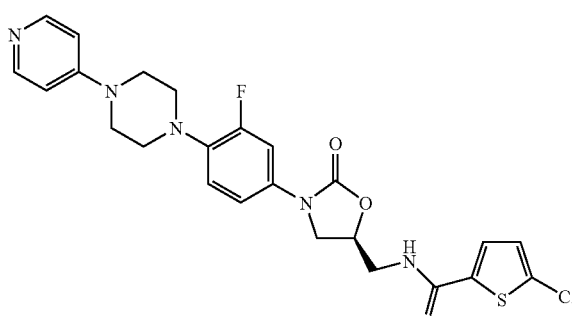

is obtained analogously from (5S)-5-(aminomethyl)-3-{3-fluoro-4-[4-(4-pyridinyl)piperazino]phenyl}-1,3-oxazolidin-2-one (preparation in analogy to J. A. Tucker et al., J. Med. Chem. 1998, 41, 3727).

MS (ESI) 516 (M+H), Cl pattern.

Example 9

5-Chloro-N-({(5S)-3-[3-fluoro-4-(4-methylpiperazino)phenyl]-2-oxo-1,3-oxazolidin-5-yl}methyl)-2-thiophenecarboxamide

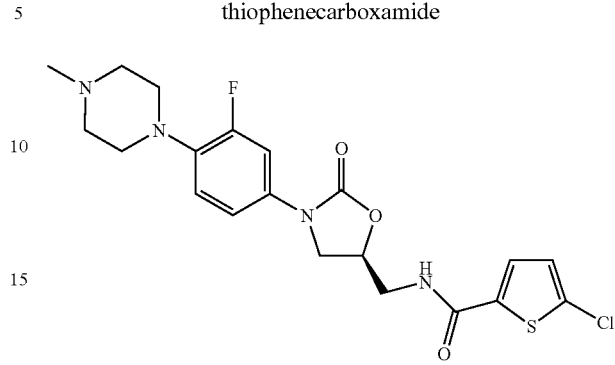

is obtained analogously from (5S)-5-(aminomethyl)-3-[3-fluoro-4-(4-methylpiperazino)phenyl]-1,3-oxazolidin-2-one.

Example 10

5-Chloro-N-({(5S)-3-[3-fluoro-4-(4-tert-butoxycarbonylpiperazin-1-yl)phenyl]-2-oxo-1,3-oxazolidin-5-yl}methyl)-2-thiophenecarboxamide

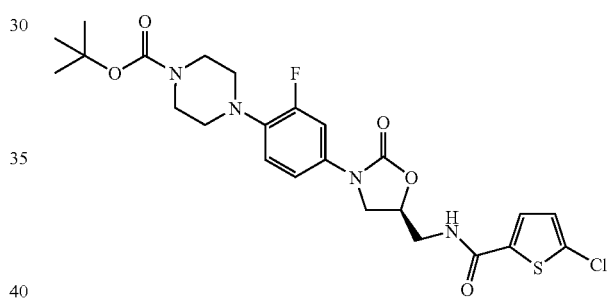

is obtained analogously from (5S)-5-(aminomethyl)-3-[3-fluoro-4-(4-tert-butoxy-carbonylpiperazin-1-yl)phenyl]-1,3-oxazolidin-2-one (for preparation, see WO-A-93/23384 which has already been cited).

M.p.: 184° C.; R$_f$(SiO$_2$, toluene/ethyl acetate 1:1)=0.42.

Example 11

5-Chloro-N-({(5S)-3-[3-fluoro-4-(piperazin-1-yl)phenyl]-2-oxo-1,3-oxazolidin-5-yl}methyl)-2-thiophenecarboxamide

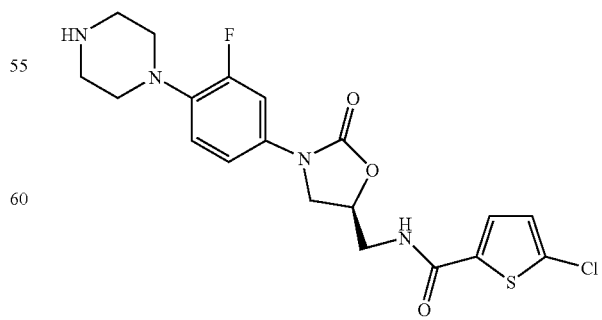

is obtained by reacting Example 12 with trifluoroacetic acid in methylene chloride.

IC$_{50}$=140 nM; $^1$H-NMR [d$_6$-DMSO]: 3.01-3.25 (m, 8H), 3.5-3.65 (m, 2H), 3.7-3.9 (m, 1H), 4.05-4.2 (m, 1H), 4.75-4.9 (m, 1H), 7.05-7.25 (m, 3H), 7.5 (dd, 1H), 7.7 (d, 1H), 8.4 (broad s, 1H), 9.0 (t, 1H).

Example 12

5-Chloro-N-[((5S)-3-(2,4'-bipyridinyl-5-yl)-2-oxo-1,3-oxazolidin-5-yl)methyl]-2-thiophenecarboxamide

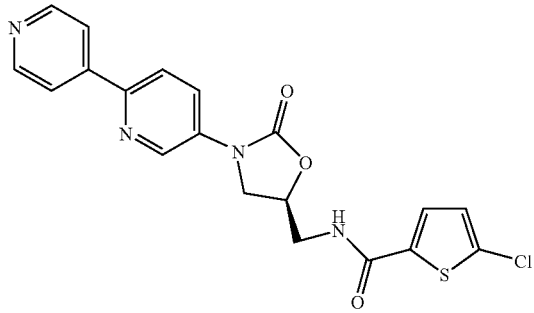

is obtained analogously from (5S)-5-aminomethyl-3-(2,4'-bipyridinyl-5-yl)-2-oxo-1,3-oxazolidin-2-one (for preparation, see EP-A-789 026).

R$_f$(SiO$_2$, ethyl acetate/ethanol 1:2)=0.6; MS (ESI) 515 (M+H), Cl pattern.

Example 13

5-Chloro-N-{[(5S)-2-oxo-3-(4-piperidinophenyl)-1,3-oxazolidin-5-yl]methyl}-2-thiophenecarboxamide

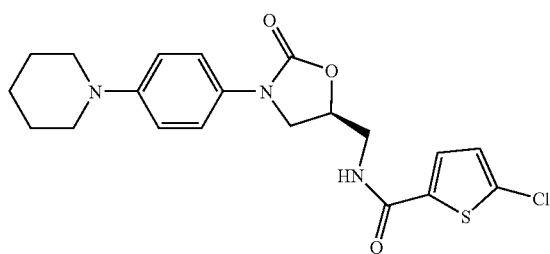

is obtained from 5-(hydroxymethyl)-3-(4-piperidinophenyl)-1,3-oxazolidin-2-one (for preparation, see DE 2708236) after mesylation, reaction with potassium phthalimide, hydrazinolysis and reaction with 5-chlorothiophene-2-carboxylic acid.

R$_f$(SiO$_2$, ethyl acetate/toluene 1:1)=0.31; M.p. 205° C.

Example 17

5-Chloro-N-({(5S)-2-oxo-3-[4-(2-oxo-1-pyrrolidinyl)phenyl]-1,3-oxazolidin-5-yl}methyl)-2-thiophenecarboxamide

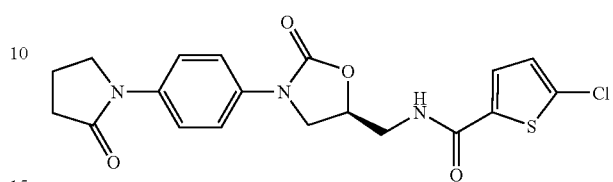

5-Chloro-N-({(5S)-2-oxo-3-[4-(2-oxo-1-pyrrolidinyl)phenyl]-1,3-oxazolidin-5-yl}methyl)-2-thiophenecarboxamide is obtained from 1-(4-aminophenyl)pyrrolidin-2-one (for preparation, see Reppe et al., Justus Liebigs Ann. Chem.; 596; 1955; 209) in analogy to the known synthesis scheme (see S. J. Brickner et al., J. Med. Chem. 1996, 39, 673) after reaction with benzyloxycarbonyl chloride, subsequent reaction with R-glycidyl butyrate, mesylation, reaction with potassium phthalimide, hydrazinolysis in methanol and finally reaction with 5-chlorothiophene-2-carboxylic acid. The 5-chloro-N-({(5S)-2-oxo-3-[4-(2-oxo-1-pyrrolidinyl)phenyl]-1,3-oxazolidin-5-yl}methyl)-2-thiophenecarboxamide obtained in this way has an IC$_{50}$ of 4 nM (test method for the IC$_{50}$ according to Example A-1. a.1) "Measurement of factor Xa inhibition" described above).

M.p.: 229° C.; R$_f$(SiO$_2$, toluene/ethyl acetate 1:1)=0.05 (precursor:=0.0); MS (ESI): 442.0 (21%, M+Na, Cl pattern), 420.0 (72%, M+H, Cl pattern), 302.3 (12%), 215 (52%), 145 (100%); $^1$H-NMR (d$_6$-DMSO, 300 MHz): 2.05 (m, 2H), 2.45 (m, 2H), 3.6 (t, 2H), 3.77-3.85 (m, 3H), 4.15 (t, 1H), 4.75-4.85 (m, 1H), 7.2 (d, 1H), 7.5 (d, 2H), 7.65 (d, 2H), 7.69 (d, 1H), 8.96 (t, 1H).

The individual stages in the synthesis of Example 17 described above, with the respective precursors, are as follows:

4.27 g (25.03 mmol) of benzyl chloroformate are slowly added to 4 g (22.7 mmol) of 1-(4-aminophenyl)pyrrolidin-2-one and 3.6 ml (28.4 mmol) of N,N-dimethylaniline in 107 ml of tetrahydrofuran at −20° C. The mixture is stirred at −20° C. for 30 minutes and then allowed to reach room temperature. 0.5 l of ethyl acetate is added, and the organic phase is washed with 0.5 l of saturated NaCl solution. The removed organic phase is dried with MgSO$_4$, and the solvent is evaporated in vacuo. The residue is triturated with diethyl ether and filtered off with suction. 5.2 g (73.8% of theory) of benzyl 4-(2-oxo-1-pyrrolidinyl)phenylcarbamate are obtained as pale beige crystals with a melting point of 174° C.

7.27 ml of a 2.5 M solution of n-butyllithium (BuLi) in hexane are added dropwise to 1.47 g (16.66 mmol) of isoamyl alcohol in 200 ml of tetrahydrofuran under argon at −10° C., a further 8 ml of the BuLi solution being necessary until the color of the added N-benzylidenebenzylamine indicator changed. The mixture is stirred at −10° C. for 10 minutes and cooled to −78° C., and a solution of 4.7 g (15.14 mmol) of benzyl 4-(2-oxo-1-pyrrolidinyl)phenylcarbamate is slowly added. Then a further 4 ml of n-BuLi solution are added until the color of the indicator changes, to pink. The mixture is stirred at −78° C. for 10 minutes and 2.62 g (18.17 mmol) of R-glycidyl butyrate are added, and the mixture is stirred at −78° C. for 30 minutes.

The mixture is allowed to reach room temperature overnight, 200 ml of water are added to the mixture, and the THF content is evaporated in vacuo. The aqueous residue is extracted with ethyl acetate, and the organic phase is dried with MgSO$_4$ and concentrated in vacuo. The residue is triturated with 500 ml of diethyl ether, and the crystals which have separated out are filtered off with suction in vacuo.

3.76 g (90% of theory) of (5R)-5-(hydroxymethyl)-3-[4-(2-oxo-1-pyrrolidinyl)phenyl]-1,3-oxazolidin-2-one are obtained with a melting point of 148° C. and an R$_f$(SiO$_2$, toluene/ethyl acetate 1:1)=0.04 (precursor=0.3).

3.6 g (13.03 mmol) of (5R)-5-(hydroxymethyl)-3-[4-(2-oxo-1-pyrrolidinyl)phenyl]-1,3-oxazolidin-2-one and 2.9 g (28.67 mmol) of triethylamine are introduced into 160 ml of dichloromethane at 0° C. with stirring. 1.79 g (15.64 mmol) of methanesulfonyl chloride are added with stirring, and the mixture is stirred at 0° C. for 1.5 hours and at room temperature for 3 h.

The reaction mixture is washed with water and the aqueous phase is extracted once more with methylene chloride. The combined organic extracts are dried with MgSO$_4$ and evaporated. The residue (1.67 g) is then dissolved in 70 ml of acetonitrile, 2.62 g (14.16 mmol) of potassium phthalimide are added, and the mixture is stirred in a closed vessel at 180° C. in a microwave oven for 45 minutes.

The mixture is filtered off from the insoluble residue, the filtrate is concentrated in vacuo, the residue (1.9 g) is dissolved in methanol, and 0.47 g (9.37 mmol) of hydrazine hydrate is added. The mixture is boiled for 2 hours and cooled, saturated sodium bicarbonate solution is added, and the mixture is extracted six times with a total of 2 l of methylene chloride. The combined organic extracts of the crude (5S)-5-(aminomethyl)-3-[4-(2-oxo-1-pyrrolidinyl)phenyl]-1,3-oxazolidin-2-one are dried with MgSO$_4$ and concentrated in vacuo.

The final stage, 5-chloro-N-({(5S)-2-oxo-3-[4-(2-oxo-1-pyrrolidinyl)phenyl]-1,3oxazolidin-5-yl}methyl)-2-thiophenecarboxamide, is prepared by dissolving 0.32 g (1.16 mmol) of the (5S)-5-(aminomethyl)-3-[4-(2-oxo-1-pyrrolidinyl)phenyl]-1,3-oxazolidin-2-one prepared above, 5-chlorothiophene-2-carboxylic acid (0.19 g; 1.16 mmol) and 1-hydroxy-1H-benzotriazole hydrate (HOBT) (0.23 g, 1.51 mmol) in 7.6 ml of DMF. 0.29 g (1.51 mmol) of N'-(3-dimethylaminopropyl)-N-ethylcarbodiimide (EDCI) is added and, at room temperature, 0.3 g (0.4 ml; 2.32 mmol, 2 equivalents) of diisopropylethylamine (DIEA) is added dropwise. The mixture is stirred at room temperature overnight.

The mixture is evaporated to dryness in vacuo, and the residue is dissolved in 3 ml of DMSO and chromatographed on an RP-MPLC with acetonitrile/water/0.5% TFA gradients. The acetonitrile content is evaporated off from the appropriate fractions, and the precipitated compound is filtered off with suction. 0.19 g (39% of theory) of the target compound is obtained.

The following were prepared in an analogous manner:

Example 18

5-Chloro-N-({(5S)-2-oxo-3-[4-(1-pyrrolidinyl)phenyl]-1,3-oxazolidin-5-yl}methyl)-2-thiophenecarboxamide The compound 5-chloro-N-({(5S)-2-oxo-3-[4-(1-pyrrolidinyl)phenyl]-1,3-oxazolidin-5-yl}methyl)-2-thiophenecarboxamide is obtained from 4-pyrrolidin-1-ylaniline (Reppe et al., Justus Liebigs Ann. Chem.; 596; 1955; 151) in analogy to Example 17.

IC$_{50}$=40 nM; M.p.: 216° C.; R$_f$(SiO$_2$, toluene/ethyl acetate 1:1)=0.31 [precursor:=0.0].

Example 19

5-Chloro-N-({(5S)-2-oxo-3-[4-(diethylamino)phenyl]-1,3-oxazolidin-5-yl}methyl)-2-thiophenecarboxamide The compound 5-chloro-N-({(5S)-2-oxo-3-[4-(diethylamino)phenyl]-1,3-oxazolidin-5-yl}methyl)-2-thiophenecarboxamide is obtained analogously from N,N-diethylphenyl-1,4-diamine (U.S. Pat. No. 2,811,555; 1955).

IC$_{50}$=270 nM; M.p.: 181° C.; R$_f$(SiO$_2$, toluene/ethyl acetate 1:1)=0.25 [precursor:=0.0].

Example 36

5-Chloro-N-({(5S)-3-[2-methyl-4-(4-morpholinyl)phenyl]-2-oxo-1,3-oxanzolidin-5-yl}methyl)-2-thiophenecarboxamide starting from 2-methyl-4-(4-morpholinyl)aniline (J. E. LuValle et al. J. Am. Chem. Soc. 1948, 70, 2223):

MS (ESI): m/z (%)=436 ([M+H]$^+$, 100), Cl pattern; HPLC (method 1): rt (%)=3.77 (98). IC$_{50}$: 1.26 µM.

Example 37

5-Chloro-N-{[(5S)-3-(3-chloro-4-morpholinophenyl)-2-oxo-1,3-oxazolidin-5-yl]methyl}-2-thiophenecarboxamide starting from 3-chloro-4-(4-morpholinyl)aniline (H. R. Snyder et al. J. Pharm. Sci. 1977, 66, 1204):

MS (ESI): m/z (%)=456 ([M+H]$^+$, 100), Cl$_2$ pattern; HPLC (method 2): rt (%)=4.31 (100). IC$_{50}$: 33 nM.

Example 38

5-Chloro-N-({(5S)-3-[4-(4-morpholinylsulfonyl)phenyl]-2-oxo-1,3-oxazolidin-5-yl}methyl)-2-thiophenecarboxamide starting from 4-(4-morpholinylsulfonyl)aniline (Adams et al. J. Am. Chem. Soc. 1939, 61, 2342):

MS (ESI): m/z (%)=486 ([M+H]$^+$, 100), Cl pattern; HPLC (method 3): rt (%)=4.07 (100). IC$_{50}$: 2 µM.

Example 39

5-Chloro-N-({(5S)-3-[4-(1-azetidinylsulfonyl)phenyl]-2-oxo-1,3-oxazolidin-5-yl}methyl)-2-thiophenecarboxamide starting from 4-(1-azetidinylsulfonyl)aniline:

MS (DCI, NH$_3$): m/z (%)=473 ([M+NH$_4$]$^+$, 100), Cl pattern; HPLC (method 3): rt (%)=4.10 (100). IC$_{50}$: 0.84 µM.

Example 40

5-Chloro-N-[((5S)-3-{4-[(dimethylamino)sulfonyl]phenyl}-2-oxo-1,3-oxazolidin-5-yl)methyl]-2-thiophenecarboxamide starting from 4-amino-N,N-dimethylbenzenesulfonamide (I. K. Khanna et al. J. Med. Chem. 1997, 40, 1619):

MS (ESI): m/z (%)=444 ([M+H]$^+$, 100), Cl pattern; HPLC (method 3): rt (%)=4.22 (100). IC$_{50}$: 90 nM.

General method for the acylation of 5-(aminomethyl)-3-[4-(2-oxo-1-pyrrolidinyl)phenyl]-1,3-oxazolidin-2-one with carbonyl chlorides.

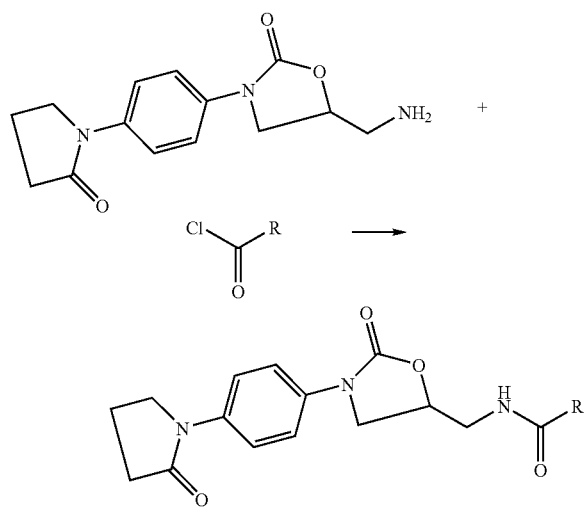

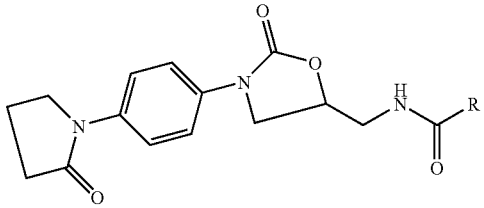

An approx. 0.1 molar solution of 5-(aminomethyl)-3-[4-(2-oxo-1-pyrrolidinyl)phenyl]-1,3-oxazolidin-2-one (from Example 45) (1.0 eq.) and absolute pyridine (approx. 6 eq) in absolute dichloromethane is added dropwise to the appropriate acid chloride (2.5 eq.) under argon at room temperature. The mixture is stirred at room temperature for about 4 h before approx. 5.5 eq of PS-trisamine (Argonaut Technologies) are added. The suspension is stirred gently for 2 h and, after dilution with dichloromethane/DMF (3:1), filtered (the resin is washed with dichloromethane/DMF) and the filtrate is concentrated. The resulting product is purified by preparative RP-HPLC where appropriate.

The following was prepared in an analogous manner:

Example 41

N-({2-oxo-3-[4-(2-oxo-1-pyrrolidinyl)phenyl]-1,3-oxazolidin-5-yl}methyl)-2-thiophenecarboxamide LC-MS (method 6): m/z (%)=386 (M+H, 100); LC-MS: rt (%)=3.04 (100). $IC_{50}$: 1.3 µM.

General method for preparing acyl derivatives starting from 5-(aminomethyl)-3-[4-(2-oxo-1-pyrrolidinyl)phenyl]-1,3-oxazolidin-2-one and carboxylic acids

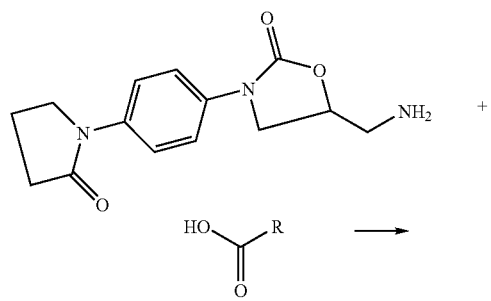

The appropriate carboxylic acid (approx. 2 eq) and a mixture of absolute dichloromethane/DMF (approx. 9:1) are added to 2.9 eq. of resin-bound carbodiimide (PS-Carbodiimide, Argonaut Technologies). After shaking gently at room temperature for about 15 min, 5-(aminomethyl)-3-[4-(2-oxo-1-pyrrolidinyl)phenyl]-1,3-oxazolidin-2-one (from Example 45) (1.0 eq.) is added, and the mixture is shaken overnight before the resin is filtered off (washing with dichloromethane) and the filtrate is concentrated. The resulting product is purified by preparative RP-HPLC where appropriate.

The following were prepared in an analogous manner:

Example 42

5-Methyl-N-({2-oxo-3-[4-(2-oxo-1-pyrrolidinyl)phenyl]-1,3-oxazolidin-5-yl}methyl)-2-thiophenecarboxamide LC-MS: m/z (%)=400 (M+H, 100); LC-MS (method 6): rt (%)=3.23 (100). $IC_{50}$: 0.16 µM.

Example 43

5-Bromo-N-({2-oxo-3-[4-(2-oxo-1-pyrrolidinyl)phenyl]-1,3-oxazolidin-5-yl}methyl)-2-thiophenecarboxamide LC-MS: m/z (%)=466 (M+H, 100); LC-MS (method 5): rt (%)=3.48 (78). $IC_{50}$: 0.014 µM.

Example 44

5-Chloro-N-({(5S)-2-oxo-3-[4-(3-oxo-4-morpholinyl)phenyl]-1,3-oxazolidin-5-yl}methyl)-2-thiophenecarboxamide

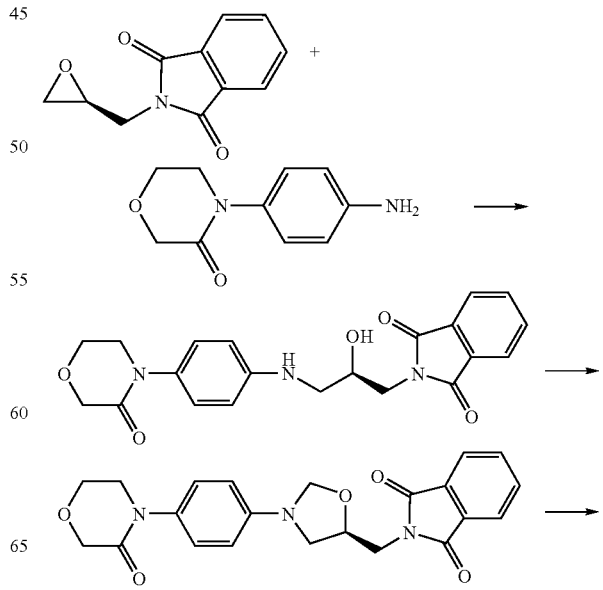

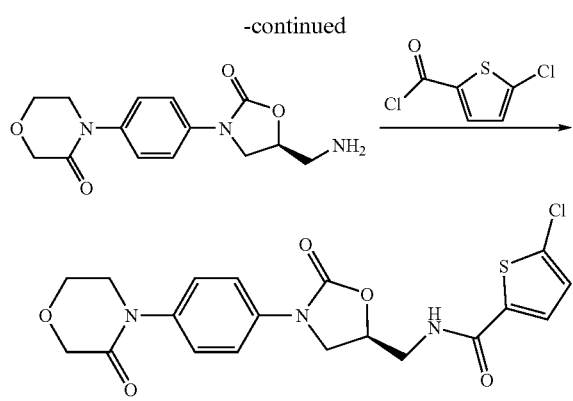

a) 2-((2R)-2-Hydroxy-3-{[4-(3-oxo-4-morpholinyl)phenyl]amino}propyl)-1H-isoindole-1,3(2H)-dione:

A suspension of 2-[(2S)-2-oxiranylmethyl]-1H-isoindole-1,3(2H)-dione (A. Gutcait et al. *Tetrahedron Asym.* 1996, 7, 1641) (5.68 g, 27.9 mmol) and-4-(4-aminophenyl)-3-morpholinone (5.37 g, 27.9 mmol) in ethanol/water (9:1, 140 ml) is refluxed for 14 h (the precipitate dissolves and, after some time, there is renewed formation of a precipitate). The precipitate (desired product) is filtered off, washed three times with diethyl ether and dried. The combined mother liquers are concentrated in vacuo and, after addition of a second portion of 2-[(2S)-2-oxiranylmethyl]-1H-isoindole-1,3(2h)-dione (2.84 g, 14.0 mmol), are suspended in ethanol/water (9:1, 70 ml) and refluxed for 13 h (the precipitate dissolves and, after some time, there is renewed formation of a precipitate). The precipitate (desired product) is filtered off, washed three times with diethyl ether and dried. Overall yield: 10.14 g, 92% of theory.

MS (ESI): m/z (%)=418 ([M+Na]$^+$, 84), 396 ([M+H]$^+$, 93); HPLC (method 3): rt (%)=3.34 (100).

b) 2-({(5S)-2-Oxo-3-[4-(3-oxo-4-morpholinyl)phenyl]-1,3-oxazolidin-5-yl}methyl)-1H-isoindole-1,3(2H)-dione:

N,N'-Carbonyldiimidazole (2.94 g, 18.1 mmol) and dimethylaminopyridine (catalytic amount) are added to a suspension of the amino alcohol (3.58 g, 9.05 mmol) in tetrahydrofuran (90 ml) under argon at room temperature. The reaction suspension is stirred at 60° C. for 12 h (the precipitate dissolves and, after some time, there is renewed formation of a precipitate), a second portion of N,N'-carbonyldiimidazole (2.94 g, 18.1 mmol) is added, and the mixture is stirred at 60° C. for a further 12 h. The precipitate (desired product) is filtered off, washed with tetrahydrofuran and dried. The filtrate is concentrated in vacuo and further product is purified by flash chromatography (dichloromethane/methanol mixtures). Overall yield: 3.32 g, 87% of theory.

MS (ESI): m/z (%)=422 ([M+H]$^+$, 100); HPLC (method 4): rt (%)=3.37 (100).

c) 5-Chloro-N-({(5S)-2-oxo-3-[4-(3-oxo-4-morpholinyl)phenyl]-1,3-oxazolidin-5-yl}methyl)-2-thiophenecarboxamide:

Methylamine (40% strength in water, 10.2 ml, 0.142 mol) is added dropwise to a suspension of the oxazolidinone (4.45 g, 10.6 mmol) in ethanol (102 ml) at room temperature. The reaction mixture is refluxed for 1 h and concentrated in vacuo. The crude product is employed without further purification in the next reaction.

5-Chlorothiophene-2-carbonyl chloride (2.29 g, 12.7 mmol) is added dropwise to a solution of the amine in pyridine (90 ml) under argon at 0° C. The ice cooling is removed and the reaction mixture is stirred at room temperature for 1 h, and water is added. Addition of dichloromethane and phase separation are followed by extraction of the aqueous phase with dichloromethane. The combined organic phases are dried (sodium sulfate), filtered and concentrated in vacuo. The desired product is purified by flash chromatography (dichloromethane/methanol mixtures). Overall yield: 3.92 g, 86% of theory.

M.p.: 232-233° C.; $^1$H NMR (DMSO—d$^6$, 200 MHz): 9.05-8.90 (t, J=5.8 Hz, 1H), 7.70 (d, J=4.1 Hz, 1H), 7.56 (d, J=9.0 Hz, 2H), 7.41 (d, J=9.0 Hz, 2H), 7.20 (d, J=4.1 Hz, 1H), 4.93-4.75 (m, 1H), 4.27-4.12 (m, 3H), 4.02-3.91 (m, 2H), 3.91-3.79 (dd, J=6.1 Hz, 9.2 Hz, 1H), 3.76-3.66 (m, 2H), 3.66-3.54 (m, 2H); MS (ESI): m/z (%)=436 ([M+H]$^+$, 100, Cl pattern); HPLC (method 2): rt (%)=3.60 (100); [α]$^{21}_D$=−38° (c 0.2985, DMSO); ee: 99%. IC$_{50}$: 0.7 nM.

The following were prepared in an analogous manner:

Example 45

5-Methyl-N-({(5S)-2-oxo-3-[4-(3-oxo-4-morpholinyl)phenyl]-1,3-oxazolidin-5-yl}methyl)-2-thiophenecarboxamide MS (ESI): m/z (%)=831 ([2M+H]$^+$, 100), 416 ([M+H]$^+$, 66); HPLC (method 3): rt (%)=3.65 (100). IC$_{50}$: 4.2 nM.

Example 46

5-Bromo-N-({(5S)-2-oxo-3-[4-(3-oxo-4-morpholinyl)phenyl]-1,3-oxazolidin-5-yl}methyl)-2-thiophenecarboxamide MS (ESI): m/z (%)=480 ([M+H]$^+$, 100, Br pattern); HPLC (method 3): rt (%)=3.87 (100). IC$_{50}$: 0.3 nM.

Example 47

5-Chloro-N-{[(5S)-3-(3-isopropyl-2-oxo-2,3-dihydro-1,3-benzoxazol-6-yl)-2-oxo-1,3-oxazolidin-5-yl]methyl}-2-thiophenecarboxamide

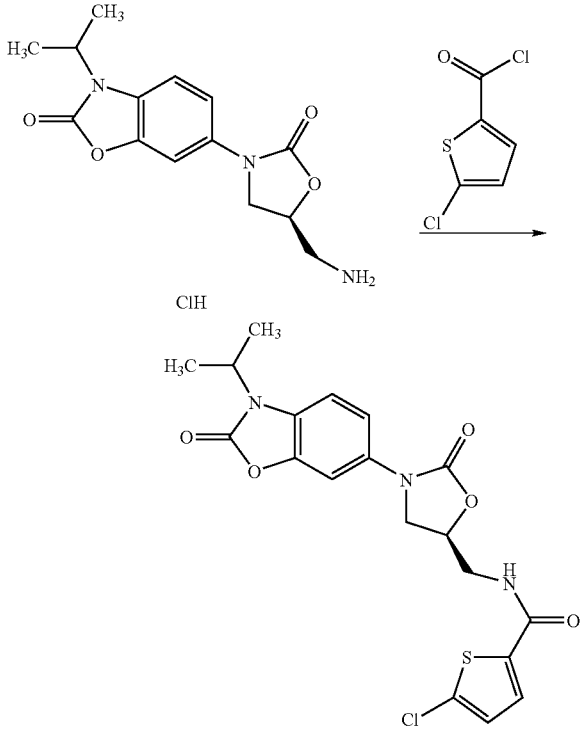

200 mg (0.61 mmol) of 6-[(5S)-5-(aminomethyl)-2-oxo-1,3-oxazolidin-3-yl]-3-isopropyl-1,3-benzoxazol-2(3H)-one hydrochloride (EP 738726) are suspended in 5 ml of tetrahydrofuran, and 0.26 ml (1.83 mmol) of triethylamine and 132 mg (0.73 mmol) of 5-chlorothiophene-2-carbonyl chloride are added. The reaction mixture is stirred at room temperature overnight and then concentrated. The product is isolated by column chromatography (silica gel, methylene chloride/ethanol=50/1 to 20/1). 115 mg (43% of theory) of the desired compound are obtained.

MS (ESI): m/z (%)=436 (M+H, 100); HPLC (method 4): rt=3.78 min.

The compounds were prepared in an analogous manner:

| Example No. | Structure | M.p. [° C.] | IC$_{50}$ [μM] |
|---|---|---|---|
| 48 | 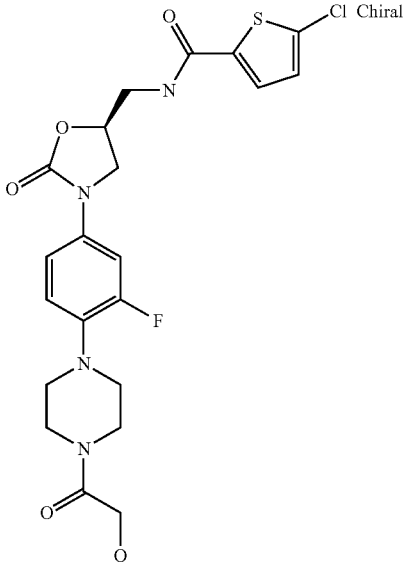 Chiral | 210 | 0.12 |
| 49 | 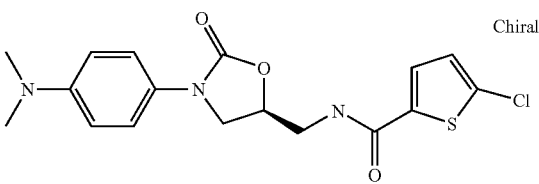 Chiral | 234 | 0.074 |
| 50 | 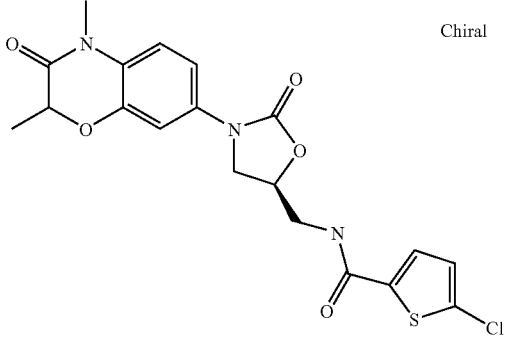 Chiral | 195 | 1.15 |
| 51 | 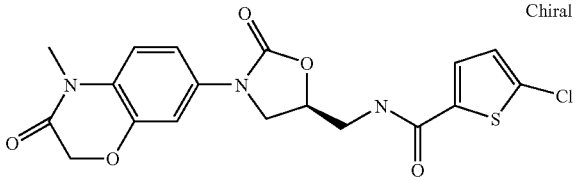 Chiral | 212 | 1.19 |

-continued

| Example No. | Structure | M.p. [° C.] | IC$_{50}$ [μM] |
|---|---|---|---|
| 52 | Chiral; with trifluoroacetate counterion | 160 | 0.19 |
| 53 | Chiral | MS (ESI): m/z (%) = 431 ([M + H]$^+$, 100), Cl pattern | 0.74 |
| 54 | Chiral; from 5-amino-2-pyrrolidinobenzonitrile (Grell, W., Hurnaus, R.; Griss, G., Sauter, R.; Rupprecht, E. et al.; J. Med. Chem. 1998, 41; 5219) | 221 | 0.13 |
| 55 | Chiral; from 3-(4-aminophenyl)-oxazolidin-2-one (Artico, M. et al.; Farmaco Ed. Sci. 1969, 24; 179) | 256 | 0.04 |
| 56 | Chiral | 218 | 0.004 |
| 57 | Chiral | 226 | 0.58 |
| 58 | 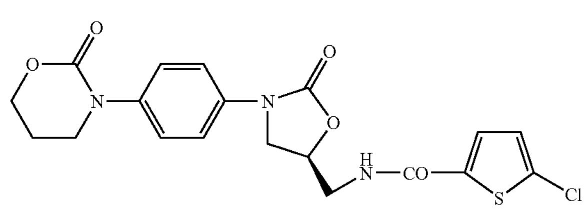 | 228-230 |  |

Examples 20 to 30 and 58 to 139 which follow relate to process variant [B], with Examples 20 and 21 describing the preparation of precursors.

Example 20

Preparation of N-allyl-5-chloro-2-thiophenecarboxamide

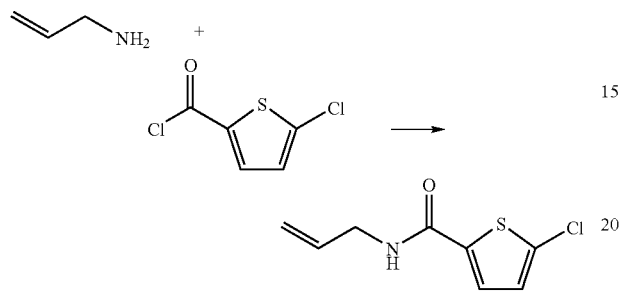

5-Chlorothiophene-2-carbonyl chloride (7.61 g, 42 mmol) is added dropwise to an ice-cooled solution of 2.63 ml (35 mmol) of allylamine in 14.2 ml of absolute pyridine and 14.2 ml of absolute THF. The ice cooling is removed and the mixture is stirred at room temperature for 3 h before being concentrated in vacuo. Water is added to the residue, and the solid is filtered off. The crude product is purified by flash chromatography on silica gel (dichloromethane).

Yield: 7.20 g (99% of theory); MS (DCI, $NH_4$): m/z (%)=219 (M+$NH_4$, 100), 202 (M+H, 32); HPLC (method 1): rt (%)=3.96 min (98.9).

Example 21

Preparation of 5-chloro-N-(2-oxiranylmethyl)-2-thiophenecarboxamide

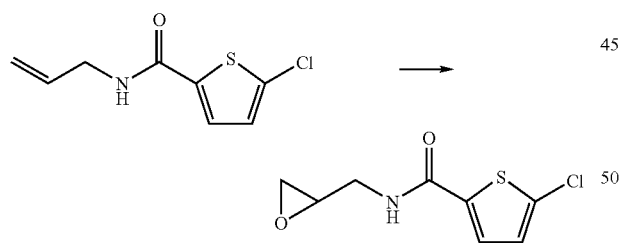

meta-Chloroperbenzoic acid (3.83 g, approx. 60% pure) is added to an ice-cooled solution of 2.0 g (9.92 mmol) of N-allyl-5-chloro-2-thiophenecarboxamide in 10 ml of dichloromethane. The mixture is stirred overnight while warming to room temperature, and then washed with 10% sodium bisulfate solution (three times). The organic phase is washed with saturated sodium bicarbonate solution (twice) and with saturated sodium chloride solution, dried over magnesium sulfate and concentrated. The product is purified by chromatography on silica gel (cyclohexane/ethyl acetate 1:1).

Yield: 837 mg (39% of theory); MS (DCI, $NH_4$): m/z (%)=253 (M+$NH_4$, 100), 218 (M+H, 80); HPLC (method 1): rt (%)=3.69 min (approx. 80).

General method for preparing substituted N-(3-amino-2-hydroxypropyl)-5-chloro-2-thiophenecarboxamide derivatives starting from 5-chloro-N-(2-oxiranylmethyl)-2-thiophenecarboxamide

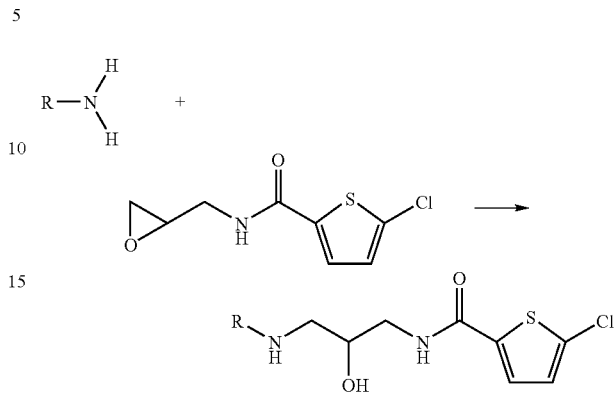

5-Chloro-N-(2-oxiranylmethyl)-2-thiophenecarboxamide (1.0 eq.) is added in portions to a solution of primary amine or aniline derivative (1.5 to 2.5 eq.) in 1,4-dioxane, 1,4-dioxane/water mixtures or ethanol, ethanol/water mixtures (approx. 0.3 to 1.0 mol/l) at room temperature or at temperatures up to 80° C. The mixture is stirred for 2 to 6 hours before being concentrated. The product can be isolated from the reaction mixture by chromatography on silica gel (cyclohexane/ethyl acetate mixtures, dichloromethane/methanol mixtures or dichloromethane/methanol/triethylamine mixtures).

The following were prepared in an analogous manner:

Example 22

N-[3-(Benzylamino)-2-hydroxypropyl]-5-chloro-2-thiophenecarboxamide

MS (ESI): m/z (%)=325 (M+H, 100); HPLC (method 1): rt (%)=3.87 min (97.9).

Example 23

5-Chloro-N-[3-(3-cyanoanilino)-2-hydroxypropyl]-2-thiophenecarboxamide

MS (ESI): m/z (%)=336 (M+H, 100); HPLC (method 2): rt (%)=4.04 min (100).

Example 24

5-Chloro-N-[3-(4-cyanoanilino)-2-hydroxypropyl]-2-thiophenecarboxamide

MS (ESI): m/z (%)=336 (M+H, 100); HPLC (method 1): rt (%)=4.12 min (100).

Example 25

5-Chloro-N-{3-[4-(cyanomethyl)anilino]-2-hydroxypropyl}-2-thiophenecarboxamide

MS (ESI): m/z (%)=350 (M+H, 100); HPLC (method 4): rt (%)=3.60 min (95.4).

Example 26

5-Chloro-N-{3-[3-(cyanomethyl)anilino]-2-hydroxypropyl}-2-thiophenecarboxamide

MS (ESI): m/z (%)=350 (M+H, 100); HPLC (method 4): rt (%)=3.76 min (94.2).

Example 58 tert-Butyl 4-[(3-{[(5-chloro-2-thienyl)carbonyl]
amino}-2-hydroxypropyl)amino]-benzylcarbamate Starting from tert-butyl 4-aminobenzylcarbamate (*Bioorg. Med. Chem. Lett.*; 1997; 1921-1926):

MS (ES-pos): m/z (%)=440 (M+H, 100), (ES-neg): m/z (%)=438 (M−H, 100); HPLC (method 1): rt (%)=4.08 (100).

Example 59 tert-Butyl 4-[(3-{[(5-chloro-2-thienyl)carbonyl]
amino}-2-hydroxypropyl)amino]-phenylcarbamate Starting from N-tert-butyloxycarbonyl-1,4-phenylenediamine:

MS (ESI): m/z (%)=426 (M+H, 45), 370 (100); HPLC (method 1): rt (%)=4.06 (100).

Example 60 tert-Butyl 2-hydroxy-3-{[4-(2-oxo-1-pyrrolidinyl)
phenyl]amino}propyl-carbamate

Starting from 1-(4-aminophenyl)-2-pyrrolidinone (*Justus Liebigs Ann. Chem.*; 1955; 596; 204):

MS (DCI, $NH_3$): m/z (%)=350 (M+H, 100); HPLC (method 1): rt (%)=3.57 (97).

Example 61

5-Chloro-N-(3-{[3-fluoro-4-(3-oxo-4-morpholinyl)
phenyl]amino}-2-hydroxypropyl)-2-thiophenecarboxamide 800 mg (3.8 mmol) of 4-(4-amino-2-fluorophenyl)-3-morpholinone and 700 mg (3.22 mmol) of 5-chloro-N-(2-oxiranylmethyl)-2-thiophenecarboxamide are heated in 15 ml of ethanol and 1 ml of water under reflux for 6 hours. The mixture is evaporated in vacuo, the crystals which have separated out after treatment with ethyl acetate are filtered off with suction, and chromatography of the mother liquor results in 276 mg (17% of theory) of the target compound.

$R_f$(ethyl acetate): 0.25.

Example 62

(N-(3-Anilino-2-hydroxypropyl)-5-chloro-2-
thiophenecarboxamide starting from aniline:
MS (DCI, $NH_3$): m/z (%)=311 ([M+H]$^+$, 100), Cl pattern; HPLC (method 3): rt (%)=3.79 (100).

Example 63

5-Chloro-N-(2-hydroxy-3-{[4-(3-oxo-4-morpholinyl)phenyl]amino}propyl)-2-thiophenecarboxamide starting from 4-(4-aminophenyl)-3-morpholinone:
MS(ESI): m/z (%)=410 ([M+H]$^+$, 50), Cl pattern; HPLC (method 3): rt (%)=3.58 (100).

Example 64

N-[3-({4-[Acetyl(cyclopropyl)amino]
phenyl}amino)-2-hydroxypropyl]-5-chloro-2-
thiophenecarboxamide starting from N-(4-aminophenyl)-N-cyclopropylacetamide:
MS (ESI): m/z (%)=408 ([M+H]$^+$, 100), Cl pattern; HPLC (method 3): rt (%)=3.77 (100).

Example 65

N-[3-({4-[Acetyl(methyl)amino]phenyl}amino)-2-
hydroxypropyl]-5-chloro-2-thiophenecarboxamide starting from N-(4-aminophenyl)-N-methylacetamide:
MS (ESI): m/z (%)=382 (M+H, 100); HPLC (method 4): rt=3.31 min.

Example 66

5-Chloro-N-(2-hydroxy-3-{[4-(1H-1,2,3-triazol-1-
yl)phenyl]amino}propyl)-2-thiophenecarboxamide starting from 4-(1H-1,2,3-triazol-1-yl)aniline (Bouchet et al.; J. Chem. Soc. Perkin Trans.2; 1974; 449):
MS (ESI): m/z (%)=378 (M+H, 100); HPLC (method 4): rt=3.55 min.

Example 67

Tert-butyl 1-{4-[(3-{[(5-chloro-2-thienyl)carbonyl]
amino}-2-hydroxypropyl)-amino]phenyl}-L-prolinate MS (ESI): m/z (%)=480 (M+H, 100); HPLC (method 4): rt=3.40 min.

Example 68

1-{4-[(3-{[(5-Chloro-2-thienyl)carbonyl]amino}-2-
hydroxypropyl)amino]phenyl}-4-piperidinecarboxamide MS (ESI): m/z (%)=437 (M+H, 100); HPLC (method 4): rt=2.39 min.

Example 69

1-{4-[(3-{[(5-Chloro-2-thienyl)carbonyl]amino}-2-
hydroxypropyl)-amino]phenyl}-3-piperidinecarboxamide MS (ESI): m/z (%)=437 (M+H, 100); HPLC (method 4): rt=2.43 min.

Example 70

5-Chloro-N-(2-hydroxy-3-{[4-(4-oxo-1-piperidinyl)
phenyl]amino}propyl)-2-thiophenecarboxamide MS (ESI): m/z (0%)=408 (M+H, 100); HPLC (method 4): rt=2.43 min.

Example 71

1-{4-[(3-{[(5-Chloro-2-thienyl)carbonyl]amino}-2-
hydroxypropyl)amino]phenyl}-L-prolinamide MS (ESI): m/z (%)=423 (M+H, 100); HPLC (method 4): rt=2.51 min.

Example 72

5-Chloro-N-[2-hydroxy-3-({4-[3-(hydroxymethyl)-1-piperidinyl]phenyl}-amino)propyl]-2-thiophenecarboxamide MS (ESI): m/z (%)=424 (M+H, 100); HPLC (method 4): rt=2.43 min.

Example 73

5-Chloro-N-[2-hydroxy-3-({4-[2-(hydroxymethyl)-1-piperidinyl]phenyl}-amino)propyl]-2-thiophenecarboxamide MS (ESI): m/z (%)=424 (M+H, 100); HPLC (method 4): rt=2.49 min.

Example 74

Ethyl 1-{4-[(3-{[(5-chloro-2-thienyl)carbonyl]amino}-2-hydroxypropyl)amino]phenyl}-2-piperidinecarboxylate MS (ESI): m/z (%)=466 (M+H, 100);. HPLC (method 4): rt=3.02 min.

Example 75

5-Chloro-N-[2-hydroxy-3-({4-[2-(hydroxymethyl)-1-pyrrolidinyl]phenyl}amino)propyl]-2-thiophenecarboxamide MS (ESI): m/z (%)=410 (M+H, 100); HPLC (method 4): rt=2.48 min.

Example 76

5-Chloro-N-(2-hydroxy-3-{[4-(2-methylhexahydro-5H-pyrrolo[3,4-d]isoxazol-5-yl)phenyl]amino}propyl)-2-thiophenecarboxamide MS (ESI): m/z (%)=437 (M+H, 100). HPLC (method 5): rt=1.74 min.

Example 77

5-Chloro-N-(2-hydroxy-3-{[4-(1-pyrrolidinyl)-3-(trifluoromethyl)phenyl]-amino}propyl)-2-thiophenecarboxamide MS (ESI): m/z (%)=448 (M+H, 100); HPLC (method 4): rt=3.30 min.

Example 78

5-Chloro-N-(2-hydroxy-3-{[4-(2-oxo-1-pyrrolidinyl)-3-(trifluoromethyl)phenyl]-amino}propyl)-2-thiophenecarboxamide MS (ESI): m/z (%)=462 (M+H, 100); HPLC (method 4): rt=3.50 min.

Example 79

5-Chloro-N-(3-{[3-chloro-4-(3-oxo-4-morpholinyl)phenyl]amino}-2-hydroxypropyl)-2-thiophenecarboxamide MS (ESI): m/z (%)=444 (M+H, 100); HPLC (method 4): rt=3.26 min.

Example 80

5-Chloro-N-(2-hydroxy-3-{[4-(3-oxo-4-morpholinyl)-3-(trifluoromethyl)phenyl]-amino}propyl)-2-thiophenecarboxamide MS (ESI): m/z (%)=478 (M+H, 100); HPLC (method 4): rt=3.37 min.

Example 81

5-Chloro-N-(2-hydroxy-3-{[3-methyl-4-(3-oxo-4-morpholinyl)phenyl]amino}-propyl)-2-thiophenecarboxamide MS (ESI): m/z (%)=424 (M+H, 100); HPLC (method 4): rt=2.86 min.

Example 82

5-Chloro-N-(3-{[3-cyano-4-(3-oxo-4-morpholinyl)phenyl]amino}-2-hydroxypropyl)-2-thiophenecarboxamide MS (ESI): m/z (%)=435 (M+H, 100); HPLC (method 4): rt=3.10 min.

Example 83

5-Chloro-N-(3-{[3-chloro-4-(1-pyrrolidinyl)phenyl]amino}-2-hydroxypropyl)-2-thiophenecarboxamide MS (ESI): m/z (%)=414 (M+H, 100); HPLC (method 4): rt=2.49 min.

Example 84

5-Chloro-N-(3-{[3-chloro-4-(2-oxo-1-pyrrolidinyl)phenyl]amino}-2-hydroxypropyl)-2-thiophenecarboxamide MS (ESI): m/z (%)=428 (M+H, 100); HPLC (method 4): rt=3.39 min.

Example 85

5-Chloro-N-(3-{[3,5-dimethyl-4-(3-oxo-4-morpholinyl)phenyl]amino}-2-hydroxypropyl)-2-thiophenecarboxamide MS (ESI): m/z (%)=438 (M+H, 100); HPLC (method 4): rt=2.84 min.

Example 86

N-(3-{[3-(Aminocarbonyl)-4-(4-morpholinyl)phenyl]amino}-2-hydroxypropyl)-5-chloro-2-thiophenecarboxamide MS (ESI): m/z (%)=439 (M+H, 100); HPLC (method 4): rt=2.32 min.

Example 87

5-Chloro-N-(2-hydroxy-3-{[3-methoxy-4-(4-morpholinyl)phenyl]amino}propyl)-2-thiophenecarboxamide MS (ESI): m/z (%)=426 (M+H, 100); HPLC (method 4): rt=2.32 min.

Example 88

N-(3-{[3-Acetyl-4-(4-morpholinyl)phenyl]amino}-2-hydroxypropyl)-5-chloro-2-thiophenecarboxamide MS (ESI): m/z (%)=438 (M+H, 100); HPLC (method 4): rt=2.46 min.

Example 89

N-(3-{[3-Amino-4-(3-oxo-4-morpholinyl)phenyl]amino}-2-hydroxypropyl)-5-chloro-2-thiophenecarboxamide MS (ESI): m/z (%)=425 (M+H, 100); HPLC (method 4): rt=2.45 min.

Example 90

5-Chloro-N-(3-{[3-chloro-4-(2-methyl-3-oxo-4-morpholinyl)phenyl]amino}-2-hydroxypropyl)-2-thiophenecarboxamide MS (ESI): m/z (%)=458 (M+H, 100); HPLC (method 4): rt=3.44 min.

Example 91

5-Chloro-N-(3-{[3-chloro-4-(2-methyl-5-oxo-4-morpholinyl)phenyl]amino}-2-hydroxypropyl)-2-thiophenecarboxamide MS (ESI): m/z (%)=458 (M+H, 100); HPLC (method 4): rt=3.48 min.

Example 91a

5-Chloro-N-[2-hydroxy-3-({4-[(3-oxo-4-morpholinyl)methyl]phenyl}amino)propyl]-2-thiophenecarboxamide Starting from 4-(4-aminobenzyl)-3-morpholinone (Surrey et al.; J. Amer. Chem. Soc.; 77; 1955; 633):
MS (ESI): m/z (%)=424 (M+H, 100); HPLC (method 4): rt=2.66 min.

General method for preparing 3-substituted 5-chloro-N-[(2-oxo-1,3-oxazolidin-5-yl)methyl]-2-thiophenecarboxamide derivatives starting from substituted N-(3-amino-2-hydroxypropyl)-5-chloro-2-thiophenecarboxamide derivatives

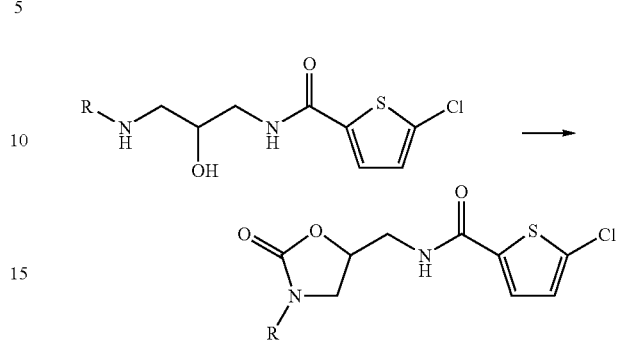

Carbodiimidazole (1.2 to 1.8 eq.) or a comparable phosgene equivalent is added to a solution of substituted N-(3-amino-2-hydroxypropyl)-5-chloro-2-thiophenecarboxamide derivative (1.0 eq.) in absolute THF (approx. 0.1 mol/l) at room temperature. The mixture is stirred at room temperature or, where appropriate, at elevated temperature (up to 70° C.) for 2 to 18 h before being concentrated in vacuo. The product can be purified by chromatography on silica gel (dichloromethane/methanol mixtures or cyclohexane/ethyl acetate mixtures).

The following were prepared in an analogous manner:

Example 27

N-[(3-Benzyl-2-oxo-1,3-oxazolidin-5-yl)methyl]-5-chloro-2-thiophenecarboxamide

MS (DCI, NH$_4$): m/z (%)=372 (M+Na, 100), 351 (M+H, 45); HPLC (method 1): rt (%)=4.33 min (100).

Example 28

5-Chloro-N-{[3-(3-cyanophenyl)-2-oxo-1,3-oxazolidin-5-yl]methyl}-2-thiophenecarboxamide MS (DCI, NH$_4$): m/z (%)=362 (M+H, 42); 145 (100); HPLC (method 2): rt (%)=4.13 min (100).

Example 29

5-Chloro-N-({3-[4-(cyanomethyl)phenyl]-2-oxo-1,3-oxazolidin-5-yl}methyl)-2-thiophenecarboxamide MS (ESI): m/z (%)=376 (M+H, 100); HPLC (method 4): rt=4.12 min.

Example 30

5-Chloro-N-({3-[3-(cyanomethyl)phenyl]-2-oxo-1,3-oxazolidin-5-yl}methyl)-2-thiophenecarboxamide MS (ESI): m/z (%)=376 (M+H, 100); HPLC (method 4): rt=4.17 min.

Example 92 tert-Butyl 4-[5-({[(5-chloro-2-thienyl)carbonyl]amino}methyl)-2-oxo-1,3-oxazolidin-3-yl]benzylcarbamate starting from Example 58:
MS (ESI): m/z (%)=488 (M+Na, 23), 349 (100); HPLC (method 1): rt (%)=4.51 (98.5).

Example 93 tert-Butyl 4-[5-({[(5-chloro-2-thienyl)carbonyl]amino}methyl)-2-oxo-1,3-oxazolidin-3-yl]phenylcarbamate starting from Example 59:
MS (ESI): m/z (%)=493 (M+Na, 70), 452 (M+H, 10), 395 (100); HPLC (method 1): rt (%)=4.41 (100).

Example 94 tert-Butyl 2-oxo-3-[4-(2-oxo-1-pyrrolidinyl)phenyl]-1,3-oxazolidin-5-yl}methylcarbamate starting from Example 60:
MS (DCI, NH$_3$): m/z (%)=393 (M+NH$_4$, 100); HPLC (method 3): rt (%)=3.97 (100).

Example 95

5-Chloro-N-({3-[3-fluoro-4-(3-oxo-4-morpholinyl)phenyl]-2-oxo-1,3-oxazolidin-5-yl}methyl)-2-thiophenecarboxamide

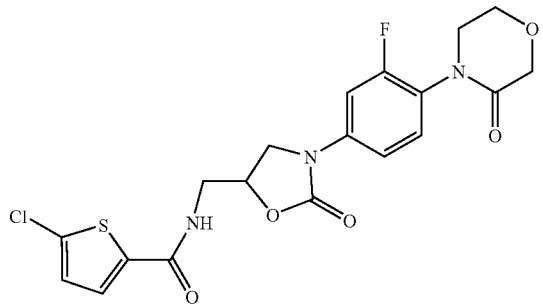

260 mg (0.608 mmol) of 5-chloro-N-(3-{[3-fluoro-4-(3-oxo-4-morpholinyl)phenyl]-amino}-2-hydroxypropyl)-2-thiophenecarboxamide (from Example 61), 197 mg (1.22 mmol) of carbonylimidazole and 7 mg of dimethylaminopyridine are boiled in 20 ml of dioxane under reflux for 5 hours. 20 ml of acetonitrile are then added, and the mixture is stirred in a closed container in a microwave oven at 180° C. for 30 minutes. The solution is concentrated in a rotary evaporator and chromatographed on an RP-HPLC column. 53 mg (19% of theory) of the target compound are obtained.

NMR (300 MHz, d$_6$-DMSO): δ=3.6-3.7 (m, 4H), 3.85 (dd, 1H), 3.95 (m, 2H), 4.2 (m, 1H), 4.21 (s, 2H), 4.85 (m, 1H), 4.18 (s, 2H), 7.19 (d, 1H, thiophene), 7.35 (dd, 1H), 7.45 (t, 1H), 7.55 (dd, 1H), 7.67 (d, 1H, thiophene), 8.95 (t, 1H, CONH).

Example 96

5-Chloro-N-[(2-oxo-3-phenyl-1,3-oxazolidin-5-yl)methyl]-2-thiophenecarboxamide starting from Example 62:
MS (ESI): m/z (%)=359 ([M+Na]$^+$, 71), 337 ([M+H]$^+$, 100), Cl pattern; HPLC (method 3): rt (%)=4.39 (100). IC$_{50}$: 2 μM.

Example 97

5-Chloro-N-({2-oxo-3-[4-(3-oxo-4-morpholinyl)phenyl]-1,3-oxazolidin-5-yl}-methyl)-2-thiophenecarboxamide starting from Example 63:
MS (ESI): m/z (%)=458 ([M+Na]$^+$, 66), 436 ([M+H]$^+$, 100), Cl pattern; HPLC (method 3): rt (%)=3.89 (100). IC$_{50}$: 1.4 nM.

Example 98

N-[(3-{4-[Acetyl(cyclopropyl)amino]phenyl}-2-oxo-1,3-oxazolidin-5-yl)methyl]-5-chloro-2-thiophenecarboxanmide starting from Example 64:
MS (ESI): m/z (%)=456 ([M+Na]$^+$, 55), 434 ([M+H]$^+$, 100), Cl pattern; HPLC (method 3): rt (%)=4.05 (100). IC$_{50}$: 50 nM.

Example 99

N-[(3-{4-[Acetyl(methyl)amino]phenyl}-2-oxo-1,3-oxazolidin-5-yl)methyl]-5-chloro-2-thiophenecarboxamide MS (ESI): m/z (%)=408 (M+H, 30), 449 (M+H+MeCN, 100); HPLC (method 4): rt=3.66 min.

Example 100

5-Chloro-N-({2-oxo-3-[4-(1H-1,2,3-triazol-1-yl)phenyl]-1,3-oxazolidin-5-yl}-methyl)-2-thiophenecarboxamide MS (ESI): m/z (%)=404 (M+H, 45), 445 (M+H+MeCN, 100); HPLC (method 4): rt=3.77 min.

Example 101

Tert-butyl 1-{4-[5-({[(5-chloro-2-thienyl)carbonyl]amino}methyl)-2-oxo-1,3-oxazolidin-3-yl]phenyl}-L-prolinate MS (ESI): m/z (%)=450 (M+H−56, 25), 506 (M+H, 100); HPLC (method 4): rt=5.13 min.

Example 102

1-{4-[5-({[(5-Chloro-2-thienyl)carbonyl]amino}methyl)-2-oxo-1,3-oxazolidin-3-yl]phenyl}-4-piperidinecarboxamide MS (ESI): m/z (%)=463 (M+H, 100); HPLC (method 4): rt=2.51 min.

Example 103

1-{4-[5-({[(5-Chloro-2-thienyl)carbonyl]amino}methyl)-2-oxo-1,3-oxazolidin-3-yl]phenyl}-3-piperidinecarboxamide MS (ESI,: m/z (%)=463 (M+H, 100); HPLC (method 4): rt=2.67 min.

Example 104

5-Chloro-N-({2-oxo-3-[4-(4-oxo-1-piperidinyl)phenyl]-1,3-oxazolidin-5-yl}methyl)-2-thiophenecarboxamide MS (ESI): m/z (%)=434 (M+H, 40), 452 (M+H+H$_2$O, 100), 475 (M+H+MeCN, 60); HPLC (method 4): rt=3.44 min.

Example 105

1-{4-[5-({[(5-Chloro-2-thienyl)carbonyl]amino}methyl)-2-oxo-1,3-oxazolidin-3-yl]phenyl}-L-prolinamide MS (ESI): m/z (%)=449 (M+H, 100); HPLC (method 4): rt=3.54 min.

Example 106

5-Chloro-N-[(3-{4-[3-(hydroxymethyl)-1-piperidinyl]phenyl}-2-oxo-1,3-oxazolidin-5-yl)methyl]-2-thiophenecarboxamide MS (ESI): m/z (%)=450 (M+H, 100); HPLC (method 5): rt=2.53 min.

Example 107

5-Chloro-N-[(3-{4-[2-(hydroxymethyl)-1-piperidinyl]phenyl}-2-oxo-1,3-oxazolidin-5-yl)methyl]-2-thiophenecarboxamide MS (ESI): m/z (%)=450 (M+H, 100); HPLC (method 5): rt=2.32 min.

Example 108

Ethyl 1-{4-[5-({[(5-chloro-2-thienyl)carbonyl]amino}methyl)-2-oxo-1,3-oxazolidin-3-yl]phenyl}-2-piperidinecarboxylate MS (ESI): m/z (%)=492 (M+H, 100); HPLC (method 5): rt=4.35 min.

Example 109

5-Chloro-N-[(3-{4-[2-(hydroxymethyl)-1-pyrrolidinyl]phenyl}-2-oxo-1,3-oxazolidin-5-yl)methyl]-2-thiophenecarboxamide MS (ESI): m/z (%)=436 (M+H, 100); HPLC (method 4): rt=2.98 min.

Example 110

5-Chloro-N-({2-oxo-3-[4-(1-pyrrolidinyl)-3-(trifluoromethyl)phenyl]-1,3-oxazolidin-5-yl}methyl)-2-thiophenecarboxamide MS (ESI): m/z (%)=474 (M+H, 100); HPLC (method 4): rt=4.63 min.

Example 111

5-Chloro-N-({3-[4-(2-methylhexahydro-5H-pyrrolo[3,4-d]isoxazol-5-yl)phenyl]-2-oxo-1,3-oxazolidin-5-yl}methyl)-2-thiophenecarboxamide MS (ESI): m/z (%)=463 (M+H, 100), HPLC (method 4): rt=2.56 min.

Example 112

5-Chloro-N-({2-oxo-3-[4-(2-oxo-1-pyrrolidinyl)-3-(trifluoromethyl)phenyl]-1,3-oxazolidin-5-yl}methyl)-2-thiophenecarboxamide MS (ESI): m/z (%)=488 (M+H, 100); HPLC (method 4): rt=3.64 min.

Example 113

5-Chloro-N-({3-[3-chloro-4-(3-oxo-4-morpholinyl)phenyl]-2-oxo-1,3-oxazolidin-5-yl}methyl)-2-thiophenecarboxamide MS (ESI): m/z (%)=470 (M+H, 100); HPLC (method 4): rt=3.41 min.

Example 114

5-Chloro-N-({2-oxo-3-[4-(3-oxo-4-morpholinyl)-3-(trifluoromethyl)phenyl]-1,3-oxazolidin-5-yl}methyl)-2-thiophenecarboxamide MS (ESI): m/z (%)=504 (M+H, 100); HPLC (method 4): rt=3.55 min.

Example 115

5-Chloro-N-({3-[3-methyl-4-(3-oxo-4-morpholinyl)phenyl]-2-oxo-1,3-oxazolidin-5-yl}methyl)-2-thiophenecarboxamide MS (ESI): m/z (%)=450 (M+H, 100); HPLC (method 4): rt=3.23 min.

Example 116

5-Chloro-N-({3-[3-cyano-4-(3-oxo-4-morpholinyl)phenyl]-2-oxo-1,3-oxazolidin-5-yl}methyl)-2-thiophenecarboxamide MS (ESI): m/z (%)=461 (M+H, 100); HPLC (method 4): rt=3.27 min.

Example 117

5-Chloro-N-({3-[3-chloro-4-(1-pyrrolidinyl)phenyl]-2-oxo-1,3-oxazolidin-5-yl}methyl)-2-thiophenecarboxamide MS (ESI): m/z (%)=440 (M+H, 100); HPLC (method 4): rt=3.72 min.

Example 118

5-Chloro-N-({3-[3-chloro-4-(2-oxo-1-pyrrolidinyl)phenyl]-2-oxo-1,3-oxazolidin-5-yl}methyl)-2-thiophenecarboxamide MS (ESI): m/z (%)=454 (M+H, 100); HPLC (method 4): rt=3.49 min.

Example 119

5-Chloro-N-({3-[3,5-dimethyl-4-(3-oxo-4-morpholinyl)phenyl]-2-oxo-1,3-oxazolidin-5-yl}methyl)-2-thiophenecarboxamide MS (ESI): m/z (%)=464 (M+H, 100); HPLC (method 4): rt=3.39 min.

Example 120

N-({3-[3-(Aminocarbonyl)-4-(4-morpholinyl)phenyl]-2-oxo-1,3-oxazolidin-5-yl}methyl)-5-chloro-2-thiophenecarboxamide MS (ESI): m/z (%)=465 (M+H, 100); HPLC (method 4): rt=3.07 min.

Example 121

5-Chloro-N-({3-[3-methoxy-4-(4-morpholinyl)phenyl]-2-oxo-1,3-oxazolidin-5-yl}methyl)-2-thiophenecarboxamide MS (ESI): m/z (%)=452 (M+H, 100); HPLC (method 4): rt=2.86 min.

Example 122

N-({3-[3-Acetyl-4-(4-morpholinyl)phenyl]-2-oxo-1,3-oxazolidin-5-yl}methyl)-5-chloro-2-thiophenecarboxamide MS (ESI): m/z (%)=464 (M+H, 100); HPLC (method 4): rt=3.52 min.

Example 123

N-({3-[3-Amino-4-(3-oxo-4-morpholinyl)phenyl]-2-oxo-1,3-oxazolidin-5-yl}-methyl)-5-chloro-2-thiophenecarboxamide MS (ESI): m/z (%)=451 (M+H, 100); HPLC (method 6): rt=3.16 min.

Example 124

5-Chloro-N-({3-[3-chloro-4-(2-methyl-3-oxo-4-morpholinyl)phenyl]-2-oxo-1,3-oxazolidin-5-yl}methyl)-2-thiophenecarboxamide MS (ESI): m/z (%)=484 (M+H, 100); HPLC (method 4): rt=3.59 min.

Example 125

5-Chloro-N-({3-[3-chloro-4-(2-methyl-5-oxo-4-morpholinyl)phenyl]-2-oxo-1,3-oxazolidin-5-yl}methyl)-2-thiophenecarboxamide MS (ESI): m/z (%)=484 (M+H, 100); HPLC (method 4): rt=3.63 min.

Example 125a

5-Chloro-N-[(2-oxo-3-{4-[(3-oxo-4-morpholinyl)methyl]phenyl}-1,3-oxazolidin-5-yl)methyl]-2-thiophenecarboxamide MS (ESI): m/z (%)=450 (M+H, 100); HPLC (method 4): rt=3.25 min.

In addition, the following compounds were prepared by the route of epoxide opening with an amine and subsequent cyclization to give the corresponding oxazolidinone:

| Example No. | Structure | M.p. [° C.] | IC$_{50}$ [μM] |
|---|---|---|---|
| 126 | 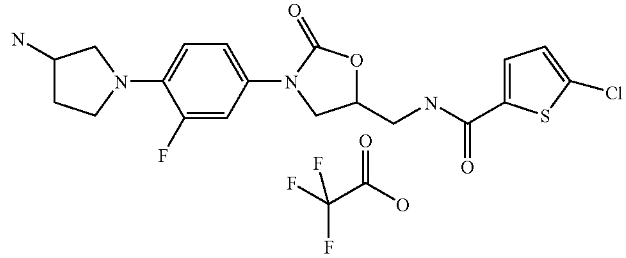 | 229 decomp. | 0.013 |

-continued

| Example No. | Structure | M.p. [° C.] | IC$_{50}$ [µM] |
|---|---|---|---|
| 127 | 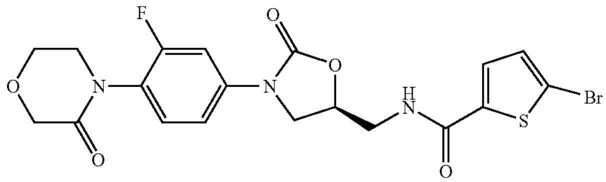 | 159 | 0.0007 |
| 128 | 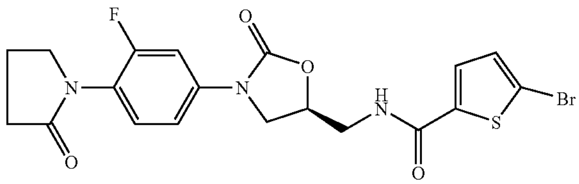 | 198 | 0.002 |
| 129 | 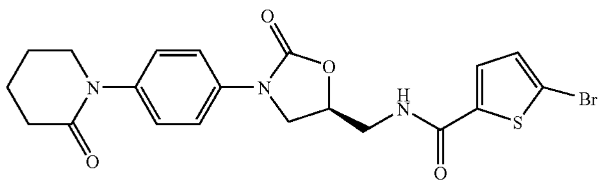 | 196 | 0.001 |
| 130 | 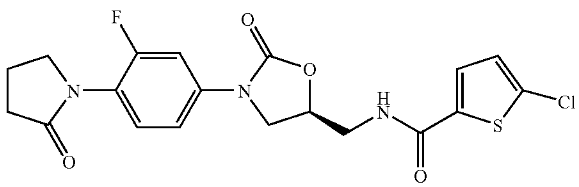 | 206 | 0.0033 |
| 130a | 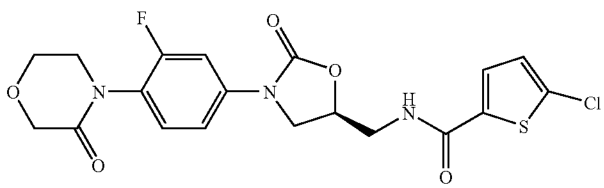 | 194 | |
| 131 | 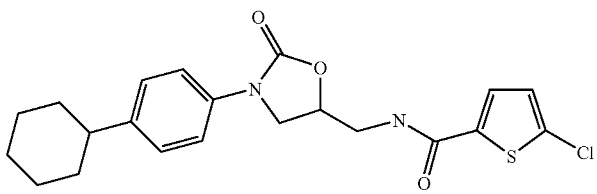 | 195 | 0.85 |
| 132 | 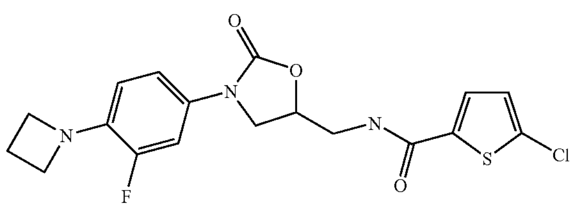 | 206 | 0.12 |
| 133 | 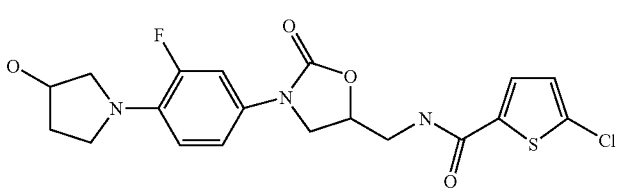 | 217 | 0.062 |

-continued

| Example No. | Structure | M.p. [° C.] | IC$_{50}$ [μM] |
|---|---|---|---|
| 134 | from 1-(4-Amino-phenyl)-piperidin-3-ol (Tong, L. K. J. et al; J. Amer. Chem. Soc 1960; 82, 1988). | 207 | 0.48 |
| 135 | 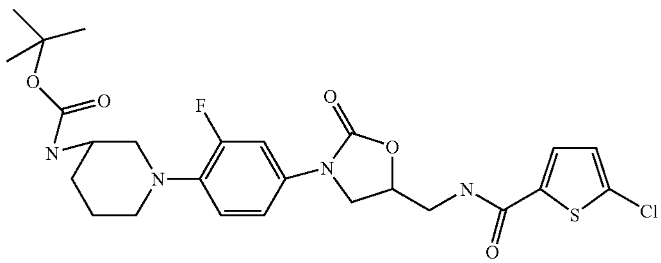 | 202 | 1.1 |
| 136 | 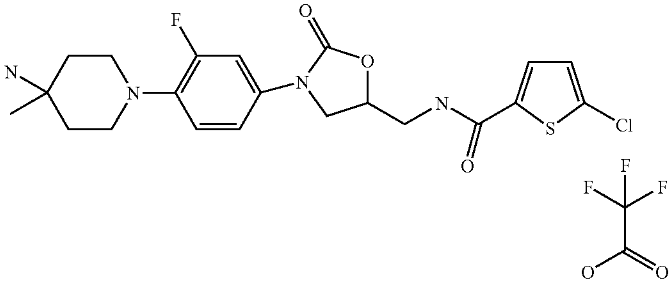 | 239 | 1.2 |
| 137 | 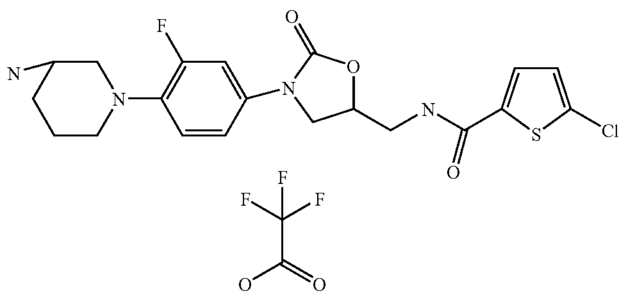 | 219 | 0.044 |
| 138 | 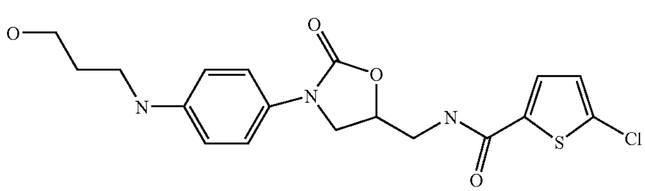 | 95 | 0.42 |
| 139 | 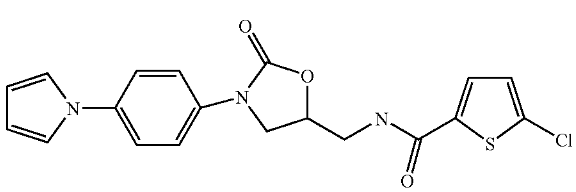 | 217 | 1.7 |

Example 14

5-Chloro-N-({(5S)-3-[3-fluoro-4-(1-oxo-1[lambda]$^4$,4-thiazinan-4-yl)phenyl]-2-oxo-1,3-oxazolidin-5-yl}methyl)-2-thiophenecarboxamide

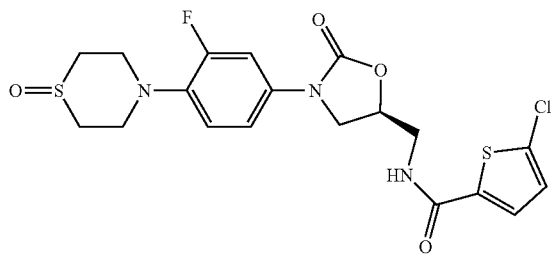

5-Chloro-N-({(5S)-3-[3-fluoro-4-(1,4-thiazinan-4-yl)phenyl]-2-oxo-1,3-oxazolidin-5-yl}methyl)-2-thiophenecarboxamide (0.1 g, 0.22 mmol) from Example 3 in methanol (0.77 ml) is added at 0° C. to a solution of sodium periodate (0.05 g, 0.23 mmol) in water (0.54 ml) and stirred at 0° C. for 3 h. Then 1 ml of DMF is added, and the mixture is stirred at RT for 8 h. Addition of a further 50 mg of sodium periodate is followed by stirring at RT once again overnight. 50 ml of water are then added to the mixture, and the insoluble product is filtered off with suction. Washing with water and drying result in 60 mg (58% of theory) of crystals.

M.p.: 257° C.; R$_f$(silica gel, toluene/ethyl acetate 1:1)=0.54 (precursor=0.46); IC$_{50}$=1.1 μM; MS (DCI) 489 (M+NH$_4$), Cl pattern.

Example 15

Preparation of 5-chloro-N-({(5S)-3-[4-(1,1-dioxo-1[lambda]$^6$,4-thiazinan-4-yl)-3-fluorophenyl]-2-oxo-1,3-oxazolidin-5-yl}methyl)-2-thiophenecarboxamide

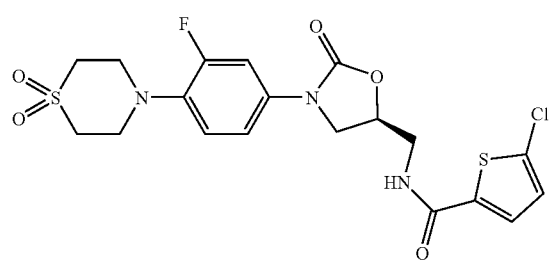

80 mg (0.66 mmol) of N-methylmorpholine N-oxide (NMO) and 0.1 ml of a 2.5% strength solution of osmium tetroxide in 2-methyl-2-propanol are added to 5-chloro-N-({(5S)-3-[3-fluoro-4-(1,4-thiazinan-4-yl)phenyl]-2-oxo-1,3-oxazolidin-5-yl}methyl)-2-thiophenecarboxamide from Example 3 (0.1 g, 0.22 mmol) in 3.32 ml of a mixture of 1 part of water and 3 parts of acetone. The mixture is stirred at room temperature overnight and a further 40 mg of NMO are added. After being stirred for a further night, the mixture is added to 50 ml of water and extracted three times with ethyl acetate. Drying and evaporation of the organic phase result in 23 mg, and filtration with suction of the insoluble solid from the aqueous phase results in 19 mg of the target compound (total 39% of theory).

M.p.: 238° C.; R$_f$(toluene/ethyl acetate 1:1)=0.14 (precursor=0.46); IC$_{50}$=210 nM; MS (DCI): 505 (M+NH$_4$), Cl pattern.

Example 16

5-Chloro-N-{[(5S)-3-(3-fluoro-4-morpholinophenyl)-2-oxo-1,3-oxazolidin-5-yl]methyl}-2-thiophenecarboxamide N-oxide is obtained by treating 5-chloro-N-{[(5S)-3-(3-fluoro-4-morpholinophenyl)-2-oxo-1,3-oxazolidin-5-yl]methyl}-2-thiophenecarboxamide from Example 1 with monoperoxyphthalic acid magnesium salt.

MS (ESI): 456 (M+H, 21%, Cl pattern), 439 (100%).

Examples 31 to 35 and 140 to 147 which follow relate to the optional amidination process step, i.e. one which takes place where appropriate.

General method for preparing amidines and amidine derivatives starting from cyanomethylphenyl-substituted 5-chloro-N-[(2-oxo-1,3-oxazolidin-5-yl)methyl]-2-thiophenecarboxamide derivatives The particular cyanomethylphenyl-substituted 5-chloro-N-[(2-oxo-1,3-oxazolidin-5-yl)methyl]-2-thiophenecarboxamide derivate (1.0 eq.) is stirred together with triethylamine (8.0 eq.) in a saturated solution of hydrogen sulfide in pyridine (approx. 0.05-0.1 mol/l) at RT for one to two days. The reaction mixture is diluted with ethyl acetate (EtOAc) and washed with 2 N hydrochloric acid. The organic phase is dried with MgSO$_4$, filtered and evaporated in vacuo.

The crude product is dissolved in acetone (0.01-0.1 mol/l), and methyl iodide (40 eq.) is added. The reaction mixture is stirred at room temperature (RT) for 2 to 5 h and then concentrated in vacuo.

The residue is dissolved in methanol (0.01-0.1 mol/l) and, to prepare the unsubstituted amidines, ammonium acetate (3 eq.) and ammonium chloride (2 eq.) are added. The substituted amidine derivatives are prepared by adding primary or secondary amines (1.5 eq.) and acetic acid (2 eq.) to the methanolic solution. After 5-30 h, the solvent is removed in vacuo and the residue is purified by chromatography on an RP8 silica gel column (water/acetonitrile 9/1-1/1+0.1% trifluoroacetic acid).

The following were prepared in an analogous manner:

Example 31

N-({3-[4-(2-Amino-2-iminoethyl)phenyl]-2-oxo-1,3-oxazolidin-5-yl}methyl)-5-chloro-2-thiophenecarboxamide MS (ESI): m/z (%)=393 (M+H, 100); HPLC (method 4): rt=2.63 min.

Example 32

5-Chloro-N-({3-[3-(4,5-dihydro-1H-imidazol-2-ylmethyl)phenyl]-2-oxo-1,3-oxazolidin-5-yl}methyl)-2-thiophenecarboxamide MS (ESI): m/z (%)=419 (M+H, 100); HPLC (method 4): rt=2.61 min.

Example 33

5-Chloro-N-[(3-{3-[2-imino-2-(4-morpholinyl)ethyl]phenyl}-2-oxo-1,3-oxazolidin-5-yl)methyl]-2-thiophenecarboxamide MS (ESI): m/z (%)=463 (M+H, 100); HPLC (method 4): rt=2.70 min.

Example 34

5-Chloro-N-[(3-{3-[2-imino-2-(1-pyrrolidinyl)ethyl]phenyl}-2-oxo-1,3-oxazolidin-5-yl)methyl]-2-thiophenecarboxamide MS (ESI): m/z (%)=447 (M+H, 100); HPLC (method 4): rt=2.82 min.

Example 35

N-({3-[3-(2-Amino-2-iminoethyl)phenyl]-2-oxo-1,3-oxazolidin-5-yl}methyl)-5-chloro-2-thiophenecarboxamide MS (ESI): m/z (%)=393 (M+H, 100); HPLC (method 4): rt=2.60 min.

Example 140

5-Chloro-N-({3-[4-(4,5-dihydro-1H-imidazol-2-ylmethyl)phenyl]-2-oxo-1,3-oxazolidin-5-yl}methyl)-2-thiophenecarboxamide MS (ESI): m/z (%)=419 (M+H, 100); HPLC (method 4): rt=2.65 min.

Example 141

5-Chloro-N-[(3-{4-[2-imino-2-(4-morpholinyl)ethyl]phenyl}-2-oxo-1,3-oxazolidin-5-yl)methyl]-2-thiophenecarboxamide MS (ESI): m/z (%)=463 (M+H, 100); HPLC (method 4): rt=2.65 min.

Example 142

5-Chloro-N-[(3-{4-[2-imino-2-(1-piperidinyl)ethyl]phenyl}-2-oxo-1,3-oxazolidin-5-yl)methyl]-2-thiophenecarboxamide MS (ESI): m/z (%)=461 (M+H, 100); HPLC (method 4): rt=2.83 min.

Example 143

5-Chloro-N-[(3-{4-[2-imino-2-(1-pyrrolidinyl)ethyl]phenyl}-2-oxo-1,3-oxazolidin-5-yl)methyl]-2-thiophenecarboxamide MS (ESI): m/z (%)=447 (M+H, 100); HPLC (method 4): rt=2.76 min.

Example 144

5-Chloro-N-[(3-{4-[2-(cyclopentylamino)-2-iminoethyl]phenyl}-2-oxo-1,3-oxazolidin-5-yl)methyl]-2-thiophenecarboxamide MS (ESI): m/z (%)=461 (M+H, 100); HPLC (method 4): rt=2.89 min.

Example 145

5-Chloro-N-{[3-(4-{2-imino-2-[(2,2,2-trifluoroethyl)amino]ethyl}phenyl)-2-oxo-1,3-oxazolidin-5-yl]methyl}-2-thiophenecarboxamide MS (ESI): m/z (%)=475 (M+H, 100); HPLC (method 4): rt=2.79 min.

Example 146

N-({3-[4-(2-Anilino-2-iminoethyl)phenyl]-2-oxo-1,3-oxazolidin-5-yl}methyl)-5-chloro-2-thiophenecarboxamide MS (ESI): m/z (%)=469 (M+H, 100); HPLC (method 4): rt=2.83 min.

Example 147

5-Chloro-N-[(3-{4-[2-imino-2-(2-pyridinylamino)ethyl]phenyl}-2-oxo-1,3-oxazolidin-5-yl)methyl]-2-thiophenecarboxamide MS (ESI): m/z (%)=470 (M+H, 100); HPLC (method 4): rt=2.84 min.

Examples 148 to 151 which follow relate to the elimination of BOC amino protective groups:

General method for eliminating Boc protective groups (tert-butyloxycarbonyl):

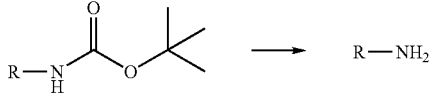

Aqueous trifluoroacetic acid (TFA, approx. 90%) is added dropwise to an ice-cooled solution of a tert-butyloxycarbonyl-(Boc)-protected compound in chloroform or dichloromethane (approx. 0.1 to 0.3 mol/l). After about 15 min, the ice cooling is removed and the mixture is stirred at room temperature for about 2-3 h before the solution is concentrated and dried under high vacuum. The residue is taken up in dichloromethane or dichloromethane/methanol and washed with saturated sodium bicarbonate or 1N sodium hydroxide solution. The organic phase is washed with saturated sodium chloride solution, dried over a little magnesium sulfate and concentrated. Purification takes place where appropriate by crystallization from ether or ether/dichloromethane mixtures.

The following were prepared in an analogous manner from the appropriate Boc-protected precursors:

Example 148

N-({3-[4-(Aminomethyl)phenyl]-2-oxo-1,3-oxazolidin-5-yl}methyl)-5-chloro-2-thiophenecarboxamide starting from Example 92:
MS (ESI): m/z (%)=349 (M–NH$_2$, 25), 305 (100); HPLC (method 1): rt (%)=3.68 (98). IC$_{50}$: 2.2 µM.

Example 149

N-{[3-(4-Aminophenyl)-2-oxo-1,3-oxazolidin-5-yl]methyl}-5-chloro-2-thiophenecarboxamide starting from Example 93:
MS (ESI): m/z (%)=352 (M+H, 25); HPLC (method 1): rt (%)=3.50 (100). IC$_{50}$: 2 µM.

An enantiopure alternative synthesis of this compound is depicted in the following scheme (cf. also Delalande S. A., DE 2836305, 1979; Chem. Abstr. 90, 186926):

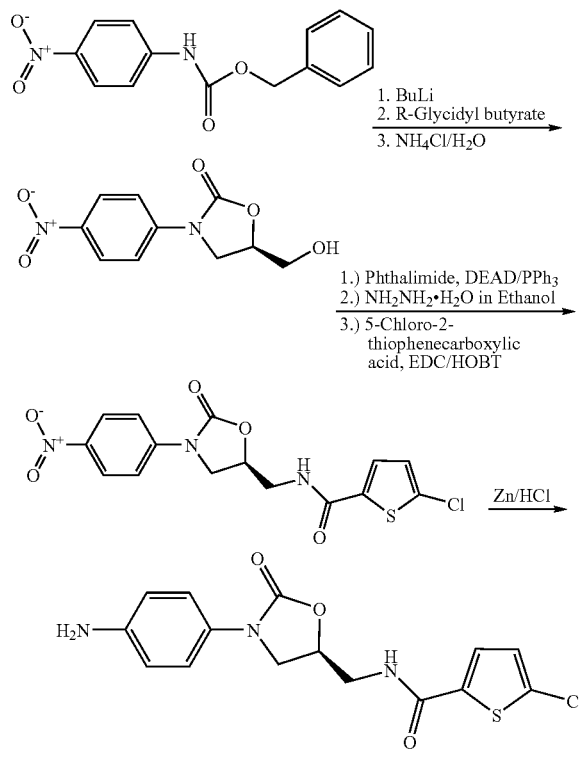

Example 150

5-Chloro-N-({3-[4-(glycylamino)phenyl]-2-oxo-1,3-oxazolidin-5-yl}methyl)-2-thiophenecarboxamide starting from Example 152:
MS (ES-pos): m/z (%)=408 (100); HPLC (method 3): rt (%)=3.56 (97). IC$_{50}$: 2 µM.

Example 151

5-(Aminomethyl)-3-[4-(2-oxo-1-pyrrolidinyl)phenyl]-1,3-oxazolidin-2-one starting from Example 60:
MS (ESI): m/z (%)=276 (M+H, 100); HPLC (method 3): rt (%)=2.99 (100). IC$_{50}$: 2 µM.

Examples 152 to 166 which follow relate to the amino group-derivatization of aniline- or benzylamine-substituted oxazolidinones with various reagents:

Example 152

5-Chloro-N-({3-[4-(N-tert-butyloxycarbonyl-glycylamino)phenyl]-2-oxo-1,3-oxazolidin-5-yl}methyl)-2-thiophenecarboxamide

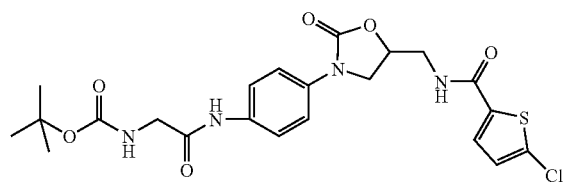

754 mg (2.1 mmol) of N-{[3-(4-aminophenyl)-2-oxo-1,3-oxazolidin-5-yl]methyl}-5-chloro-2-thiophenecarboxamide (from Example 149) are added to a solution of 751 mg (4.3 mmol) of Boc-glycine, 870 mg (6.4 mmol) of HOBT (1-hydroxy-1H-benzotriazole×H$_2$O), 1790 mg (4.7 mmol) of HBTU [O-(benzotriazol-1-yl)-N,N,N',N'-tetramethyluronium hexafluorophosphate] and 1.41 ml (12.9 mmol) of N-methylmorpholine in 15 ml of DMF/CH$_2$Cl$_2$ (1:1) at 0° C. The mixture is stirred at room temperature overnight before being diluted with water. The precipitated solid is filtered off and dried. Yield: 894 mg (79.7% of theory);

MS (DCI, NH$_3$): m/z (%)=526 (M+NH$_4$, 100); HPLC (method 3): rt (%)=4.17 (97).

Example 153

N-[(3-{4-[(Acetylamino)methyl]phenyl}-2-oxo-1,3-oxazolidin-5-yl)methyl]-5-chloro-2-thiophenecarboxamide

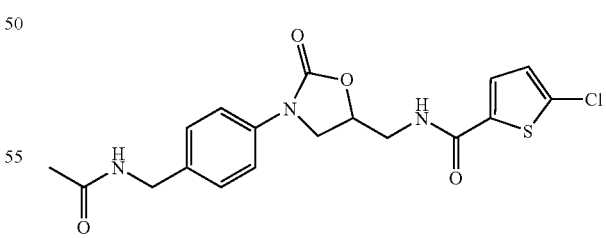

Acetic anhydride (0.015 ml, 0.164 mmol is added to a mixture of 30 mg (0.082 mmol) of N-({3-[4-(aminomethyl)phenyl]-2-oxo-1,3-oxazolidin-5-yl}methyl)-5-chloro-2-thiophenecarboxamide (from Example 148) in 1.5 ml of absolute THF and 1.0 ml of absolute dichloromethane, 0.02 ml of absolute pyridine at 0° C. The mixture is stirred at room temperature overnight. The product is obtained after addition of ether and crystallization. Yield: 30 mg (87% of theory), MS (ESI): m/z (%)=408 (M+H, 18), 305 (85); HPLC (method 1): rt (%)=3.78 (97). $IC_{50}$: 0.6 µM.

Example 154

N-{[3-(4-{[(Aminocarbonyl)amino]methyl}phenyl)-2-oxo-1,3-oxazolidin-5-yl]-methyl}-5-chloro-2-thiophenecarboxamide

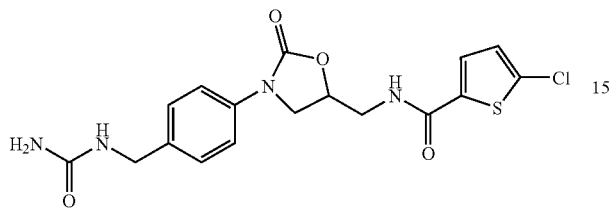

0.19 ml (0.82 mmol) of trimethylsilyl isocyanate is added dropwise to a mixture of 30 mg (0.082 mmol) of N-({3-[4-(aminomethyl)phenyl]-2-oxo-1,3-oxazolidin-5-yl}methyl)-5-chloro-2-thiophenecarboxamide (from Example 148) in 1.0 ml of dichloromethane at room temperature. The mixture is stirred overnight before, after addition of ether, the product is obtained by filtration. Yield: 21.1 mg (52% of theory), MS (ESI): m/z (%)=409 (M+H, 5), 305 (72); HPLC (method 1): rt (%)=3.67 (83). $IC_{50}$: 1.3 µM.

General method for acylating N-{[3-(4-aminophenyl)-2-oxo-1,3-oxazolidin-5-yl]methyl}-5-chloro-2-thiophenecarboxamide with carbonyl chlorides:

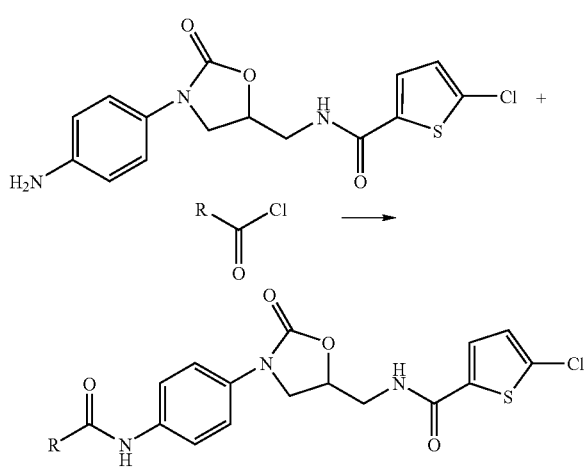

An approx. 0.1 molar solution of N-{[3-(4-aminophenyl)-2-oxo-1,3-oxazolidin-5-yl]methyl}-5-chloro-2-thiophenecarboxamide (from Example 149) (1.0 eq.) in absolute dichloromethane/pyridine (19:1) is added dropwise under argon to the appropriate acid chloride (2.5 eq.). The mixture is stirred overnight before addition of approx. 5 eq of PS-trisamine (Argonaut Technologies) and 2 ml of absolute dichloromethane. Gentle stirring for 1 h is followed by filtration and concentration of the filtrate. The products are purified where appropriate by preparative RP-HPLC.

The following were prepared in an analogous manner:

Example 155

N-({3-[4-(Acetylamino)phenyl]-2-oxo-1,3-oxazolidin-5-yl}methyl)-5-chloro-2-thiophenecarboxamide LC-MS: m/z (%)=394 (M+H, 100); LC-MS (method 6): rt (%)=3.25 (100). $IC_{50}$: 1.2 µM.

Example 156

5-Chloro-N-[(2-oxo-3-{4-[(2-thienylcarbonyl)amino]phenyl}-1,3-oxazolidin-5-yl)methyl]-2-thiophenecarboxamide LC-MS: m/z (%)=462 (M+H, 100); LC-MS (method 6): rt (%)=3.87 (100). $IC_{50}$: 1.3 µM.

Example 157

5-Chloro-N-[(3-{4-[(methoxyacetyl)amino]phenyl}-2-oxo-1,3-oxazolidin-5-yl)-methyl]-2-thiophenecarboxamide LC-MS: m/z (%)=424 (M+H, 100); LC-MS (method 6): rt (%)=3.39 (100). $IC_{50}$: 0.73 µM.

Example 158

N-{4-[5-({[(5-Chloro-2-thienyl)carbonyl]amino}methyl)-2-oxo-1,3-oxazolidin-3-yl]phenyl}-3,5-dimethyl-4-isoxazolecarboxamide LC-MS: m/z (%)=475 (M+H, 100). $IC_{50}$: 0.46 µM.

Example 159

5-Chloro-N-{[3-(4-{[(3-chloropropyl)sulfonyl]amino}phenyl)-2-oxo-1,3-oxazolidin-5-yl]methyl}-2-thiophenecarboxamide

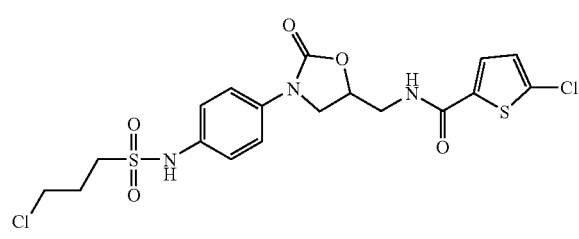

35 mg (0.1 mmol) of N-{[3-(4-aminophenyl)-2-oxo-1,3-oxazolidin-5-yl]-methyl}-5-chloro-2-thiophenecarboxamide (from Example 149) are added to an ice-cooled solution of 26.4 mg (0.15 mmol) of 3-chloro-1-propanesulfonyl chloride and 0.03 ml (0.2 mmol) of triethylamine in 3.5 ml of absolute dichloromethane. After 30 min, the ice cooling is removed and the mixture is stirred at room temperature overnight before adding 150 mg (approx. 5.5 eq) of PS-trisamine (Argonaut Technologies) and 0.5 ml of dichloromethane. The suspension is stirred gently for 2 h and filtered (the resin is washed with dichloromethane/methanol), and the filtrate is concentrated. The product is purified by preparative RP-HPLC. Yield: 19.6 mg (40% of theory), LC-MS: m/z (%)=492 (M+H, 100); LC-MS (method 5): rt (%)=3.82 (91). $IC_{50}$: 1.7 μM.

Example 160

5-Chloro-N-({3-[4-(1,1-dioxido-2-isothiazolidinyl) phenyl]-2-oxo1,3-oxazolidin-5-yl}methyl)-2-thiophenecarboxamide

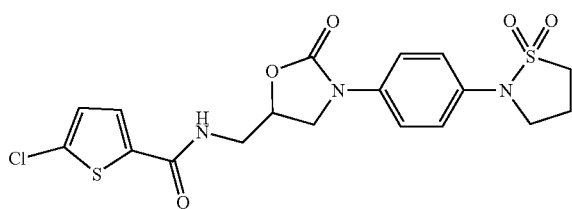

A mixture of 13.5 mg (0.027 mmol) of 5-chloro-N-{[3-(4-{[(3-chloropropyl)sulfonyl]amino}phenyl)-2-oxo-1,3-oxazolidin-5-yl]methyl}-2-thiophenecarboxamide (from Example 159) and 7.6 mg (0.055 mmol) of potassium carbonate in 0.2 ml of DMF is heated at 100° C. for 2 h. Cooling is followed by dilution with dichloromethane and washing with water. The organic phase is dried and concentrated. The residue is purified by preparative thin-layer chromatography (silica gel, dichloromethane/methanol, 95:5). Yield: 1.8 mg (14.4% of theory), MS (ESI): m/z (%)=456 (M+H, 15), 412 (100); LC-MS (method 4): rt (%)=3.81 (90). $IC_{50}$: 0.14 μM.

Example 161

5-Chloro-N-[((5S)-3-{4-[(5-chloropentanoyl)amino] phenyl}-2-oxo-1,3-oxazolidin-5-yl)methyl]-2-thiophenecarboxamide

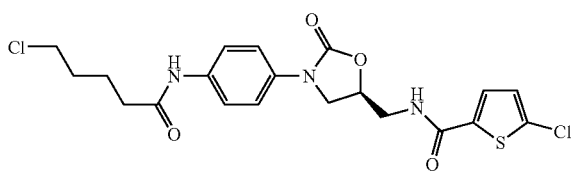

0.5 g (1.29 mmol) of N-{[(5S)-3-(4-aminophenyl)-2-oxo-1,3-oxazolidin-5-yl]methyl}-5-chloro-2-thiophenecarboxamide (from Example 149) is dissolved in 27 ml of tetrahydrofuran, and 0.2 g (1.29 mmol) of 5-chlorovaleryl chloride and 0.395 ml (2.83 mmol) of triethylamine are added. The mixture is evaporated in vacuo and chromatographed on silica gel with a toluene/ethyl acetate=1:1→ethyl acetate gradient. 315 mg (52% of theory) of a solid are obtained.

M.p.: 211° C.

Example 162

5-Chloro-N-({(5S)-2-oxo-3-[4-(2-oxo-1-piperidinyl) phenyl]-1,3-oxazolidin-5-yl}-methyl)-2-thiophenecarboxamide

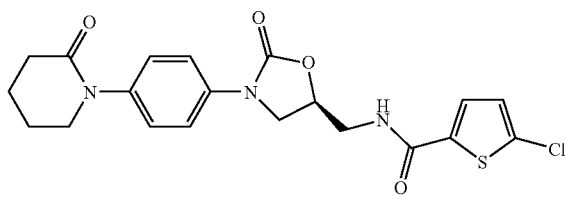

30 mg of 60 percent NaH in liquid paraffin are added under inert conditions to 5 ml of DMSO, and the mixture is heated at 75° C. for 30 min until gas evolution ceases. Then a solution of 290 mg (0.617 mmol) of 5-chloro-N-[((5S)-3-{4-[(5-chloropentanoyl)amino]phenyl}-2-oxo-1,3-oxazolidin-5-yl)methyl]-2-thiophenecarboxamide (from Example 161) in 5 ml of methylene chloride is added dropwise, and the mixture is stirred at room temperature overnight. The reaction is stopped and the mixture is added to 100 ml of water and extracted with ethyl acetate. The evaporated organic phase is chromatographed on an RP-8 column and eluted with acetonitrile/water. 20 mg (7.5% of theory) of the target compound are obtained.

M.p.: 205° C.; NMR (300 MHz, $d_6$-DMSO): δ=1.85 (m, 4H), 2.35 (m, 2H), 3.58 (m, 4H), 3.85 (m, 1H), 4.2 (t, 1H), 4.82 (m, 1H), 7.18 (d, 1H, thiophene), 7.26 (d, 2H), 7.5 (d, 2H), 2.68 (d, 1H, thiophene), 9.0 (t, 1H, CONH). $IC_{50}$: 2.8 nM.

Example 163

5-Chloro-N-[((5S)-3-{4-[(3-bromopropionyl)amino] phenyl}-2-oxo-1,3-oxazolidin-5-yl)methyl]-2-thiophenecarboxamide

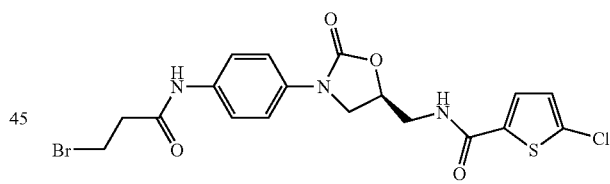

is obtained in an analogous manner from Example 149.

Example 164

5-Chloro-N-({(5S)-2-oxo-3-[4-(2-oxo-1-azetidinyl) phenyl]-1,3-oxazolidin-5-yl}-methyl)-2-thiophenecarboxamide

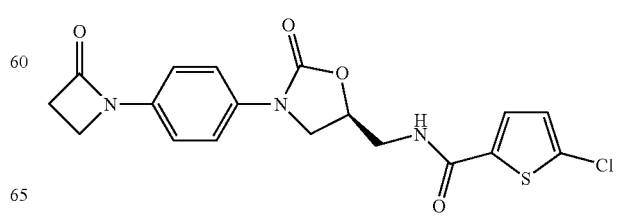

is obtained in an analogous manner by cyclization of the open-chain bromopropionyl compound from Example 163 using NaH/DMSO.

MS (ESI): m/z (%)=406 ([M+H]$^+$, 100), Cl pattern. IC$_{50}$: 380 nM.

Example 165 tert-Butyl 4-{4-[5-({[(5-chloro-2-thienyl)carbonyl]amino}methyl)-2-oxo-1,3-oxazolidin-3-yl]phenyl}-3,5-dioxo-1-piperazinecarboxylate 300 mg (0.85 mmol) of N-{[3-(4-aminophenyl)-2-oxo-1,3-oxazolidin-5-yl]-methyl}-5-chloro-2-thiophenecarboxamide in 6 ml of a mixture of DMF and dichloromethane (1:1) are added to a solution of 199 mg (0.85 mmol) of Boc-iminodiacetic acid, 300 mg (2.2 mmol) of HOBT, 0.66 ml (6 mmol) of N-methylmorpholine and 647 mg (1.7 mmol) of HBTU. The mixture is stirred overnight before, after dilution with dichloromethane, being washed with water, saturated ammonium chloride solution, saturated sodium bicarbonate solution, water and saturated sodium chloride solution. The organic phase is dried over magnesium sulfate and concentrated. The crude product is purified by chromatography on silica gel (dichloromethane/methanol 98:2). Yield: 134 mg (29% of theory);

MS (ESI): m/z (%)=571 (M+Na, 82), 493 (100); HPLC (method 3): rt (%)=4.39 (90). IC$_{50}$: 2 μM.

Example 166

N-[((5S)-3-{4-[(3R)-3-Amino-2-oxo-1-pyrrolidinyl]phenyl}-2-oxo-1,3-oxazolidin-5-yl)methyl]-5-chloro-2-thiophenecarboxamide trifluoroacetate

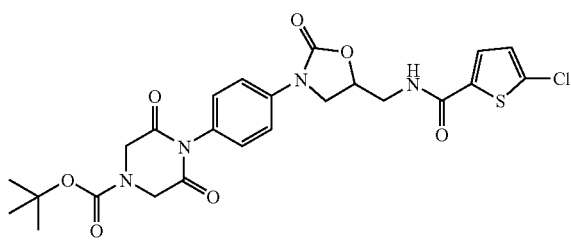

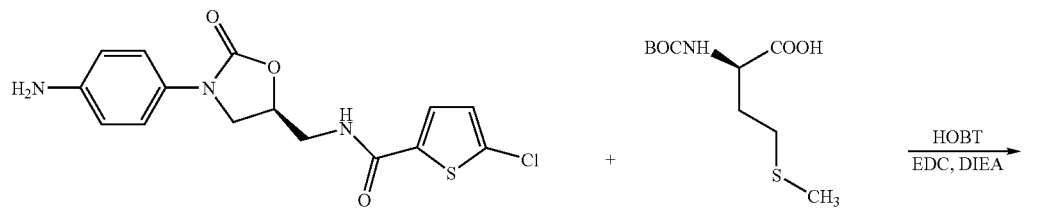

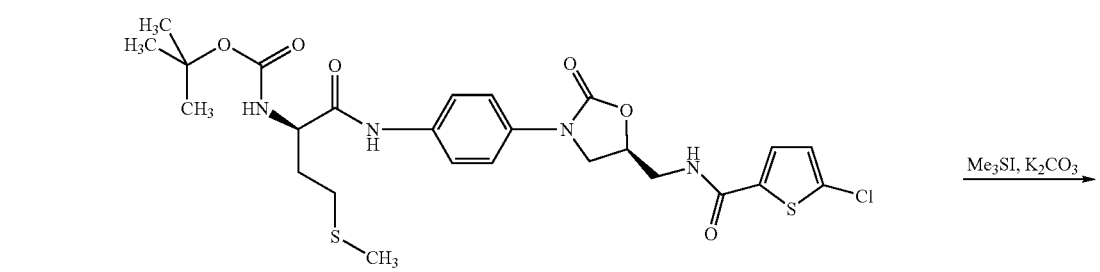

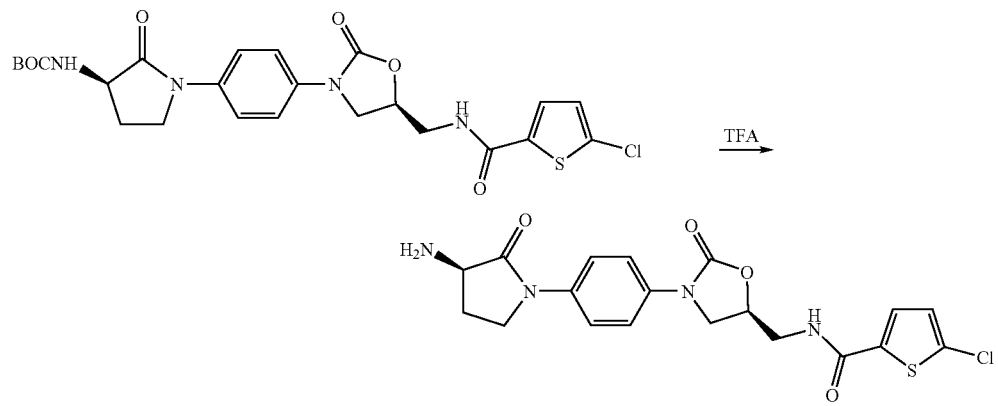

N2-(tert-Butoxycarbonyl)-N1-{4-[(5S)-5-({[(5-chloro-2-thienyl)carbonyl]amino}-methyl)-2-oxo-1,3-oxazolidin-3-yl]phenyl}-D-methioninamide 429 mg (1.72 mmol) of N-BOC-D-methionine, 605 mg (1.72 mmol) of N-{[(5S)-3-(4-aminophenyl)-2-oxo-1,3-oxazolidin-5-yl]methyl}-5-chloro-2-thiophenecarboxamide, and 527 mg (3.44 mmol) of HOBT hydrate are dissolved in 35 ml of DMF, and 660 mg (3.441 mmol) of EDCI hydrochloride and then, dropwise, 689 mg (5.334 mmol) of N-ethyldiisopropylamine are added. The mixture is stirred at room temperature for two days. The resulting suspension is filtered with suction and the residue is washed with DMF. The combined filtrates are mixed with a little silica gel, evaporated in vacuo and chromatographed on silica gel with a toluene->T10EA7 gradient; 170 mg (17% of theory) of the target compound are obtained with a melting point of 183° C.

$R_f$(SiO$_2$, toluene/ethyl acetate=1:1): 0.2. $^1$H-NMR (300 MHz, d$_6$-DMSO): δ=1.4 (s, 1H, BOC), 1.88-1.95 (m, 2H), 2.08 (s, 3H, SMe), 2.4-2.5 (m, 2H, partly covered by DMSO), 3.6 (m, 2H), 3.8 (m, 1H), 4.15 (m, 2H), 4.8 (m, 1H), 7.2 (1H, thiophene), 7.42 (d, part of an AB system, 2H), 7.6 (d, part of an AB system, 2H), 7.7 (d, 1H, thiophene), 8.95 (t, 1H, CH$_2$NHCO), 9.93 (bs, 1H, NH).

tert-Butyl (3R)-1-{4-[(5S)-5-({[(5-chloro-2-thienyl)carbonyl]amino}methyl)-2-oxo-1,3-oxazolidin-3-yl]phenyl}-2-oxo-3-pyrrolidinylcarbamate 170 mg (0.292 mmol) of N2-(tert-butoxycarbonyl)-N1-{4-[(5S)-5-({[(5-chloro-2-thienyl)carbonyl]amino}methyl)-2-oxo-1,3-oxazolidin-3-yl]phenyl}-D-methioninamide are dissolved in 2 ml of DMSO, and 178.5 mg (0.875 mmol) of trimethylsulfonium iodide and 60.4 mg (0.437 mmol) of potassium carbonate are added, and the mixture is stirred at 80° C. for 3.5 hours. It is then evaporated under high vacuum, and the residue is washed with ethanol. 99 mg of the target compound remain.

$^1$H-NMR (300 MHz, d$_6$-DMSO): δ=1.4 (s, 1H, BOC), 1.88-2.05 (m, 1H), 2.3-2.4 (m, 1H), 3.7-3.8 (m, 3H), 3.8-3.9 (m, 1H), 4.1-4.25 (m, 1H), 4.25-4.45 (m, 1H), 4.75-4.95 (m, 1H), 7.15 (1H, thiophene), 7.25 (d, 1H), 7.52 (d, part of an AB system, 2H), 7.65 (d, part of an AB system, 2H), 7.65 (d, 1H, thiophene), 9.0 (broad s, 1H).

N-[((5S)-3-{4-[(3R)-3-Amino-2-oxo-1-pyrrolidinyl]phenyl}-2-oxo-1,3-oxazolin-5-yl)methyl]-5-chloro-2-thiophenecarboxamide trifluoroacetate 97 mg (0.181 mmol) of tert-butyl (3R)-1-{4-[(5S)-5-({[(5-chloro-2-thienyl)carbonyl]amino}methyl)-2-oxo-1,3-oxazolidin-3-yl]phenyl}-2-oxo-3-pyrrolidinylcarbamate are suspended in 4 ml of methylene chloride and, after addition of 1.5 ml of trifluoroacetic acid, stirred at room temperature for 1 hour. The mixture is then evaporated in vacuo and purified on an RP-HPLC (acetonitrile/water/0.1% TFA gradient). Evaporation of the relevant fraction results in 29 mg (37% of theory) of the target compound with a melting point of 241° C. (decomposition).

$R_f$(SiO$_2$, EtOH/TEA=17:1) 0.19. $^1$H-NMR (300 MHz, d$_6$-DMSO): δ=1.92-2.2 (m, 1H), 2.4-2.55 (m, 1H, partially covered by DMSO peak), 3.55-3.65 (m, 2H), 3.75-3.95 (m, 3H), 4.1-4.3 (m, 2H), 4.75-4.9 (m, 1H), 7.2 (1H, thiophene), 7.58 (d, part of an AB system, 2H), 7.7 (d, part of an AB system, 2H), 7.68 (d, 1H, thiophene), 8.4 (broad s, 3H, NH$_3$), 8.9 (t, 1H, NHCO).

Examples 167 to 170 which follow relate to the introduction of sulfonamide groups into phenyl-substituted oxazolidinones:

General method for preparing substituted sulfonamides starting from 5-chloro-N-[(2-oxo-3-phenyl-1,3-oxazolidin-5-yl)methyl]-2-thiophenecarboxamide

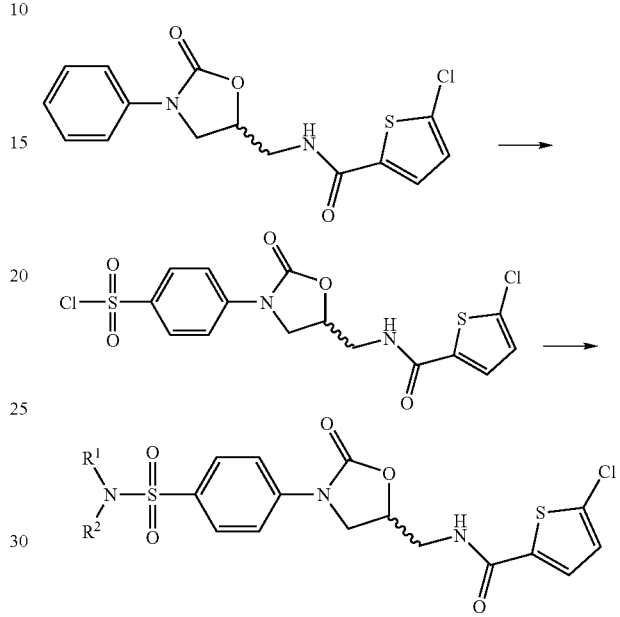

5-Chloro-N-[(2-oxo-3-phenyl-1,3-oxazolidin-5-yl)methyl]-2-thiophenecarboxamide (from Example 96) is added to chlorosulfonic acid (12 eq.) under argon at 5° C. The reaction mixture is stirred at room temperature for 2 h and then added to ice-water. The precipitate which separates out is filtered, washed with water and dried.

It is then dissolved in tetrahydrofuran (0.1 mol/l) under argon at room temperature, and the appropriate amine (3 eq.), triethylamine (1.1 eq.) and dimethylaminopyridine (0.1 eq.) are added. The reaction mixture is stirred for 1-2 h and then concentrated in vacuo. The desired product is purified by flash chromatography (dichloromethane/methanol mixtures).

The following were prepared in an analogous manner:

Example 167

5-Chloro-N-({2-oxo-3-[4-(1-pyrrolidinylsulfonyl)phenyl]-1,3-oxazolidin-5-yl}-methyl)-2-thiophenecarboxamide MS (ESI): m/z (%)=492 ([M+Na]$^+$, 100), 470 ([M+H]$^+$, 68), Cl pattern; HPLC (method 3): rt (%)=4.34 (100). IC$_{50}$: 0.5 µM.

Example 168

5-Chloro-N-[(3-{4-[(4-methyl-1-piperazinyl)sulfonyl]phenyl}-2-oxo-1,3-oxazolidin-5-yl)methyl]-2-thiophenecarboxamide MS (ESI): m/z (%)=499 ([M+H]$^+$, 100), Cl pattern; HPLC (method 2): rt (%)=3.3 (100).

Example 169

5-Chloro-N-({2-oxo-3-[4-(1-piperidinylsulfonyl)phenyl]-1,3-oxazolidin-5-yl}-methyl)-2-thiophenecarboxamide MS (ESI): m/z (%)=484 ([M+H]$^+$, 100), Cl pattern; HPLC (method 2): rt (%)=4.4 (100).

Example 170

5-Chloro-N-[(3-{4-[(4-hydroxy-1-piperidinyl)sulfonyl]phenyl}-2-oxo-1,3-oxazolidin-5-yl)methyl]-2-thiophenecarboxamide MS (ESI): m/z (%)=500 ([M+H]$^+$, 100), Cl pattern; HPLC (method 3): rt (%)=3.9 (100).

Example 171

5-Chloro-N-({2-oxo-3-[4-(1-pyrrolidinyl)phenyl]-1,3-oxazolidin-5-yl}methyl)-2-thiophenecarboxamide

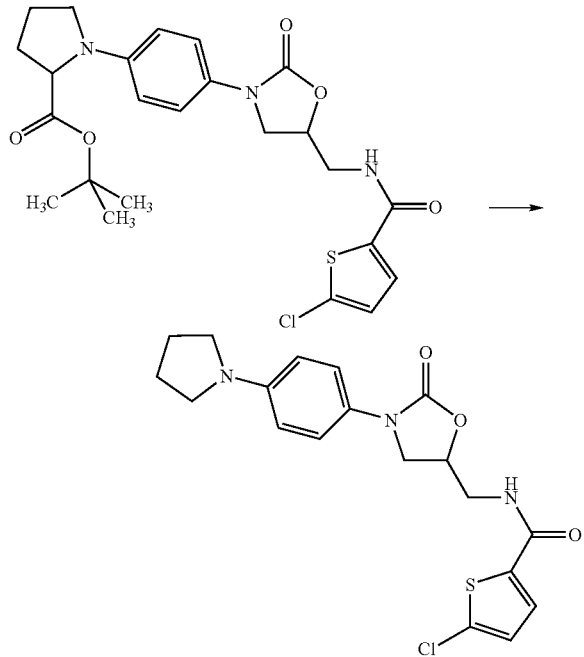

780 mg (1.54 mmol) of tert-butyl 1-{4-[5-({[(5-chloro-2-thienyl)carbonyl]amino}-methyl)-2-oxo-1,3-oxazolidin-3-yl]phenyl}prolinate are dissolved in 6 ml of dichloromethane and 9 ml of trifluoroacetic acid, and the mixture is stirred at 40° C. for two days. The reaction mixture is then concentrated and stirred with ether and 2 N sodium hydroxide solution. The aqueous phase is concentrated and stirred with ether and 2 N hydrochloric acid. The organic phase from this extraction is dried over MgSO$_4$, filtered and concentrated. The crude product is chromatographed on silica gel (CH$_2$Cl$_2$/EtOH/conc. aq. NH$_3$ solution=100/1/0.1 to 20/1/0.1).

280 mg (40% of theory) of the product are obtained.

MS (ESI): m/z (%)=406 (M+H, 100); HPLC (method 4): rt=3.81 min.

HPLC Parameters and LC-MS Parameters for the HPLC and LC-MS Data Stated in the Preceding Examples (the Unit of Retention Time (rt) is Minutes):

[1] Column: Kromasil C18, L-R temperature: 30° C., flow rate=0.75 mlmin$^{-1}$, eluent: A=0.01 M HClO$_4$, B=CH$_3$CN, gradient: ->0.5 min 98% A ->4.5 min 10% A ->6.5 min 10% A

[2] Column: Kromasil C18 60*2, L-R temperature: 30° C., flow rate=0.75 mlmin$^{-1}$, eluent: A=0.01 M H$_3$PO$_4$, B=CH$_3$CN, gradient: ->0.5 min 90% A ->4.5 min 10% A ->6.5 min 10% A

[3] Column: Kromasil C18 60*2, L-R temperature: 30° C., flow rate=0.75 mlmin$^{-1}$, eluent: A=0.005 M HClO$_4$, B=CH$_3$CN, gradient: ->0.5 min 98% A ->4.5 min 10% A ->6.5 min 10% A

[4] Column: Symmetry C18 2.1×150 mm, column oven: 50° C., flow rate=0.6 mlmin$^{-1}$, eluent: A=0.6 g of 30% HCl/l of water, B=CH$_3$CN, gradient: 0.0 min 90% A ->4.0 min 10% A ->9 min 10% A

[5] MHZ-2Q, Instrument Micromass Quattro LCZ Column Symmetry C18, 50 mm×2.1 mm, 3.5 µm, temperature: 40° C., flow rate=0.5 ml min$^{-1}$, eluent A=CH$_3$CN+0.1% formic acid, eluent B=water+0.1% formic acid, gradient: 0.0 min 10% A ->4 min 90% A ->6 min 90% A

[6] MHZ-2P, Instrument Micromass Platform LCZ Column Symmetry C18, 50 mm×2.1 mm, 3.5 µm, temperature: 40° C., flow rate=0.5 mlmin$^{-1}$, eluent A=CH$_3$CN+0.1% formic acid, eluent B=water+0.1% formic acid, gradient: 0.0 min 10% A ->4 min 90% A ->6 min 90% A

[7] MHZ-7Q, Instrument Micromass Quattro LCZ Column Symmetry C18, 50 mm×2.1 mm, 3.5 µm, temperature: 40° C., flow rate=0.5 mlmin$^{-1}$, eluent A=CH$_3$CN+0.1% formic acid, eluent B=water+0.1% formic acid, gradient: 0.0 min 5% A ->1 min 5% A ->5 min 90% A ->6 min 90% A General Method for Preparing Oxazolidinones of the General Formula B by Solid Phase-Assisted Synthesis Reactions with various resin-bound products took place in a set of separate reaction vessels.

5-(Bromomethyl)-3-(4-fluoro-3-nitrophenyl)-1,3-oxazolidin-2-one A (prepared from epibromohydrin and 4-fluoro-3-nitrophenyl isocyanate with LiBr/Bu$_3$PO in xylene in analogy to U.S. Pat. No. 4,128,654, Ex. 2) (1.20 g, 3.75 mmol) and ethyldiisoproylamine (DIEA, 1.91 ml, 4.13 mmol) were dissolved in DMSO (70 ml), mixed with a secondary amine (1.1 eq, amine component 1) and reacted at 55° C. for 5 h. Tenta-Gel SAM resin (5.00 g, 0.25 mmol/g) was added to this solution and reacted at 75° C. for 48 h. The resin was filtered and repeatedly washed with methanol (MeOH), dimethylformamide (DMF), MeOH, dichloromethane (DCM) and diethyl ether and dried. The resin (5.00 g) was suspended in dichloromethane (80 ml), mixed with DIEA (10 eq) and 5-chlorothiophene-2-carbonyl chloride [prepared by reacting 5-chlorothiophene-2-carboxylic acid (5 eq) and 1-chloro-1-dimethylamino-2-methylpropene (5 eq) in DCM (20 ml) at room temperature for 15 minutes] and reacted at room temperature for 5 h. The resulting resin was filtered and washed repeatedly with MeOH, DCM and diethyl ether and dried. The resin was then suspended in DMF/water (v/v 9:2, 80 ml), mixed with SnCl$_2$*2H$_2$O (5 eq) and reacted at room temperature for 18 h. The resin was again washed repeatedly with MeOH, DMF, water, MeOH, DCM and diethyl ether and dried. This resin was suspended in DCM, mixed with DEA (10 eq) and, at 0° C., with an acid chloride (5 eq of acid derivative 1) and reacted at room temperature overnight. Before the reaction, carboxylic acids were converted into the corresponding acid chlorides by reacting with 1-dimethylamino-1-chloro-2-methylpropene (1 eq, based on the carboxylic acid) in DCM at room temperature for 15 min. The resin was washed repeatedly with DMF, water, DMF, MeOH, DCM and diethyl ether and dried. Where Fmoc-protected amino acids were used as acid derivative 1, the Fmoc-protective group was eliminated in the last reaction step by reacting with piperidine/DMF (v/v, 1/4) at room temperature for 15 minutes, and the resin was washed with DMF, MeOH, DCM and diethyl ether and dried. The products were then cleaved off the solid phase with trifluoroacetic acid (TFA)/DCM (v/v, 1/1), the resin was filtered off, and the reaction solutions were evaporated. The crude products were filtered through silica gel (DCM/MeOH, 9:1) and evaporated in order to obtain a set of products B.

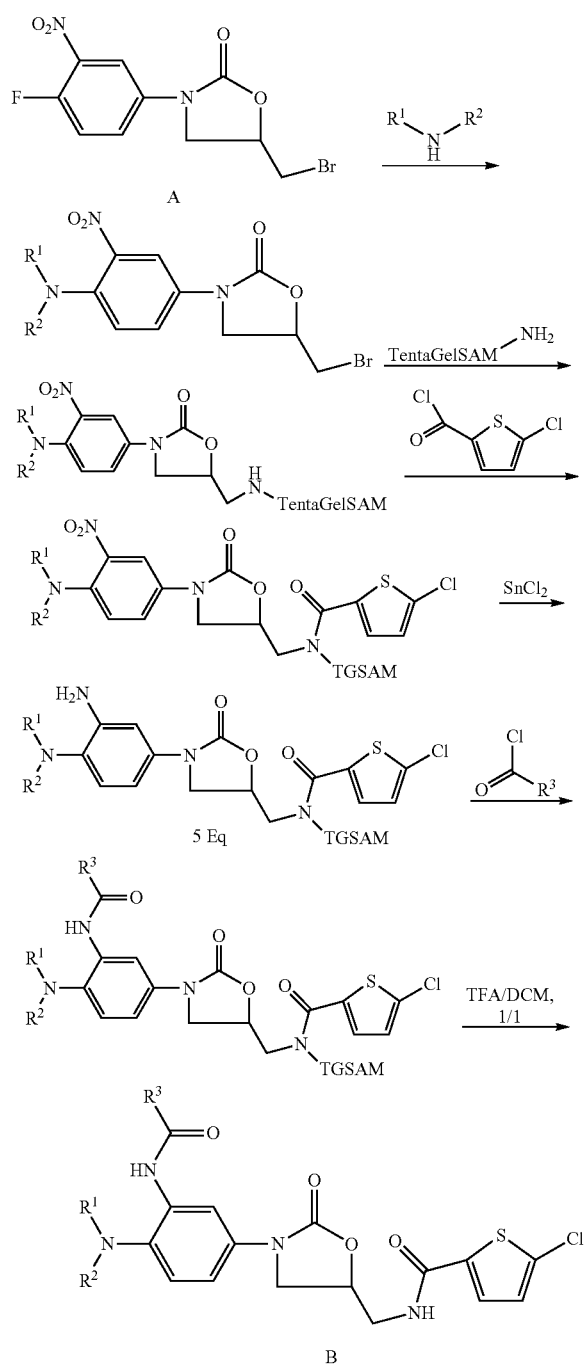

Compounds prepared by solid phase-assisted synthesis:

Example 172

N-({3-[3-Amino-4-(1-pyrrolidinyl)phenyl]-2-oxo-1,3-oxazolidin-5-yl}methyl)-5-chloro-2-thiophenecarboxamide

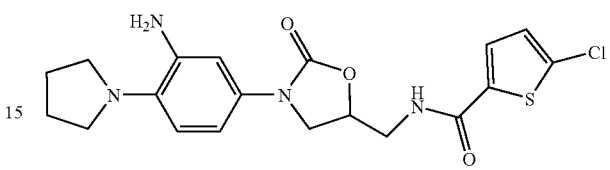

5 g (1.25 mmol) of TentaGel SAM resin were reacted with pyrrolidine as amine derivative 1 in analogy to the general procedure for preparing the derivatives B. The aniline obtained after reduction with $SnCl_2 \cdot 2H_2O$ was eliminated from the solid phase, without a further acylation step, and evaporated. The crude product was partitioned between ethyl acetate and $NaHCO_3$ solution, and the organic phase was salted out with NaCl, decanted and evaporated to dryness. This crude product was purified by vacuum flash chromatography on silica gel (dichloromethane/ethyl acetate, 3:1-1:2).

$^1$H-NMR (300 MHz, $CDCl_3$): 1.95-2.08, br, 4H; 3.15-3.30, br, 4H; 3.65-3.81, m, 2H; 3.89, ddd, 1H; 4.05, dd, 1H; 4.81, dddd, 1H; 6.46, dd, 1H; 6.72, dd, 1H; 6.90, dd, 1H; 6.99, dd, 1H; 7.03, dd, 1H; 7.29, d, 1H.

Example 173

N-[(3-{3-(β-Alanylamino)-4-[(3-hydroxypropyl)amino]phenyl}-2-oxo-1,3-oxazolidin-5-yl)methyl]-5-chloro-2-thiophenecarboxamide

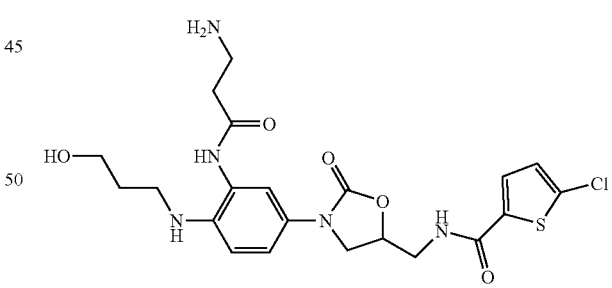

5 g (1.25 mmol) of TentaGel SAM resin were reacted with azetidine as amine derivative 1 and Fmoc-β-alanine as acid derivative 1 in analogy to the general procedure for preparing the derivates B. The crude product obtained after elimination was stirred in methanol at room temperature for 48 h and evaporated to dryness. This crude product was purified by reversed phase HPLC with a water/TFA/acetonitrile gradient.

$^1$H-NMR (400 MHz, $CD_3OD$): 2.31, tt, 2H; 3.36, t, 2H; 3.54, t, 2H; 3.62, t, 2H; 3.72, dd, 1H; 3.79, dd, 1H; 4.01, dd, 1H; 4.29, dd, 2H; 4.43, t, 2H; 4.85-4.95, m, 1H; 7.01, d, 1H; 4.48-7.55, m, 2H; 7.61, d, 1H; 7.84, d, 1H.

Example 174

N-({3-[4-(3-Amino-1-pyrrolidinyl)-3-nitrophenyl]-2-oxo-1,3-oxazolidin-5-yl}-methyl)-5-chloro-2-thiophenecarboxamide

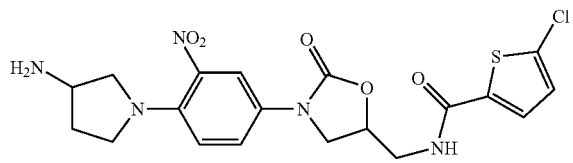

130 mg (32.5 μmol) of TentaGel SAM resin were reacted with tert-butyl 3-pyrrolidinylcarbamate as amine derivative 1 in analogy to the general procedure for preparing the derivates B. The nitrobenzene derivative obtained after acylation with 5-chlorothiophenecarboxylic acid was eliminated from the solid phase and evaporated. This crude product was purified by reversed phase HPLC with a water/TFA/acetonitrile gradient.

$^1$H-NMR (400 MHz, CD$_3$OH): 2.07-2.17, m, 1H; 2.39-2.49, m, 1H; 3.21-3.40, m, 2H; 3.45, dd, 1H; 3.50-3.60, m, 1H; 3.67, dd, 1H; 3.76, dd, 1H; 3.88-4.00, m, 2H; 4.14-4.21, t, 1H; 4.85-4.95, m, 1H; 7.01, d, 1H; 7.11, d, 1H; 7.52, d, 1H; 7.66, dd, 1H; 7.93, d, 1H.

Example 175

N-({3-[3-amino-4-(1-piperidinyl)phenyl]-2-oxo-1,3-oxazolidin-5-yl}methyl)-5-chloro-2-thiophenecarboxamide

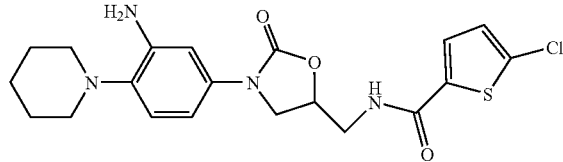

130 mg (32.5 μmol) of TentaGel SAM resin were reacted with piperidine as amine derivative 1 in analogy to the general procedure for preparing the derivatives B. The aniline obtained after reduction was eliminated, without a further acylation step, from the solid phase and evaporated. This crude product was purified by reversed phase HPLC with a water/TFA/acetonitrile gradient.

$^1$H-NMR (400 MHz, CD$_3$OH): 1.65-1.75, m, 2H; 1.84-1.95, m, 4H; 3.20-3.28, m, 4H; 3.68, dd, 1H; 3.73, dd, 1H; 3.90, dd, 1H; 4.17, dd, 1H; 4.80-4.90, m, 1H; 7.00, d, 1H; 7.05, dd, 1H; 7.30-7.38, m, 2H; 7.50, d, 1H.

Example 176

N-({3-[3-(Acetylamino)-4-(1-pyrrolidinyl)phenyl]-2-oxo-1,3-oxazolidin-5-yl}-methyl)-5-chloro-2-thiophenecarboxamide

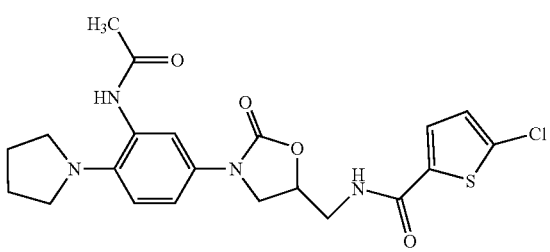

130 mg (32.5 μmol) of TentaGel SAM resin were reacted with pyrrolidine as amine derivative 1 and acetyl chloride as acid derivative 1 in analogy to the general procedure for preparing the derivatives B. The crude product was partitioned between ethyl acetate and NaHCO$_3$ solution, and the organic phase was salted out with NaCl, decanted and evaporated to dryness. This crude product was purified by vacuum flash chromatography on silica gel (dichloromethane/ethyl acetate, 1:1-0:1).

$^1$H-NMR (400 MHz, CD$_3$OH): 1.93-2.03, br, 4H; 2.16, s, 3H; 3.20-3.30, br, 4H; 3.70, d, 2H; 3.86, dd, 1H; 4.10, dd, 1H; 4.14, dd, 1H; 4.80-4.90, m, 1H; 7.00, d, 1H; 7.07, d, 1H; 7.31, dd, 1H; 7.51, d, 1H; 7.60, d, 1H.

The following compounds were prepared in analogy to the general procedure.

| Example | Structure | Ret. time | HPLC [%] |
|---|---|---|---|
| 177 | 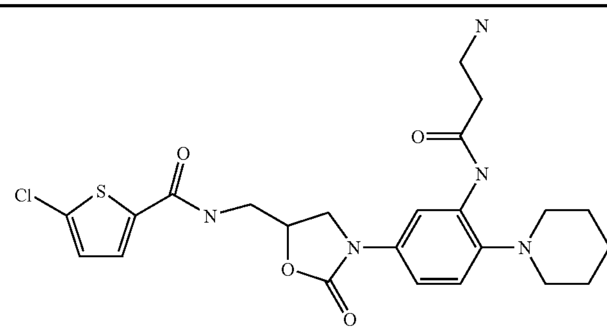 | 2.62 | 79.7 |
| 178 | 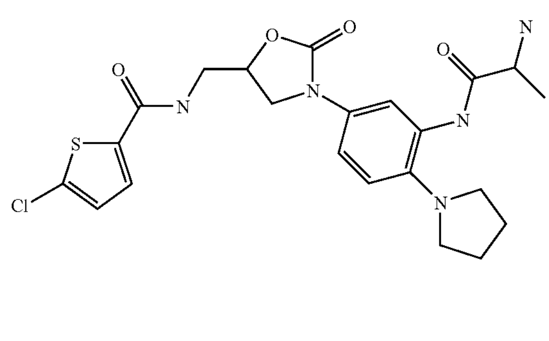 | 2.49 | 33.7 |

| Example | Structure | Ret. time | HPLC [%] |
|---|---|---|---|
| 179 | 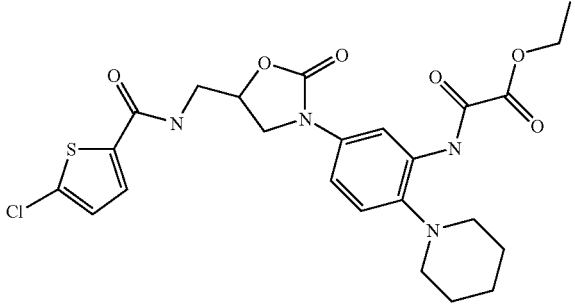 | 4.63 | 46.7 |
| 180 | 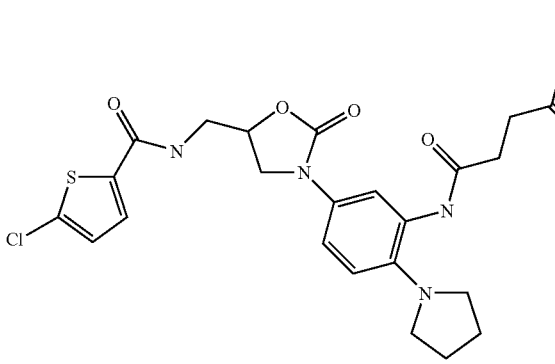 | 3.37 | 44.8 |
| 181 | 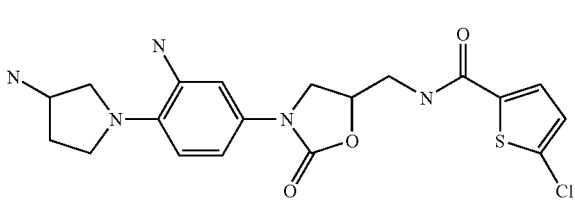 | 2.16 | 83 |
| 182 | 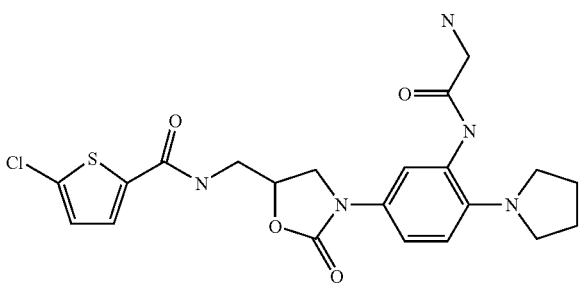 | 2.31 | 93.3 |

| Example | Structure | Ret. time | HPLC [%] |
|---|---|---|---|
| 183 | 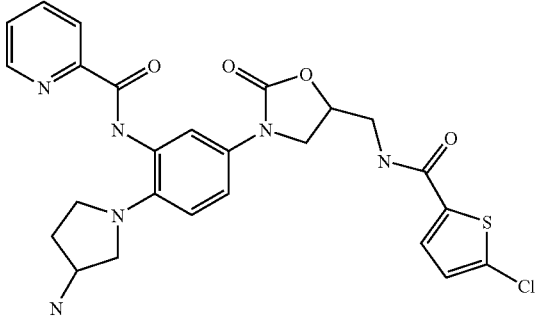 | 2.7 | 100 |
| 184 | 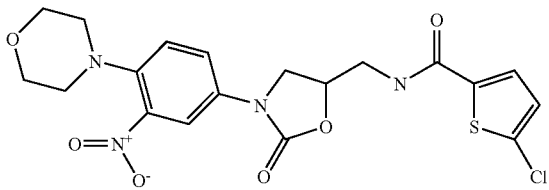 | 3.91 | 51 |
| 185 | 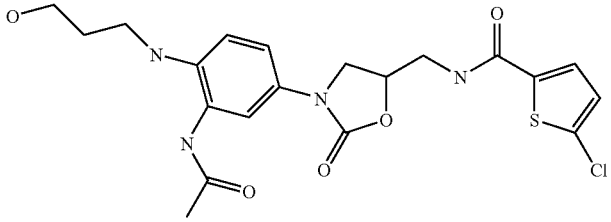 | 2.72 | 75.2 |
| 186 | 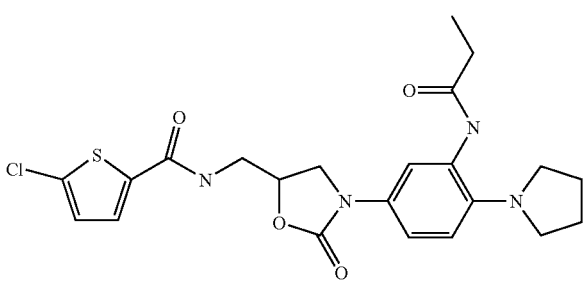 | 3.17 | 46 |
| 187 | 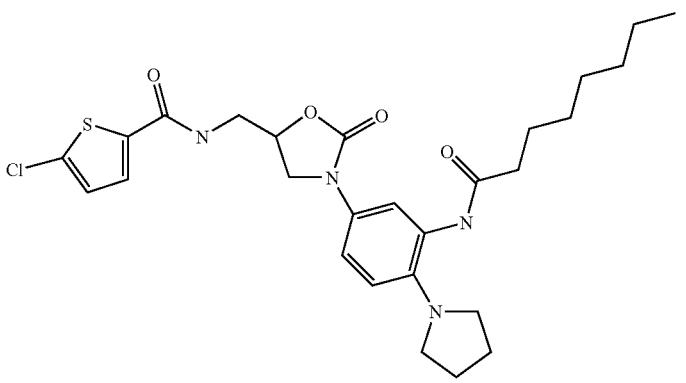 | 4.61 | 50.2 |

-continued
| Example | Structure | Ret. time | HPLC [%] |
|---|---|---|---|
| 188 | 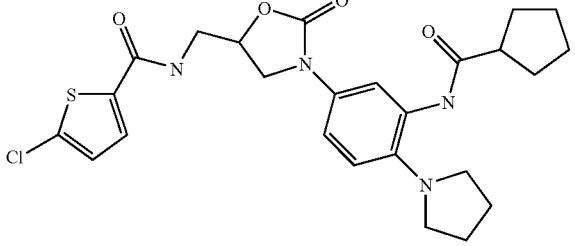 | 3.89 | 56.6 |
| 189 | 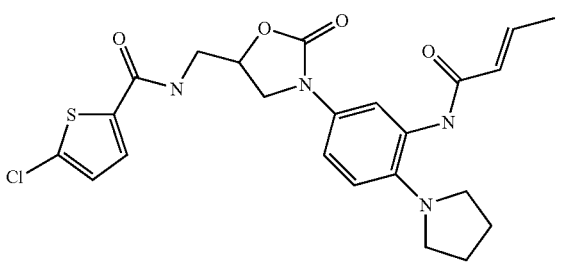 | 3.37 | 52.9 |
| 190 | 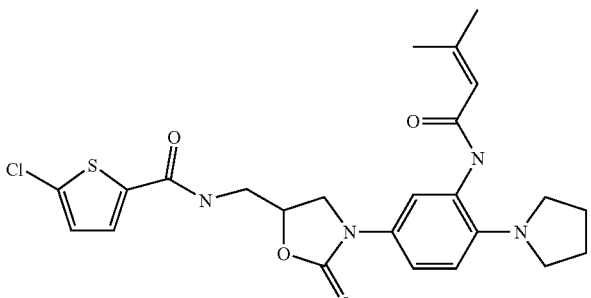 | 3.6 | 63.9 |
| 191 | 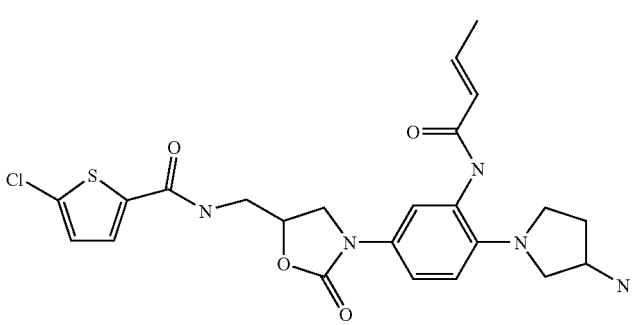 | 2.52 | 70.1 |
| 192 | 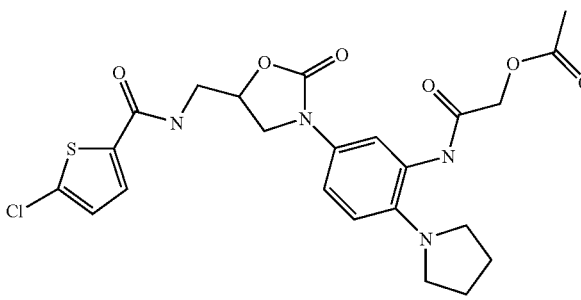 | 3.52 | 46.6 |

| Example | Structure | Ret. time | HPLC [%] |
|---|---|---|---|
| 193 | 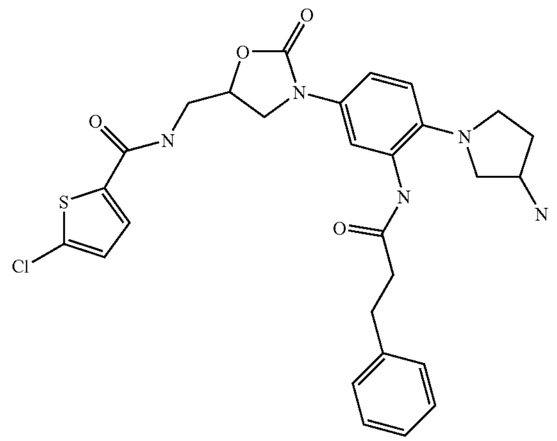 | 2.87 | 50.1 |
| 194 | 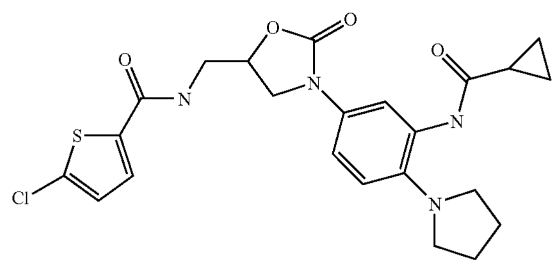 | 3.25 | 71.1 |
| 195 | 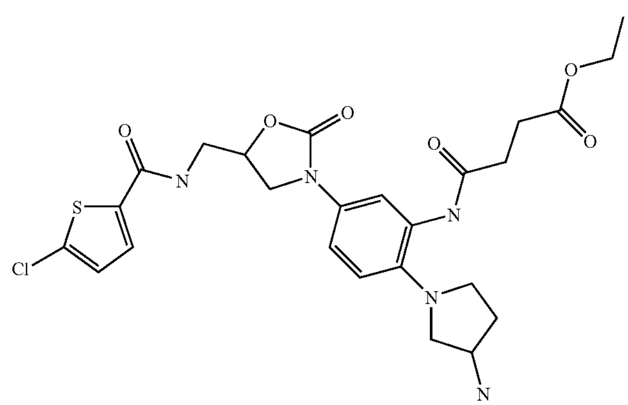 | 2.66 | 67 |
| 196 | 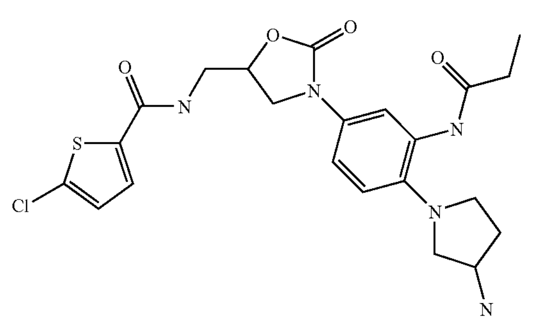 | 2.4 | 52.1 |

-continued
| Example | Structure | Ret. time | HPLC [%] |
|---|---|---|---|
| 197 | 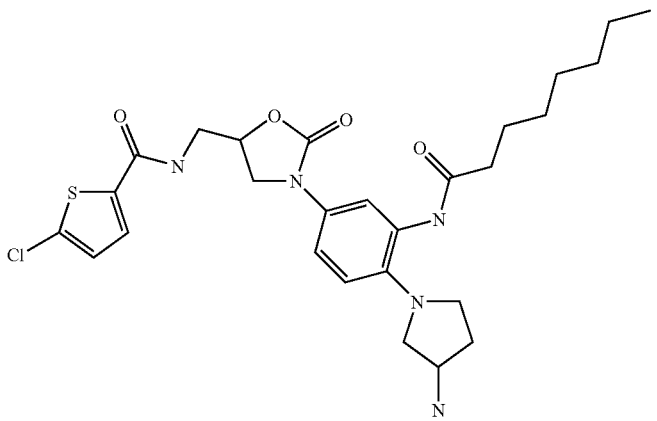 | 3.13 | 48.9 |
| 198 | 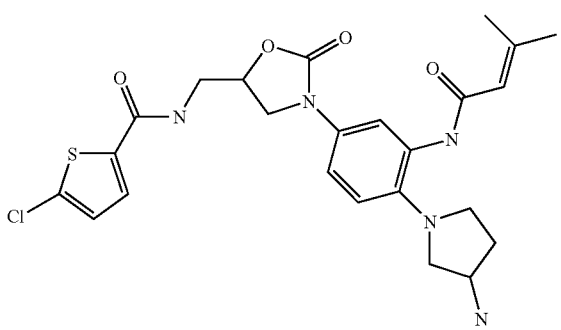 | 2.67 | 75.5 |
| 199 | 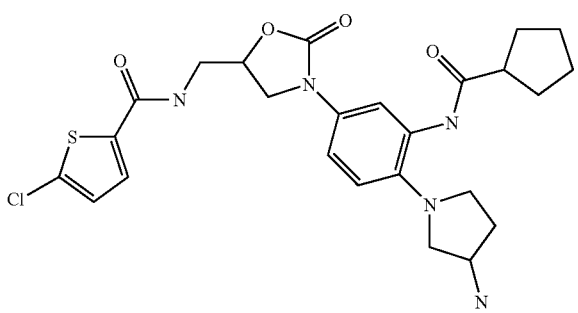 | 2.72 | 65.7 |
| 200 | 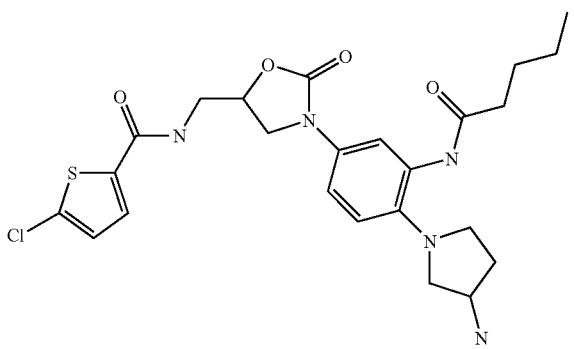 | 2.71 | 57.3 |

-continued
| Example | Structure | Ret. time | HPLC [%] |
|---|---|---|---|
| 201 | 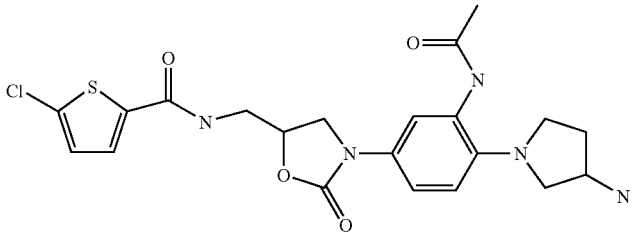 | 2.22 | 100 |
| 202 | 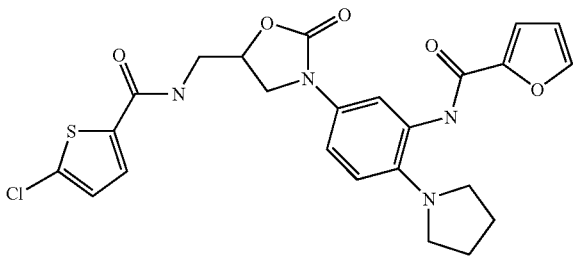 | 3.89 | 75.7 |
| 203 | 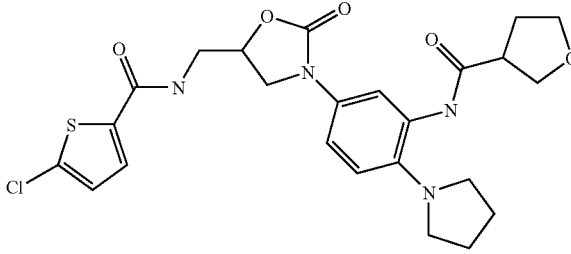 | 3.19 | 49.6 |
| 204 | 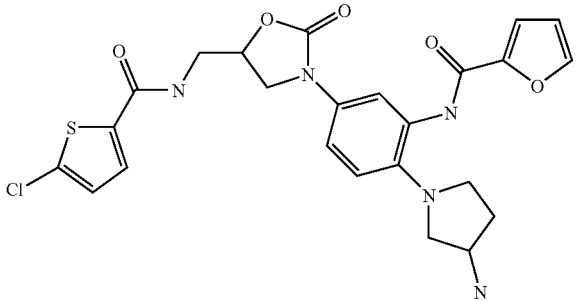 | 2.55 | 88.2 |
| 205 | 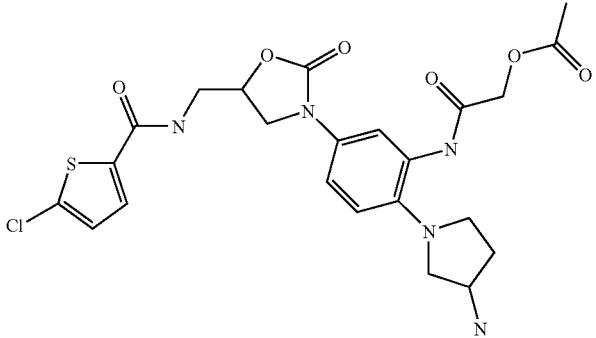 | 2.44 | 68.6 |

-continued
| Example | Structure | Ret. time | HPLC [%] |
|---|---|---|---|
| 206 | 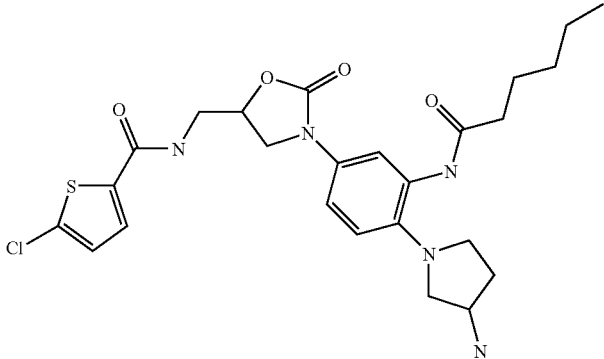 | 2.86 | 71.8 |
| 207 | 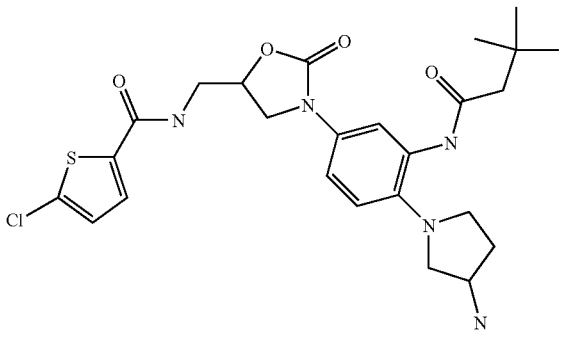 | 2.8 | 63.6 |
| 208 | 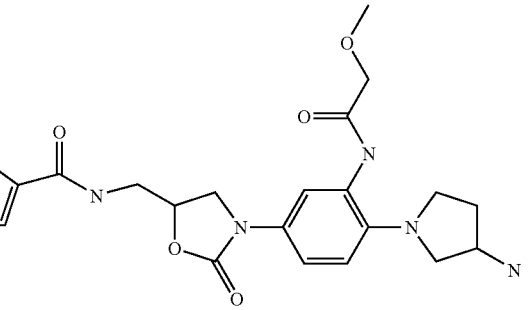 | 2.41 | 77 |
| 209 | 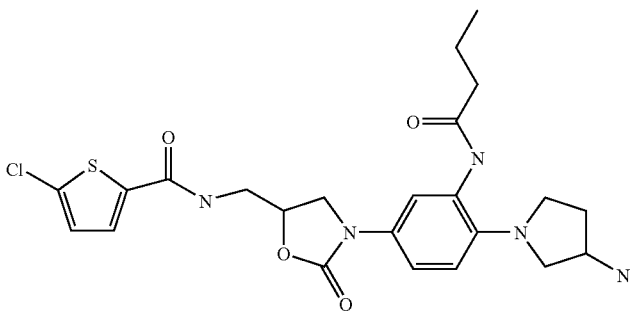 | 2.56 | 67.9 |

-continued
| Example | Structure | Ret. time | HPLC [%] |
|---|---|---|---|
| 210 | 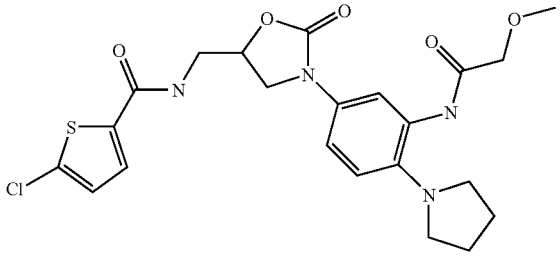 | 3.67 | 78.4 |
| 211 | 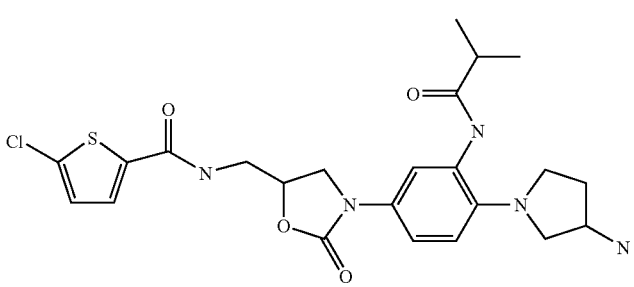 | 2.54 | 69.8 |
| 212 | 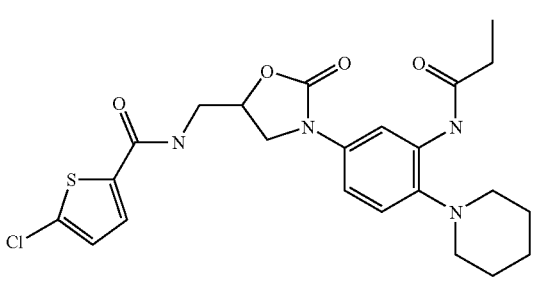 | 3.84 | 59.2 |
| 213 | 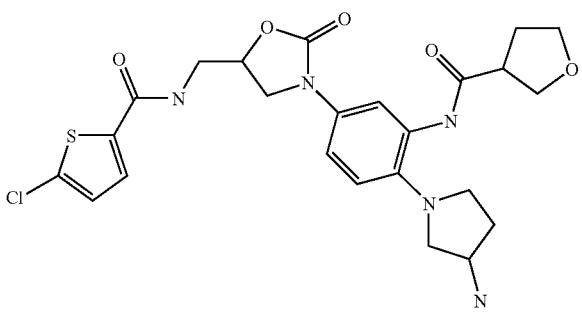 | 2.41 | 67.8 |
| 214 | 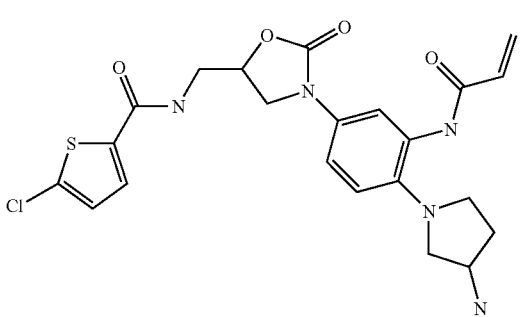 | 2.41 | 75.4 |

| Example | Structure | Ret. time | HPLC [%] |
| --- | --- | --- | --- |
| 215 | 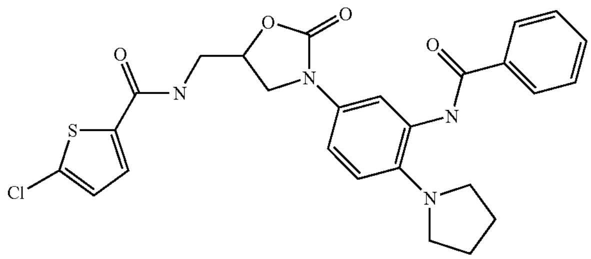 | 4.01 | 81.3 |
| 216 | 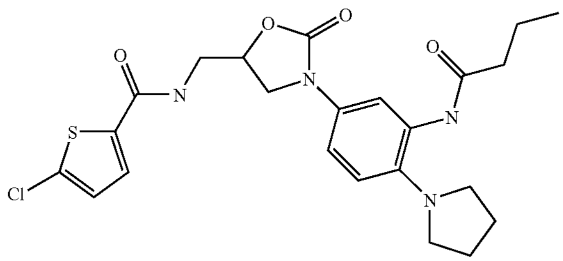 | 3.46 | 49.5 |
| 217 | 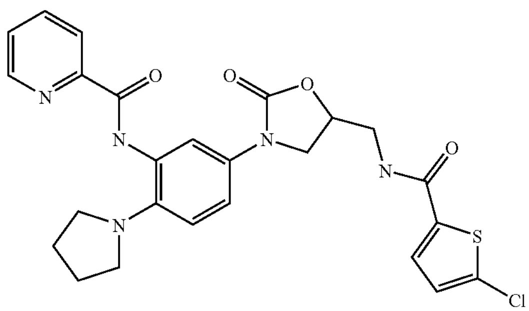 | 4.4 | 60.2 |
| 218 | 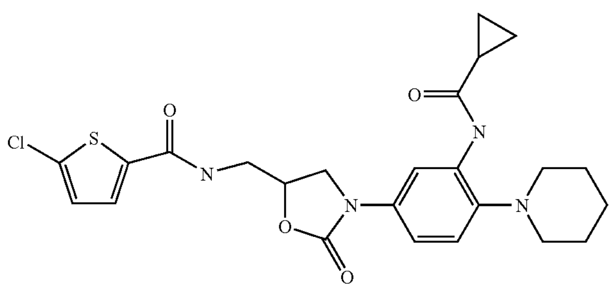 | 3.79 | 70.9 |
| 219 | 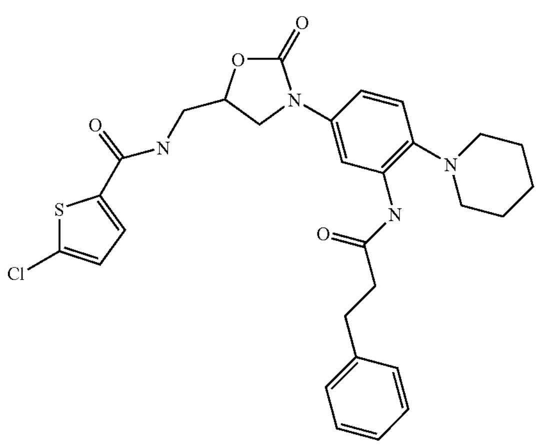 | 4.57 | 51.5 |

-continued
| Example | Structure | Ret. time | HPLC [%] |
|---|---|---|---|
| 220 | 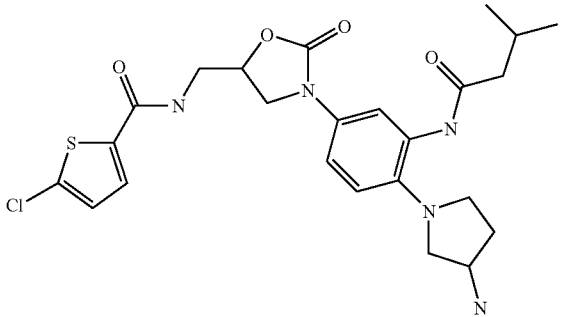 | 2.68 | 100 |
| 221 | 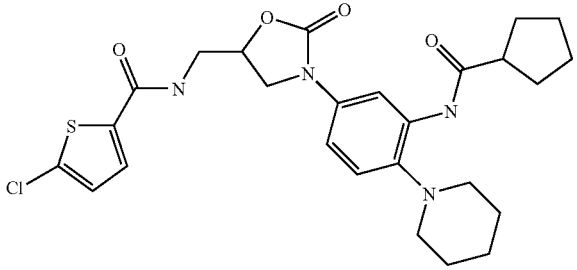 | 4.53 | 63.5 |
| 222 | 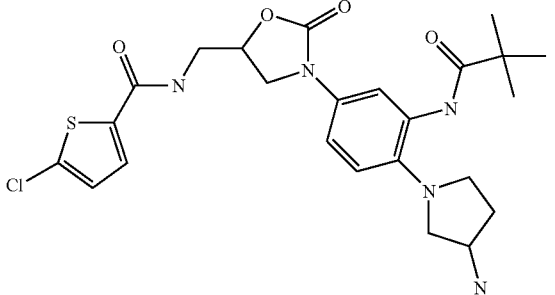 | 2.66 | 89.2 |
| 223 | 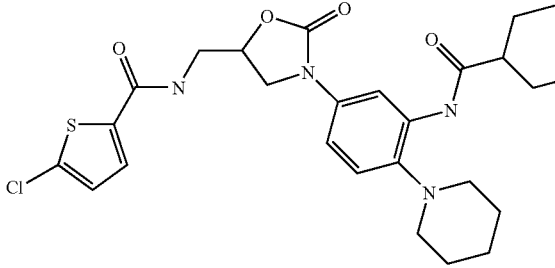 | 4.76 | 69.3 |
| 224 | 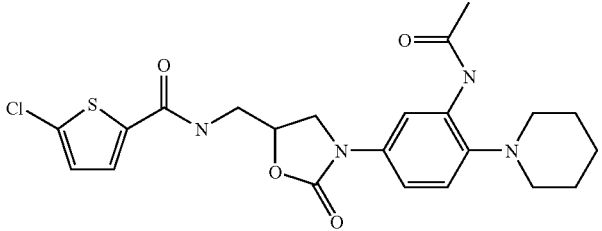 | 3.45 | 77.4 |

-continued

| Example | Structure | Ret. time | HPLC [%] |
|---|---|---|---|
| 225 | 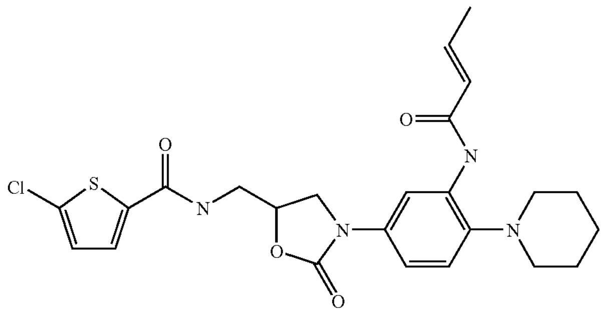 | 3.97 | 63.2 |
| 226 | 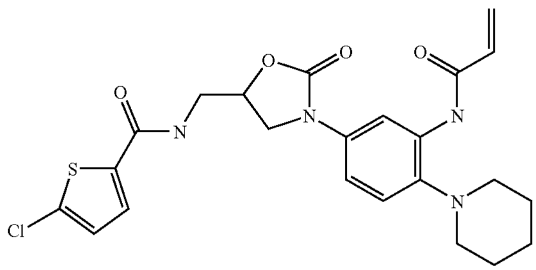 | 3.94 | 61.4 |
| 227 | 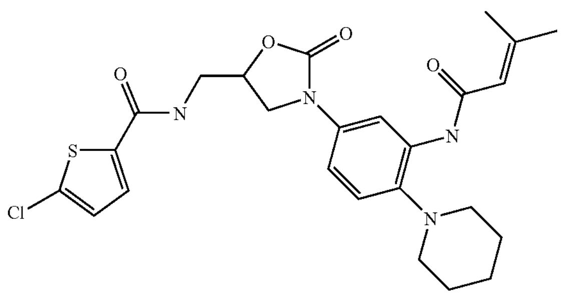 | 4.15 | 66.3 |
| 228 | 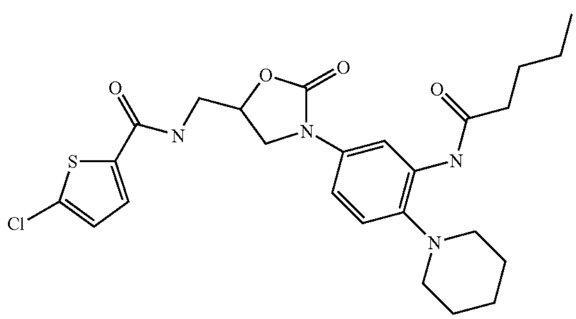 | 4.41 | 55.1 |
| 229 | 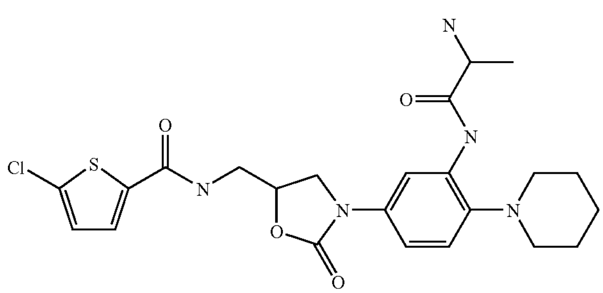 | 2.83 | 41.1 |

-continued

| Example | Structure | Ret. time | HPLC [%] |
|---|---|---|---|
| 230 | 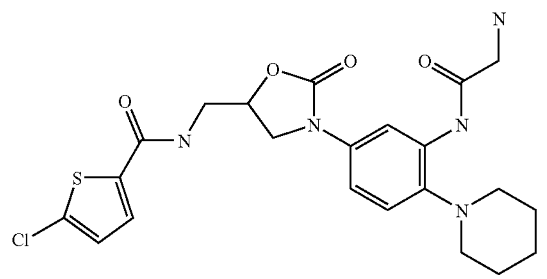 | 2.7 | 83 |
| 231 | 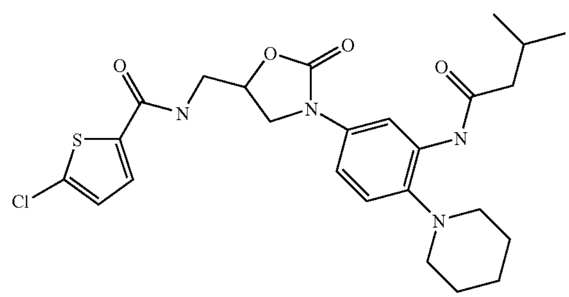 | 4.39 | 64.2 |
| 232 | 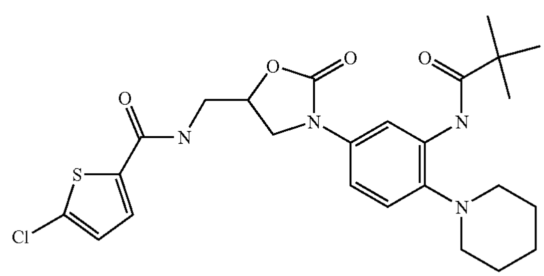 | 4.85 | 74.9 |
| 233 | 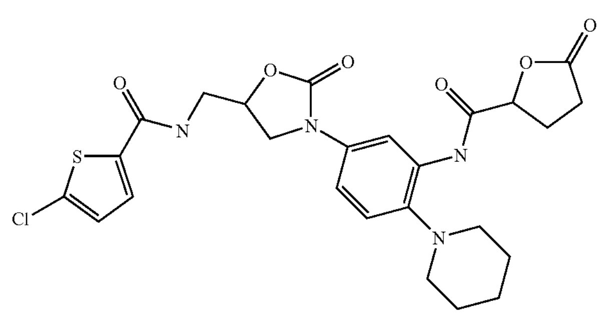 | 4.17 | 41 |
| 234 | 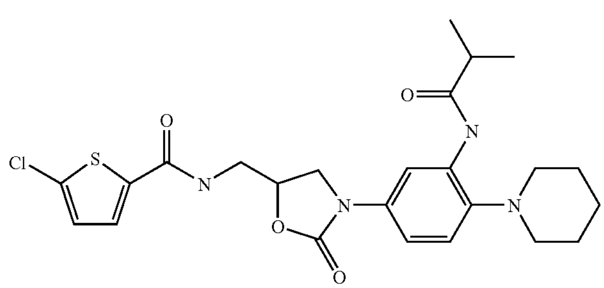 | 4.21 | 61.8 |

-continued

| Example | Structure | Ret. time | HPLC [%] |
|---|---|---|---|
| 235 | 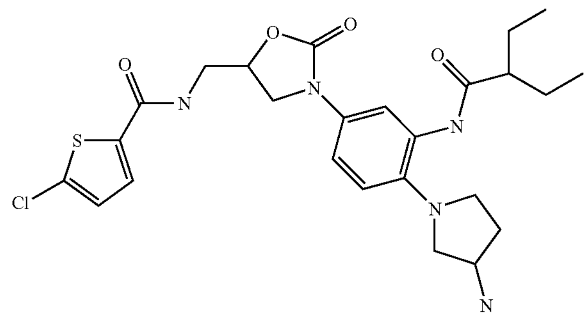 | 2.75 | 100 |
| 236 | 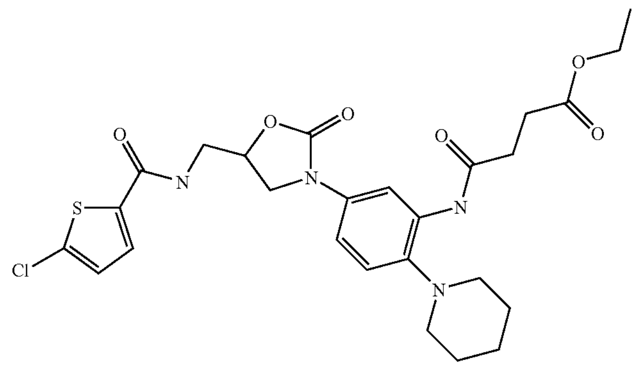 | 3.94 | 50 |
| 237 | 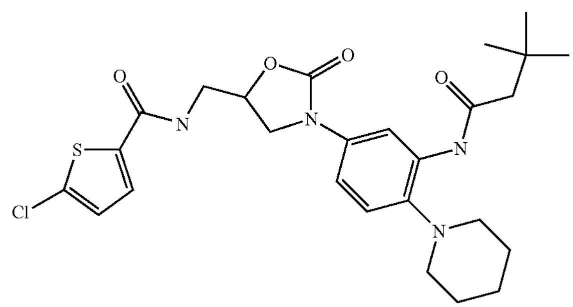 | 4.65 | 75.8 |
| 238 | 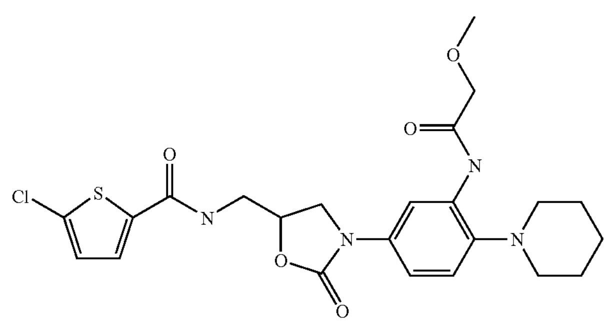 | 4.4 | 75.3 |
| 239 | 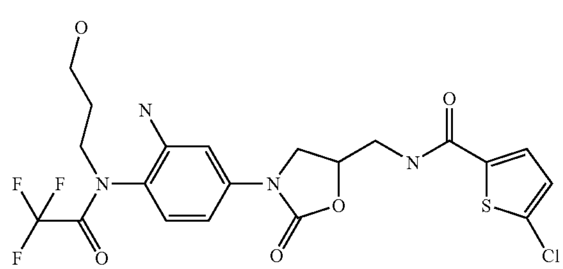 | 4.24 | 62.2 |

-continued

| Example | Structure | Ret. time | HPLC [%] |
|---|---|---|---|
| 240 | 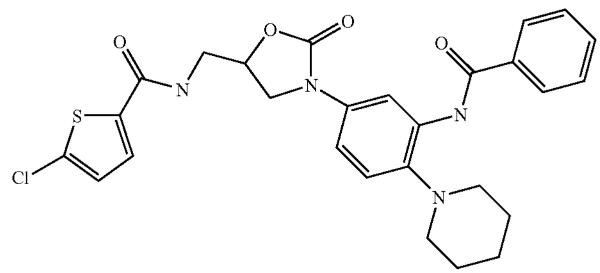 | 4.76 | 75.1 |
| 241 | 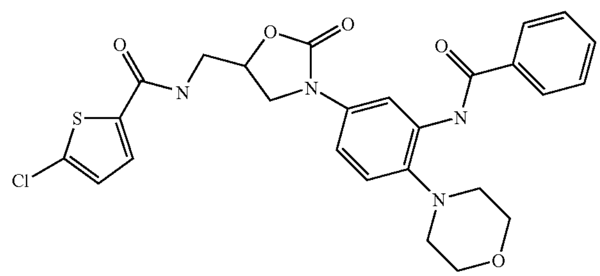 | 4.17 | 72.5 |
| 242 | 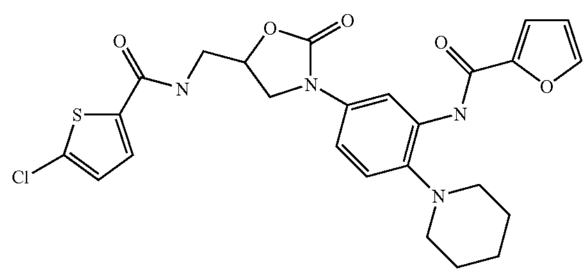 | 4.6 | 74.8 |
| 243 | 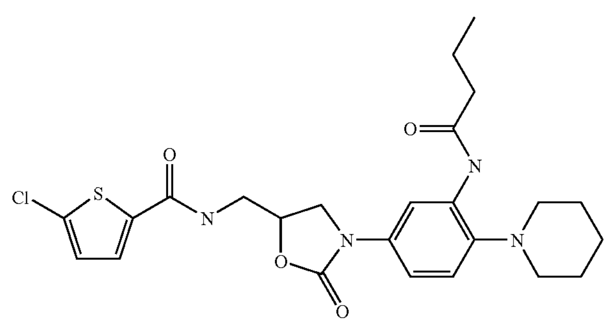 | 4.12 | 51.6 |

-continued
| Example | Structure | Ret. time | HPLC [%] |
|---|---|---|---|
| 244 | 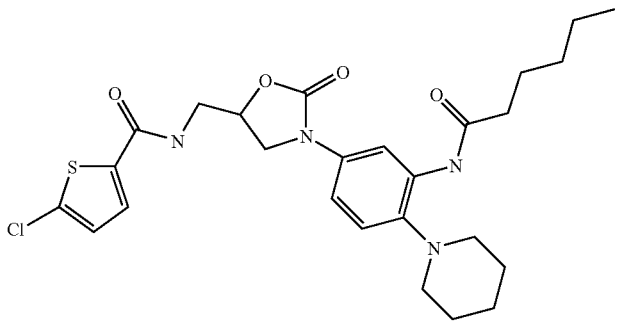 | 4.71 | 66.2 |
| 245 | 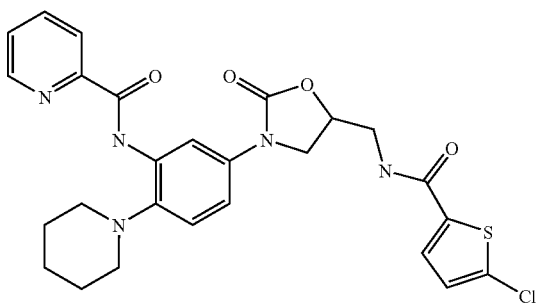 | 4.86 | 62 |
| 246 | 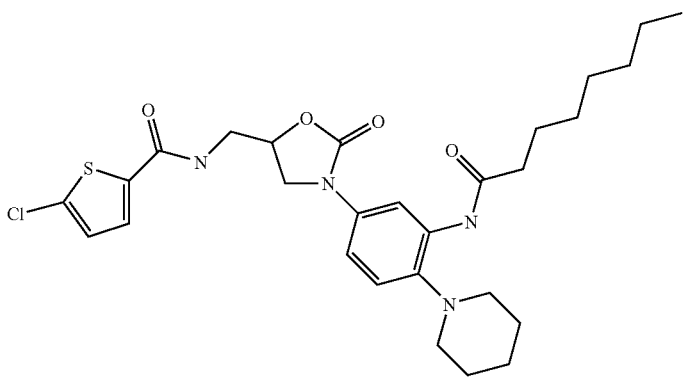 | 5.23 | 58.3 |
| 247 | 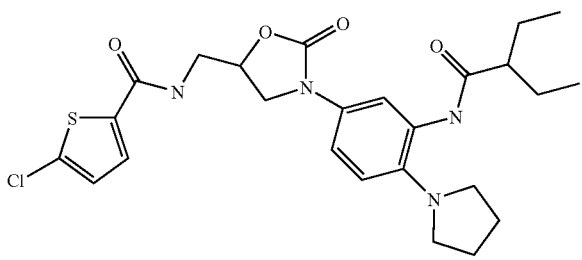 | 4.17 | 72.4 |

| Example | Structure | Ret. time | HPLC [%] |
|---|---|---|---|
| 248 | 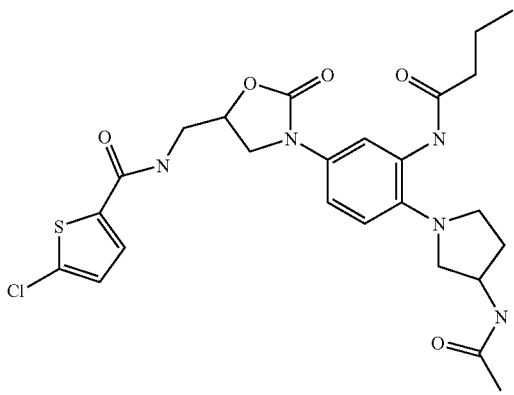 | 3.35 | 59.6 |
| 249 | 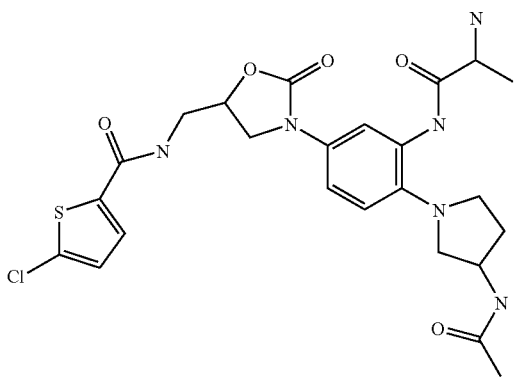 | 2.41 | 60.3 |
| 250 | 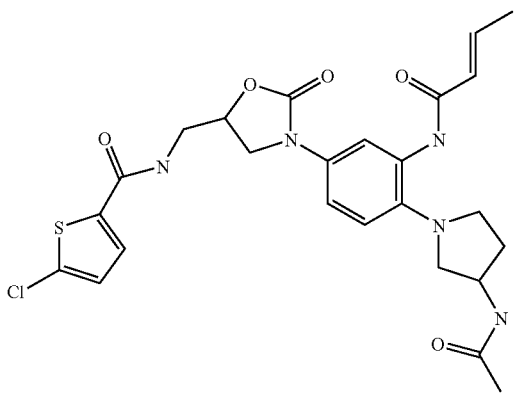 | 3.31 | 65.2 |
| 251 | 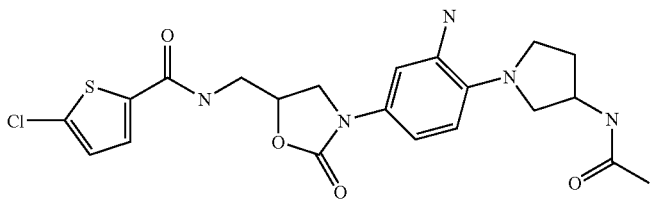 | 2.86 | 36.5 |

-continued

| Example | Structure | Ret. time | HPLC [%] |
|---|---|---|---|
| 252 | 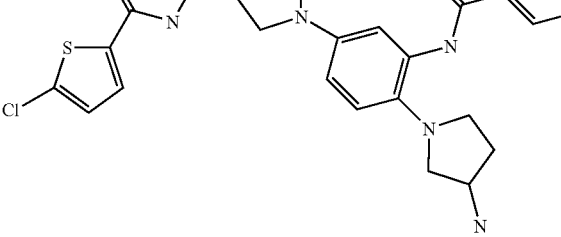 | 2.69 | 89.8 |
| 253 | 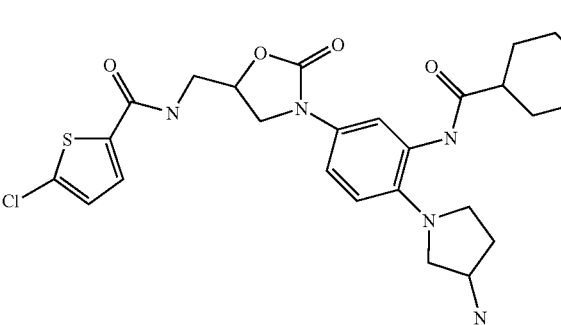 | 2.81 | 67.4 |
| 254 | 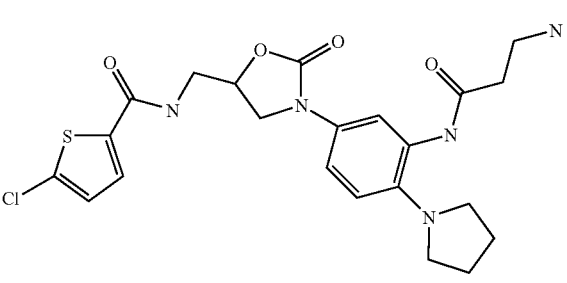 | 2.19 | 75.4 |

All products of the solid phase-assisted synthesis were characterized by LC-MS. The following separation system was routinely used for this: HP 1100 with UV detector (208-400 nm), 40° C. oven temperature, Waters Symmetry C18 column (50 mm×2.1 mm, 3.5 μm), mobile phase A: 99.9% acetonitrile/0.1% formic acid, mobile phase B: 99.9% water/0.1% formic acid; gradient:

| Time | A: % | B: % | Flow rate |
|---|---|---|---|
| 0.00 | 10.0 | 90.0 | 0.50 |
| 4.00 | 90.0 | 10.0 | 0.50 |
| 6.00 | 90.0 | 10.0 | 0.50 |

-continued

| Time | A: % | B: % | Flow rate |
|---|---|---|---|
| 6.10 | 10.0 | 90.0 | 1.00 |
| 7.50 | 10.0 | 90.0 | 0.50 |

The substances were detected by means of a Micromass Quattro LCZ MS, ionization: ESI positive/negative.

The radical(s)

or —O present in the structures detailed above always mean a

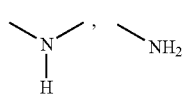

or —OH function.

The invention claimed is:

1. A combination comprising
A) at least one compound of the formula (I)

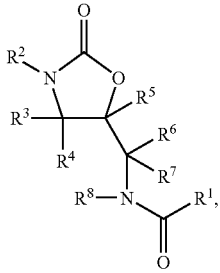 (I)

in which
R$^1$ is 2-thiophene which is substituted in position 5 by a radical selected from chlorine, bromine, methyl and trifluoromethyl,
R$^2$ is D-A-:
where:
the radical "A" is phenylene;
the radical "D" is a saturated 6-membered heterocycle which is linked via a nitrogen atom to "A", and which has a carbonyl group directly adjacent to the linking nitrogen atom, and
in which a ring carbon member may be replaced by a heteroatom selected from the series S, N and O;

where
the group "A" defined above may optionally be substituted once or twice in the meta position relative to the linkage to the oxazolidinone by a radical selected from fluorine, chlorine, nitro, amino, trifluoromethyl, methyl and cyano, and
R$^3$, R$^4$, R$^5$, R$^6$, R$^7$ and R$^8$ are hydrogen, and
B) a platelet aggregation inhibitor.

2. The combination as claimed in claim 1, wherein the compound A) is 5-chloro-N-({(5S)-2-oxo-3-[4-(3-oxo-4-morpholinyl)phenyl]-1,3-oxazolidin-5-yl}methyl)-2-thiophenecarboxamide of the formula

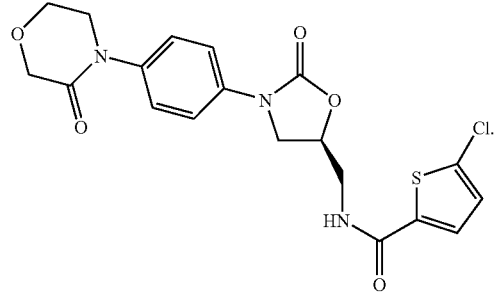

3. The combination as claimed in claim 1, wherein the platelet aggregation inhibitor is a clopidogrel.

4. A pharmaceutical composition comprising at least one combination as claimed in claims 1, 2 or 3 and one or more pharmacologically suitable excipients and/or carriers.

* * * * *